US012320014B2

(12) United States Patent
Reed et al.

(10) Patent No.: US 12,320,014 B2
(45) Date of Patent: *Jun. 3, 2025

(54) MICROORGANISMS AND ARTIFICIAL ECOSYSTEMS FOR THE PRODUCTION OF PROTEIN, FOOD, AND USEFUL CO-PRODUCTS FROM C1 SUBSTRATES

(71) Applicant: Kiverdi, Inc., Pleasanton, CA (US)

(72) Inventors: John S. Reed, Pleasanton, CA (US); Jil Geller, Pleasanton, CA (US); Sonali Hande, Pleasanton, CA (US)

(73) Assignee: KIVERDI, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/210,901

(22) Filed: Jun. 16, 2023

(65) Prior Publication Data

US 2024/0060191 A1 Feb. 22, 2024

Related U.S. Application Data

(63) Continuation of application No. 16/086,572, filed as application No. PCT/US2017/023110 on Mar. 18, 2017, now Pat. No. 11,725,290.

(60) Provisional application No. 62/310,705, filed on Mar. 19, 2016, provisional application No. 62/454,347, filed on Feb. 3, 2017.

(51) Int. Cl.
C25B 1/04 (2021.01)
C12N 1/20 (2006.01)
C12P 1/04 (2006.01)
C12P 5/00 (2006.01)
C12P 7/64 (2022.01)
C12P 7/6409 (2022.01)
C12P 13/00 (2006.01)
C12P 13/04 (2006.01)
C12P 17/16 (2006.01)
C12P 21/02 (2006.01)
C12P 25/00 (2006.01)

(52) U.S. Cl.
CPC ............... C25B 1/04 (2013.01); C12N 1/20 (2013.01); C12P 1/04 (2013.01); C12P 5/00 (2013.01); C12P 7/64 (2013.01); C12P 7/6409 (2013.01); C12P 13/001 (2013.01); C12P 13/04 (2013.01); C12P 17/167 (2013.01); C12P 21/02 (2013.01); C12P 25/00 (2013.01)

(58) Field of Classification Search
CPC ..... C25B 1/04; C12N 1/20; C12P 1/04; C12P 5/00; C12P 7/64; C12P 7/6409; C12P 13/001; C12P 13/04; C12P 17/167; C12P 21/02; C12P 25/00; C07K 16/2896; C07K 2317/24; C07K 2317/52; C07K 2317/71; C07K 2317/76; C07K 2317/92; G01N 33/573; G01N 33/84; G01N 2333/916
See application file for complete search history.

(56) References Cited

U.S. PATENT DOCUMENTS

| | | | |
|---|---|---|---|
| 3,420,739 A | 1/1969 | Bongers et al. |
| 3,442,620 A | 5/1969 | Jack et al. |
| 3,852,492 A | 12/1974 | Brown et al. |
| 3,867,255 A | 2/1975 | Newell et al. |
| 3,887,431 A | 6/1975 | Robbins et al. |
| 3,888,740 A | 6/1975 | Ishizaki et al. |
| 3,891,774 A | 6/1975 | Baker et al. |
| 4,007,088 A | 2/1977 | Fencl et al. |
| 4,367,146 A | 1/1983 | Pollock et al. |
| 4,426,450 A | 1/1984 | Donofrio |
| 4,607,011 A | 8/1986 | Kaplan et al. |
| 4,859,588 A | 8/1989 | Sublette |
| 5,173,429 A | 12/1992 | Gaddy et al. |
| 5,186,731 A | 2/1993 | Parker |
| 5,250,427 A | 10/1993 | Weaver et al. |
| 5,342,702 A | 8/1994 | MacGregor |
| 5,593,886 A | 1/1997 | Gaddy |
| 5,807,722 A | 9/1998 | Gaddy |
| 5,821,111 A | 10/1998 | Gaddy et al. |
| 6,187,565 B1 | 2/2001 | Weaver |
| 6,340,581 B1 | 1/2002 | Gaddy |
| 7,285,402 B2 | 10/2007 | Gaddy et al. |
| 7,332,077 B2 | 2/2008 | Pollock |
| 7,687,091 B2 | 3/2010 | Moen et al. |
| 7,776,124 B2 | 8/2010 | Binder et al. |
| 2002/0040871 A1 | 4/2002 | Garcia et al. |
| 2003/0003528 A1 | 1/2003 | Brzostowicz et al. |
| 2003/0022364 A1 | 1/2003 | Parent et al. |
| 2003/0087234 A1 | 5/2003 | Heumann |

(Continued)

FOREIGN PATENT DOCUMENTS

| | | |
|---|---|---|
| CA | 2255212 | 12/1998 |
| DE | 2160478 A1 | 6/1972 |

(Continued)

OTHER PUBLICATIONS

Wiegel, J. , Prokaryotes, 2006, vol. 5, p. 290-314. DOI: 10.1007/0-387-30745-1_16 (Year: 2006).*

Mersmann, A., et al., Packungskolnnen, Chem.-Ing.-Tech. 58(1):19-31, 1986.

Miltner, A., et al., Non-phototrophic CO2 fixation by soil microorganisms, Plant and Soil 269:193-203, 2005.

Miura, A., et al., A Soluble NADH-Dependent Fumarate Reductase in the Reductive Tricarboxylic Acid Cycle of Hydrogenobacter thermophilus TK-6, Journal of Bacteriology 190(21)7170-7177, 2008.

Munoz, et al., Algal-bacterial processes for the treatment of hazardous contaminants: a review, Water Research 40(15): 2799-1815, 2006.

Murugan, P., et al., A new biological recovery approach for PHA using mealwork, Tenebrio molitor, Journal of Biotechnology 239:98-105, 2016.

(Continued)

Primary Examiner — Kade Ariani
(74) Attorney, Agent, or Firm — Fountainhead Law Group, PC; Jill A. Jacobson

(57) ABSTRACT

Microorganisms and bioprocesses are provided that convert gaseous C1 containing substrates, such as syngas, producer gas, and renewable $H_2$ combined with $CO_2$, into nutritional and other useful bioproducts.

16 Claims, 20 Drawing Sheets

(56) References Cited

U.S. PATENT DOCUMENTS

| | | |
|---|---|---|
| 2003/0134822 A1 | 7/2003 | Maekawa et al. |
| 2004/0078846 A1 | 4/2004 | Desouza et al. |
| 2004/0203134 A1 | 10/2004 | Pyntikov et al. |
| 2006/0286205 A1 | 12/2006 | Fichtali et al. |
| 2008/0022593 A1 | 1/2008 | Gur et al. |
| 2008/0193987 A1 | 8/2008 | Mantelatto et al. |
| 2009/0117194 A1 | 5/2009 | Burja et al. |
| 2009/0130706 A1 | 5/2009 | Berzin et al. |
| 2009/0142322 A1 | 6/2009 | Ye |
| 2009/0191593 A1 | 7/2009 | Burk et al. |
| 2010/0093860 A1 | 4/2010 | Boon et al. |
| 2010/0235934 A1 | 9/2010 | Friedman et al. |
| 2011/0020884 A1 | 1/2011 | Latouf et al. |
| 2012/0015413 A1 | 1/2012 | Sichwart et al. |
| 2012/0084886 A1 | 4/2012 | Lopez-Cervantes et al. |
| 2013/0089899 A1 | 4/2013 | Kurek et al. |
| 2013/0149755 A1 | 6/2013 | Reed |
| 2014/0273112 A1 | 9/2014 | Reed et al. |
| 2015/0017694 A1 | 1/2015 | Kurek |
| 2015/0044327 A1 | 2/2015 | Feinberg et al. |
| 2016/0073671 A1 | 3/2016 | Geistlinger et al. |
| 2019/0000124 A1 | 1/2019 | Sefton et al. |

FOREIGN PATENT DOCUMENTS

| | | |
|---|---|---|
| EP | 0131220 A2 | 1/1985 |
| EP | 1264895 A1 | 12/2002 |
| EP | 2135939 A1 | 12/2009 |
| JP | 54119091 A2 | 9/1979 |
| JP | 6169783 A2 | 6/1994 |
| JP | 7163363 A2 | 6/1995 |
| JP | 2516154 B2 | 7/1996 |
| JP | 2912684 B2 | 6/1999 |
| JP | 2004-051920 A2 | 2/2004 |
| JP | 2013-542710 A2 | 11/2013 |
| KR | 2003020766 | 3/2003 |
| KR | 1336680 B1 | 12/2013 |
| WO | 1998000558 | 1/1998 |
| WO | 2002008438 | 1/2002 |
| WO | 2005001981 | 1/2005 |
| WO | 2007024255 | 3/2007 |
| WO | 2009009388 | 1/2009 |
| WO | 2009058028 | 5/2009 |
| WO | 20090113853 | 9/2009 |
| WO | 2011014953 | 2/2011 |
| WO | 2011056183 | 5/2011 |
| WO | 201112695 | 9/2011 |
| WO | 2011139804 | 11/2011 |
| WO | 2013090769 | 6/2013 |
| WO | 2013148348 | 10/2013 |
| WO | 2014145194 | 9/2014 |
| WO | 2015027209 | 2/2015 |
| WO | 2015177800 | 11/2015 |
| WO | 2016044423 | 3/2016 |
| WO | 2017015321 | 1/2017 |
| WO | 2017165244 | 9/2017 |

OTHER PUBLICATIONS

Nile tilapia—Fertilizers and fertilization, Food and Agriculture Organization of the United Nations (FAO), http://fao.org/fishery/affris/species-profiles/nile-tilapia/fertilizers-and-fertilization/en/.

Nippon Nogeikagaku Kaishi 61 (10): 1322-1328, 1987.

Ong, S. Y., et al., An integrative study on biologically recovered polyhydroxyalkanaoates (PHAs) and simultaneous assessment of gut microbiome in yellow mealworm, Journal of Biotechnology 265:31-39, 2018.

Paoli, G.C., et al., Aerobic chemolithoautotrophic growth and RubisCO function in Rhodobacater capsulatus and a spontaneous gain of function mutant of Rhodobacter sphaeroides, Arch Microbial 170:8-17, 1998.

Papoutsakis, E.T., Equations and calculations for fermentations of butyric acid bacteria, Biotechnology & Bioengineering 26(2):174-187, 1984.

Rapp, P., et al., Formation, Isolation and Characterization of Trehalose Dimycolates from Rhodococcus erythropilis Grown in n-Alkanes, Journal of General Microbiology 115:491-503, 1979.

Repaske, R., et al., Dense Autotrphic Culutures of Alcaligenes eutrophus, Applied and Environmental Microbiology B2{4}:592-597, 1976.

Roth, M.S., The engine of the reef: photobiology of coral-algal symbiosis, Frontiers in Microbiology 5: Article 422, Aug. 22, 2014.

Schlegel, H.G., et al., The Production of Biomass from Hydrogen and Carbon Dioxide, Advances in Biochemical Engineering, 1:143-168, 1971.

Scott, K.M., et al., CO2 uptake and fixation by endosymbiotic chemoautotrophs from the bivalve solemya velum, applied and Environmental Microbiology 73(4):1174-1179, 2007.

Searchinger, T., et al., The great balancing act, World Resources Institute Working Paper, Washington, DC, 2013.

Shively, J., et al., Something from Almost Nothing: Carbon Dioxide Fixation in Chemoautotrophs, Annu. Rev. Microbial_ 52:191-230, 1998.

Smith, A.J., et al., Biochemical basis of obligate autotrophy in Blue-Green algae and thiobacilli, Journal of Bacteriology 94{4}:972-983, 1967.

Storebakken, et al., Bacterial protein grown on natural gas in diets for Atlantic salmon, *Salmo salar*, in freshwater, quaculture 241(1-4):413-425, 2004.

Takeshita, T., et al., Studies on Dissolved Hydrogen Behavior in Autotrophic Culture of Alcaligenes eutrophus ATCC H697, J_ Fae. Kyushu Univ. 38(1-2):55-64, 1993.

Tanaka, K., et al., Production of Poly(D-3-Hydroxybutyrate) from CO2 H2, and 02 by High Cell Density Autotrophic Cultivation of Alcaligenes eutrophus, Biotechnology and Bioengineering 45:268-275, 1995.

Taub, F.B., Closed Ecological Systems, Annu. Rev. Ecol. Syst. 5:139-160, 1974.

Thauer, R.K., et al., Methanogenic archaea: ecologically relevant differences in energy conservation, Nat Rev Microbial 6:579-591, 2008.

Tokuda, H., et al., Effects of electrical pre-treatmenton the hydrolysis of agricultural wastes, J. Brew. Soc .. Japan 101 (10):769-775, 2006.

Toyoda, K., et al., The role of two CbbRs in the transcriptional regulation of three ribulose-1,5-biphosphate t; arboxylase/oxygenase genes in Hydrogenovibrio marinus strain MH-110, Microbiology 151 :3615-3625, 2005.

Turner, J., et al., Renewable hydrogen production, Int J Energy Res DOI:10.1002/er.1372, 2007.

Wall, J.D., et al., A pleiotropic mutant of Rhodopseudomonas capsulata defective in nitrogen metabolism, Arch. Microbial_ 115:259-263, 1977.

Volova, T.G., et al., Autotrophic synthesis of polyhydroxyalkanoates by the bacteria *Ralstonia eutropha* in the presence of carbon monoxide, Appl Microbial Biotechnol 58:675-678, 2002.

Voss, I., et al., High cell density cultivation of Rhodococcus opacus for lipid production at a pilot-plant scale, Appl Microbial Biotechnol 55:547-555, 2001.

Wahlund, T.M., et al., Bioconversion of CO2 to Ethanol and other Compounds, Preprints of Papers—American Chemical Society Division Fuel Chemistry 41: 1408-1406, 1996.

Walterman, M., et al., Rhodococcus opacus strain PD630 as a new source of high-value single-cell oil? Isolation • nd characterization of triacylglycerols and other storage lipids, Microbiology 146:1143-1149, 2000.

Watanabe, Y., et al., Microbial CO2 Fixation, Journal of the Agricultural Chemical Society of Japan 61(10):1322-1325, 1987.

Yang, oroperties, E.-1., et Cement al., and Effect of Concrete oyster Reseshell arch substituted for 35(11):2175-2182, fine agg 1975 regate on concrete characteristics: Part i. fundamental properties, Cement and Concrete Research 35(11):2175-2182, 1975.

Yoon, G-L., et al., Chemical-mechanical characteristics of crushed oyster shell, Waste Management 23(9):825-834, 2003.

(56) References Cited

OTHER PUBLICATIONS

Yamamoto, M., et al., Role of two 2-oxoglutarate:ferredoxin oxidoreuctases in Hydrogenobacter thermophilus under aerobi and anaerobic conditions, FEMS Microbial Lett 263:189-193, 2006.
Oren, A., Chemolithotrophy, Encyclopedia of Life Sciences, John Wiley & Sons, Ltd., 2009.
Yoon, H., et al., Oyster shell as substitute for aggregate in mortar, Waste Management & Research 22(3):158-170, 2004.
Alvarez, H., et al., Formation of intracytoplasmic inclusions by Rhodococcus opacus strain PD630, Arch Microbial • 65:377-386, 1996.
Anderson, A.J., et al., Occurrence, Metabolism, Metabolic Role, and Industrial Uses of Bacterial Polyhydroxyalkanoates, Microbiological Reviews 54(4):450-472, 1990.
Anschau, A., Excerpt from Nutrient Delivery: Nanotechnology in the Agri-Food Industry, Chapter 20, pp. 749-794, eo11.
Barbir, F., PEM electrolysis for production of hydrogen from renewable energy sources, Solar Energy 78:661-669, 2005.
Barton, LL, The Cell Wall Matrix, Structural and Functional Relationships in Prokaryotes, pp. 136-189, Springer.
Bligh, E.G., et al., A Rapid Method of Total Lipid Extraction and Purification, Canadian Journal of Biochemistry and Physiology 37(8):911-917, 1959.
Bogdahn, I., Agriculture-independent, sustainable, fail-safe and efficient food production by autotrophic single-cell protein, PeerJ PrePrints, Sep. 17, 2015 https://dx.doi.org/10/7287/peerj.preprints.1279v3.
Bongers, L., Energy Generation and Utilization in Hydrogen Bacteria, Journal of Bacteriology 104(1):145-151, 1979.
Calloway, D.H., et al., Protein Quality of the Bacterium *Hydrogenomonas eutropha*, Applied Microbiology 17(1):176-178, 1969.
Calloway, D.H., et al., Investagation of the Nutritional Properties of Hydrogenomonas eutropha, Final Report to the National Aeronautics and Space Administration NGR 05-003-089, 1968.
Campbell, B.J., et al., Hydrogen isotopic fractionation in lipid biosynthesis by H2-consuming Desulfobacterium autotrophicum, Geochiica et Cosmochimica Acta 73:2744-2757, 2009.
Chang, C.C., et al., Hydrogenotrophic denitrification with immobilized Alcaligenes eutrophus for drinking water treatment, Bioresource Technology 69:53-58, 1999.
Chee, J.Y., et al., The Potential Applicataion of Cupriavidus necator as Polyhydroxy-alkanoates Producer and Single Cell Protein: A Review on Scientific, Cultural and Religious Perspectives, Applied Food Biotechnology 6(1):19-34, 20H.
Dominic Frigon, rRNA and Poly- - Hydroxybutyrate Dynamics in Bioreactors Subjected to Feast and Famine Cycles, Applied and Environmental Microbiology, Apr. 2006, p. 2322-2330.
D. Perlman (ed), Fermentation Advances (1969). Chapter Title: From electricity via Water electrolysis to Food. Chapter Author: H.G. Schlegel, pp. 807-832.
Juergen Weigel, the Genus *Xanthobacter*, Chapter in book "The Prokaryotes", pp. 290-314.

* cited by examiner

|  | GROWTH CONDITIONS | |
| ORGANISM | HETEROTROPHIC | CHEMOAUTOTROPHIC |
| --- | --- | --- |
| R. OPACUS (DSM 44193) | 9.00 (6d) | 0.00 |
| R. OPACUS (DSM 43205) | 9.00 (6d) | 1.00 (5d) |
| RHODOCOCCUS SP. (DSM 3346) | 2.40 (3d) | 0.51 (9d) |
| CUPRIAVIDUS NECATOR (DSM 531) | 2.20 (3d) | 0.23 (3d) |

FIG. 7

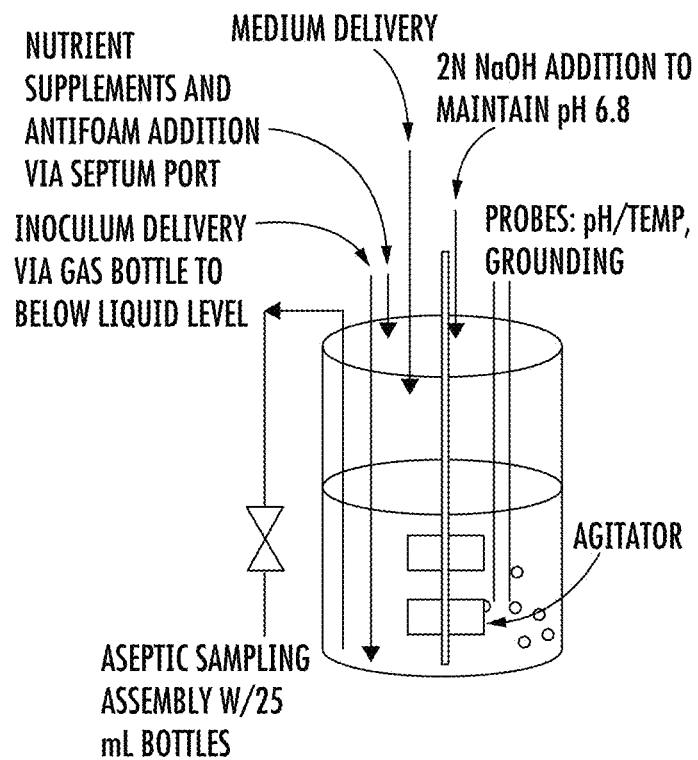
FIG. 21  2 L BIOREACTOR (1.5 L WORKING VOLUME))
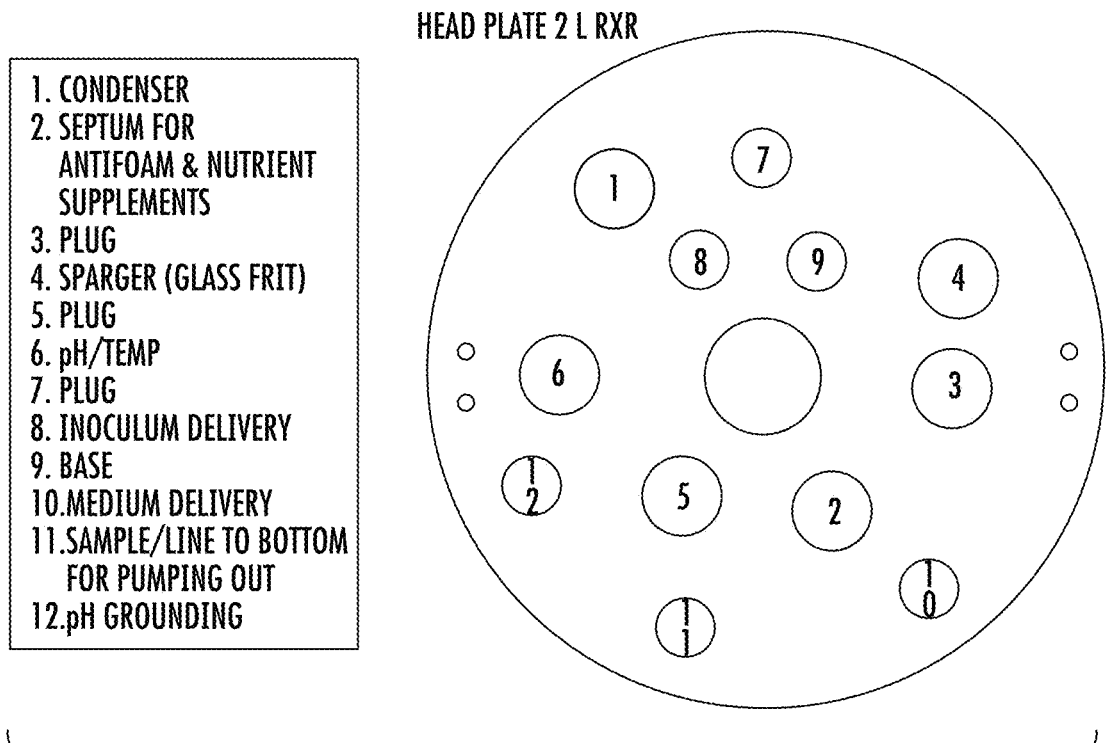
FIG. 22

2 L REATOR CONFIGURATION, GAS LINES

HUMAN DIGESTION, RESPIRATION, AND EXCRETION   $C_5H_7O_2N + 5O_2 \rightarrow 4.5CO_2 + 2.5H_2O + 0.5CH_4N_2O$
BIOSYNTHESIS                             $16.4H_2 + 4.5CO_2 + 3.2O_2 + 0.5CH_4N_2O \rightarrow C_5H_7O_2N + 13.9H_2O$
ELECTROLYSIS                             $16.4H_2O \rightarrow 16.4H_2 + 8.2O_2$

MICROORGANISMS AND ARTIFICIAL ECOSYSTEMS FOR THE PRODUCTION OF PROTEIN, FOOD, AND USEFUL CO-PRODUCTS FROM C1 SUBSTRATES

CROSS-REFERENCE TO RELATED APPLICATIONS

This application is a continuation of U.S. Application Ser. No. 16/086,572, filed Sep. 19, 2018, which is a U.S. national stage application under 35 U.S.C. § 371 of PCT/US2017/023110, filed on Mar. 18, 2017 and published as WO2017/165244 A1 on Sep. 28, 2017, which claims the benefit of U.S. Provisional Application No. 62/310,705, filed on Mar. 19, 2016, and 62/454,347, filed on Feb. 3, 2017, both of which are incorporated by reference herein in their entireties.

FIELD OF THE INVENTION

The inventive subject matter relates to the biological production of amino acids and proteins and other biomass constituents, in a microbial system, using a gaseous substrate such as synthesis gas or producer gas or pyrolysis gas or $H_2$ and $CO_2$ gas mixtures, as a carbon and energy source. The invention also relates to the use of microbial amino acids, proteins, and other biomass constituents to feed or provide nutrients to other heterotrophic organisms, animals, or humans. Amino acids, proteins, and other biomass constituents produced according to the present invention can be consumed and used as nutrients by other organisms for the production of food and other bio-based products.

This disclosure relates to compositions capable of producing and methods of producing amino acids, proteins, and other biomass constituents through cultivating bacteria or other microorganisms that grow on carbon-containing gases such as syngas, producer gas, $CO_2$, carbon monoxide and mixtures of the same containing hydrogen gas. This disclosure further relates to methods of fixing carbon from gaseous input into useful organic molecules such as amino acids, proteins, and other nutrients. The bacteria and/or microorganisms of the invention can be genetically engineered for use in the methods or other aspects of the invention described herein. In some other aspects of the invention described herein the microorganisms are not genetically engineered.

This disclosure further relates to methods of fixing carbon from gas into useful organic molecules such as amino acids, proteins, and other nutrients. The present invention further describes mechanisms to confer to an organism the ability to produce, and/or to enhance production by an organism of, carbon-based products, through the conversion of carbon dioxide, or other inorganic carbon sources, and inorganic energy, including chemical energy from an inorganic chemical, or directly from an electrical source, into carbon-based products, and in particular amino acids, proteins, and other nutrients of commercial value.

This disclosure further relates to artificial ecologies, engineered trophic systems, closed ecological systems, microcosms, continuous culture systems, bioregenerative and closed-loop life-support systems.

BACKGROUND

Sustainable and renewable sources of amino acids, proteins, and other nutrients are needed to help meet growing food needs. There is also a need to reduce the amount of carbon dioxide and other greenhouse gas (GHG) emissions to the atmosphere, as well as to reduce global energy consumption based upon coal, oil, and natural gas in food production systems. Increased demand in the global economy has placed increasing pressure on land and water resources. Increased pressure has also been placed on traditional fossil hydrocarbon inputs for the production of food and other agriculturally derived products. Many industries, including modern agriculture, rely heavily on the availability of fossil hydrocarbon sources as an input for the production and processing of crops. Cost-effective alternatives to current incumbent practices could help mitigate the upward pressure on land use, natural habitats, water, fossil resource demand, raw material costs, and greenhouse gas emissions.

Biologic systems that fix gaseous carbon through natural biochemical metabolic processes are known. The current agricultural system, based on photosynthesis in higher plant crops, is one example. Algal systems have also been developed to create food and other agriculturally derived products from $CO_2$ through photosynthetic reactions. There are also heterotrophic reactions and productions utilizing fixed carbon feedstocks, such as sugar, which indirectly depend upon photosynthesis. Animal husbandry and aquaculture generally at the present time have as ultimate inputs, the products of photosynthesis, in the form of various feeds. Artificial or compound feeds are commonly used which are mixtures of feedstuffs, and vitamin and mineral premixes that are formulated to contain desired levels of essential nutrients and energy. These feeds are often the products of agriculturally produced crops. Or, in some cases, they are sourced from the harvesting or foraging of wild organisms in nature. At the base of this production is generally a photosynthetic trophic layer of primary producers, which are either consumed directly or indirectly. An example of food production which serves to illustrate the direct consumption of wild photosynthetic primary producers is grazing livestock on uncultivated lands. An example which serves to illustrate food production through the indirect consumption of wild photosynthetic primary producers is the use of fishmeal in aquaculture, derived from wild fish stocks such as sardines and anchovies, which in turn feed on photosynthetic algae. However, a number of problems and limitations are confronting current agricultural, animal husbandry, and aquaculture practices, and the photosynthetically based feeds which are currently utilized.

Increasing global population coupled with increased per capita seafood consumption has resulted in a constantly increasing demand for seafood. While demand is rising, many marine fish stocks are already overfished. Aquaculture has helped meet this increasing demand, and improve nutrition and food security in many parts of the world. With the global catch of wild fish stagnant, experts say virtually all of that new seafood will have to be farmed. According to the United Nations Food & Agriculture Organization (FAO), another 40 million tons of seafood per year will be needed worldwide by 2030 just to meet current consumption rates, and "With capture fisheries production stagnating, major increases in fish food production are forecast to come from aquaculture . . . an additional 27 million tonnes of aquaculture production will be needed to maintain the present level of per capita consumption in 2030." Accompanying the rapid growth in aquaculture is growth in the industry of producing feed for aquaculture.

Fish are among the most energy-efficient animals to grow and aquaculture is one of the most resource-efficient ways to produce animal protein. Specifically, fish convert more of the food they eat into body mass than land animals. "Feed Conversion Ratios" (FCR) indicate how many pounds of feed it takes to produce a pound of animal product. Salmon—the most feed-intensive farmed fish—has been found to be far more efficient than other forms of protein production such as via chickens, pork, or beef. The FCR for salmon is reportedly 1.2 while that for chicken: 1.9; pigs: 5.9; and cows: 8.7. What's more, aquaculture's carbon footprint is often a fraction of that of animal husbandry on land. The National Oceanic and Atmospheric Administration (NOAA) Basic Questions about Aquaculture is incorporated herein by reference in its entirety.

Farmed fish are fed diets specially designed for their nutritional needs. This feed may contain all the essential nutrients needed to keep them healthy and growing, and is often in the forms of dried pellets. Fish nutritional needs vary by species. Herbivorous fish eat a feed mixture that may contain plant proteins (e.g., soy, corn), vegetable oils, minerals, and vitamins. In the wild, carnivorous fish such as salmon eat other fish. However even for carnivorous fish a great deal of the diet may include plant proteins, oils, minerals, and vitamins.

In practice, a substantial fraction of aquaculture feed comprises animal protein sources, and in particular, fishmeal. The fishmeal component of aquaculture feed is typically derived from wild-caught fish. However, the widespread practice of harvesting wild fish to feed other captive fish is considered unsustainable. A major challenge facing the aquaculture industry is reducing the heavy reliance on wild-caught species at the bottom of the food chain. Globally, aquaculture uses about half a metric ton of wild whole fish to produce one metric ton of farmed seafood. The amount of fish you get "out" (as seafood) relative to the amount of fish you put "in" (in the diet)—known as "fish-in/fish-out" (FIFO) conversion ratios—vary greatly among species. New feed made from soybeans and fishery byproducts has helped lower the dependency on overfished stocks, but experts warn much more work is needed to ensure fish farming can be expanded without despoiling the environment or depleting the oceans of other species. About ¾ of the fishmeal and oil are produced from the harvest of small, open-ocean (pelagic) fish called forage fish such as anchovies, herring, menhaden, capelin, pilchard, sardines, and mackerel. While they have been major ingredients of swine and poultry feeds for many decades, a growing percentage of the forage fish resource is being used to manufacture aquatic feeds due to the worldwide growth of aquaculture over the past two decades. Aquaculture's share of the forage-fish catch has nearly doubled since 2000 and now consumes nearly 70 percent of the global fish meal supply and almost 90 percent of the world's fish oil. The harvest for these various uses has led to a decline in sardines, anchovies, and other natural forage fish. Many countries are sending ships to Antarctica to harvest more than 200,000 tons a year of tiny krill—a major food source for penguins, seals, and whales. To critics of current aquaculture practices this has been called "vacuuming up the bottom of the food chain in order to chum out slabs of relatively cheap protein" and has been described as "ecological insanity".

The challenge confronting aquaculture looking forward is to increase efficiency and sustainability. With rising costs for fishmeal, aquaculture producers are attempting to develop cost-effective, yet healthful alternatives for use in aquaculture feeds. Potential alternatives being investigated include meals and oils from plants (the greatest current source of protein and edible oil in general), fish processing waste, yeast, algae, insects, bugs and other special meals, and seaweed.

Fish farmers have also been increasingly turning to farming omnivorous fish like tilapia, which can readily use feeds that contain soybeans and other grains. Tilapia is an omnivorous grazer that feeds on phytoplankton, periphyton, aquatic plants, small invertebrates, benthic fauna, detritus, bacteria, and bacterial films associated with detritus. Nile tilapia can filter feed by entrapping suspended particles, including phytoplankton and bacteria, on mucous in the buccal cavity, although its main source of nutrition is reportedly obtained by surface grazing on periphyton mats. Early juvenile Tilapia and young fish are omnivorous, feeding mainly on zooplankton and zoobenthos but also on detritus, aufwuchs, and phytoplankton. The pH of the Tilapia stomach varies with the degree of fullness and when full can be as low as 1.4, such that lysis of blue-green and green algae and diatoms is facilitated. The Tilapia requirements for protein, lipids, vitamins, minerals, and carbohydrates, vary by maturity.

The dietary requirements of fish in the early developmental stages are often distinct from those of adults. Almost all juvenile fishes, including herbivores, are typically carnivores and feed on zooplankton and small invertebrates such as crustaceans in the larvae, fry and young stages. The production of most marine finfish species currently depends on live-feed to sustain finfish larvae through the first weeks of life. This live-feed often comprises Zooplankton, which are microscopic or small organisms living in fresh, brackish, or seawater or other saline waters. Zooplankton organisms include rotifers [Phylum rotifera], order Cladoceran (e.g. *Daphnia* sp., *Moina* sp.), sub-class Copepoda (e.g. Cyclops), and Brine shrimp (*Anemia* sp.). The economic production of zooplankton is reported to currently impede successful aquaculture of certain marine finfish.

Aquaculture's unrealized potential has led some scientists, economists, and policymakers to endorse it as one of our best options for feeding the world's burgeoning population, which is expected to increase from 7 billion to 9 billion people by 2050. To fully realize this potential, new sources of protein and other nutrients for aquaculture feed are required.

Bacterial and other microbial cells have been applied to process sugar feedstocks into useful organic compounds such as proteins and amino acids in heterotrophic fermentation systems. However, there are significant drawbacks for these systems. Heterotrophic fermentations are vulnerable to contamination because other heterotrophic microorganisms that can grow on fixed carbon nutrients and compete with a production strain are ubiquitous in the immediate environment. Heterotrophic technologies also generally suffer limitations in terms of competition with current modes of food production because you are essentially using a food source to make another food source. This can lead to numerous negative environmental impacts.

In addition to the need for new protein and other nutrient sources for feeding animals, that in turn are either consumed, or kept as pets, or otherwise utilized by humankind, there is a need for alternative protein and other nutrient sources for direct consumption by humans. One area where this need is particularly pressing, is in the area of human space flight, which requires a life-support system that supplies the crew's needs—$O_2$, $H_2O$, and food—and eliminates their wastes—$CO_2$, sewage, and heat. Food supplies represent a major source of weight and volume on longer missions. There is a need for life support systems that will operate for longer periods without resupply. An essential requirement for such systems is the ability to convert human and cabin waste products into useful products such as oxygen, potable water, food, and consumables. There is a need for food production that is edible as grown, and which lends itself to extended reliable automated growth and harvesting. The power penalty of biological systems is an important factor. There is a need for biological systems that efficiently utilize reliable nuclear and/or solar power systems.

Chemoautotrophic microorganisms represent a little explored alternative to photosynthetic organisms for use in carbon fixation processes that can address many of the unmet needs described above, while avoiding the limitations of photosynthesis described herein, while still leveraging billions of years of enzymatic evolution for catalyzing carbon-fixation reactions and synthesis from C1 feedstocks. The chemosynthetic reactions performed by chemoautotrophs for the fixation of $CO_2$, and other forms of inorganic carbon, to organic compounds, is powered by potential energy stored in inorganic chemicals, rather than by the radiant energy of light [Shively et al. (1998) Annu. Rev. Microbiol. 52:191-230; Smith et al. (1967) J Bacteriol 94(4): 972-983; Hugler et al. (2005) J Bacteriol 187(9): 3020-27; Scott and Cavanaugh (2007) Applied and Environmental Microbiology 73(4):1174-79]. Carbon fixing biochemical pathways that occur in chemoautotrophs include the reductive tricarboxylic acid cycle, the Calvin-Benson-Bassham cycle [Shively et al. supra, van Kaulen, et al. (1998) Annu. Rev. Microbiol., 191-230], and the Wood-Ljungdahl pathway [Ljungdahl (1986) 40:415-50; Lee, et al. (2008) Biotechnology and Bioengineering 101(2): 209-228; Fischer, et al. (2008) Metabolic Engineering 10:295-304]. Chemoautotrophic microorganisms are generally microbes that can perform $CO_2$ fixation, like in the photosynthetic dark reaction, but which can uptake the reducing agents needed for $CO_2$ fixation from an inorganic external source, rather than having to internally generate them through the photosynthetic light reaction. An energy harvesting step corresponding to the photosynthetic light reaction must still occur, but it can utilize an abiotic process, such as, for example, harvesting light energy with a photovoltaic or solar thermal technology.

Chemoautotrophic organisms are particularly well suited for hybrid chemical/biological processes for the conversion of $CO_2$-to-organic chemicals where the biological step is limited to $CO_2$ fixation alone. This $CO_2$-fixation steps corresponds roughly to the dark reaction that occurs in photosynthesis. This hybrid chemical/biological approach has received far less attention than more traditional heterotrophic or photosynthetic bioprocesses for the production of bio-based products. However, there are a number of potential advantages of such a hybrid approach including the ability to efficiently combine enzymatic capabilities gained through billions of years of evolution in fixing $CO_2$, with a wide array of abiotic energy conversion technologies such as solar PV, solar thermal, wind, geothermal, hydroelectric, or nuclear, in order to efficiently and cleanly power the overall biochemical production process from $CO_2$ carbon source. Furthermore, microorganisms performing carbon fixation without direct light requirements, in such a hybrid process, can be contained in more controlled and protected environments, less prone to water and nutrient loss, contamination, or weather damage, than what can be practically used for culturing photosynthetic microorganisms. An increase in bioreactor capacity can be more readily met with vertical rather than horizontal construction, making it potentially far more land efficient. A hybrid chemical/biological system offers the possibility of $CO_2$-to-organic molecule processes that avoid many drawbacks of photosynthesis while retaining the biological capabilities for complex and diverse organic synthesis from $CO_2$ and other simple inorganic inputs.

There are previously described applications of chemoautotrophic microorganisms in the capture and conversion of $CO_2$ gas to fixed carbon. However, many of these approaches have suffered shortcomings that have limited their effectiveness, economic feasibility, practicality and commercial adoption.

There is a need to break the bottleneck associated with significantly increasing agricultural outputs sustainably, on a very large scale. There is a need for biological production with compact, vertical scaling as opposed to traditional agricultural operations that scale horizontally and are highly land and water intensive. There is a need to mitigate the food versus nature conflict, and conflicts over land use, and the disruption of natural habitats.

Gas-to-chemical (GTC) technologies offer the benefit of allowing the utilization of waste carbon sources in the production of organic molecules. Such potential waste sources include: highly lignocellulosic waste—through the conversion to synthesis gas (syngas) via gasification; and waste $CO_2$, captured from industrial flue gases for example, through the provision of dihydrogen. Syngas is a mix of gases that generally contains $H_2$, CO, and $CO_2$ as major components, which can be generated through steam reforming of methane and/or liquid petroleum gas or biogas or through gasification of any organic, flammable, carbon-based material, including but not limited to biomass, waste organic matter, various polymers, peat, and coal. Many gasification processes are available for the production of syngas. A number of gasification processes subject the carbon-based feedstock to partial oxidation at high temperatures (500-1500° C.), with the oxygen supply restricted to prevent complete combustion, producing syngas with varying composition depending on feedstock and reaction conditions such that the ratio of $H_2$:CO can range from 0.5:1 to 3:1. The hydrogen component of syngas can be raised, and/or the CO component lowered, through the reaction of CO with steam in the water gas shift reaction with a concomitant increase in $CO_2$ in the syngas mix.

Some major technologies for syngas conversion to chemicals include chemical catalytic processes such as the Fischer-Tropsch (F-T) as well as processes for the synthesis of methanol or other mixed alcohols, the Haber-Bosch reaction for the production of ammonia and urea, and biological syngas fermentation processes.

Using syngas and/or $CO_2$ and/or renewable $H_2$ in a gas bioprocess creates the opportunity to utilize cheaper and more flexible and more scalable sources of energy and/or carbon for the biological synthesis of sustainable chemicals and fuels than is possible through heterotrophic or phototrophic biosynthesis. In a syngas bioprocess, syngas acts as both a carbon and energy source for the microbial culture.

A bioprocess based upon a gaseous feedstock such as syngas can allow for far lower negative environmental and food production impacts in the biological synthesis of organic compounds than highly land and water intensive heterotrophic or phototrophic-based technologies. However, current biological GTL and GTC technologies generally yield relatively short chain alcohols, or other short chain organic compounds, as primary products. None of these current biological conversions produce commercially competitive amino acids, proteins, and other biological nutrients.

The syngas-consuming microorganisms used in current biological GTC technologies are generally poorly suited for the synthesis of mid- to long-carbon chain molecules, such as most amino acids, proteins, and other biological nutrients.

While the abiotic synthesis of amino acids and peptides from simple C1 and inorganic precursors such as $H_2$, $CO_2$, CO, $H_2O$, $NH_3$, $CH_4$, $CH_3OH$, HCOH, is known, such approaches are currently non-competitive in comparison with biological methods for supplying protein or protein derivatives for the diet of humans, animals, and other heterotrophs. Challenges hindering the physicochemical, abiotic approach include low yields and side reactions yielding potentially toxic co-products.

There is a need to identify a set of microorganisms that can grow in conventional and scalable contained reaction vessels and that produce commercially viable sets of organic carbon chains, in particular over four carbon atoms long in a commercially feasible method. There is a need to identify microorganisms not limited metabolically by typical fixed carbon inputs such as sugar, and microorganisms that can additionally utilize syngas, producer gas, and also a wide array of abiotic sources of carbon and energy, directed through a $H_2/CO_2$ gas mix intermediate, for the synthesis of drop-in molecules. This will lead to a feedstock flexibility that far exceeds comparable heterotrophic systems. There is a need to identify and use microorganisms that can utilize electron donors such as hydrogen, present in syngas, producer gas, and also readily generated through a wide array of abiotic renewable and/or low-$CO_2$ emission energy technologies, for growth and carbon fixation.

There is a need for a biological means of producing amino acids, proteins, and other biological nutrients from low-cost or sustainable feedstocks. There is a need for a bioprocess that converts low cost syngas and/or $CO_2$ into higher value organic chemicals including but not limited to amino acids, proteins, and other biological nutrients.

SUMMARY OF THE INVENTION

In response to a need in the art that the inventors have recognized in making the invention, a system for the production of organic chemicals including but not limited to amino acids, proteins, and other biological nutrients from low-cost and sustainable feedstocks is presented herein. In some embodiments, the invention can couple the efficient production of these high value organic compounds with the disposal of waste sources of carbon and/or with the capture of $CO_2$, which can generate additional revenue and/or social value.

The present invention allows the use of naturally occurring or engineered microorganisms to convert $CO_2$ gas and/or syngas and/or producer gas and/or methane to higher value mid- to long-carbon chain length amino acids, proteins, and other biological nutrients. The present technology allows the development of new natural or classically bred and/or genetically enhanced strains of microorganisms that can be used for syngas bioprocessing within biological gas-to-chemical (GTC) processes to produce and/or secrete various relatively long chain organic compounds that are drop-in, and are currently only produced in bulk from higher plant agricultural crops or animal sources.

The present invention relates to the selection and/or breeding and/or engineering of microorganisms, including but not limited to hydrogen-oxidizing, carbon monoxide-oxidizing, and knallgas microorganisms, with a natural capability to grow and synthesize biomass on gaseous carbon sources such as syngas and/or $CO_2$, such that the production microorganisms synthesize targeted chemical products under gas cultivation. The microorganisms and methods of the present invention can enable low cost synthesis of biochemicals, which can compete on price with petrochemicals and higher-plant derived amino acids, proteins, and other biological nutrients. In certain embodiments, these amino acids, proteins, and other biological nutrients are predicted to have a substantially lower price than amino acids, proteins, and other biological nutrients produced through heterotrophic or microbial phototrophic synthesis.

The invention relates to a composition comprising a microorganism that converts syngas and/or gaseous $CO_2$ and/or a mixture of $CO_2$ gas and $H_2$ gas along with a nitrogen source including but not limited to ammonia, ammonium, and/or urea, into one or more amino acids, proteins, and other biological nutrients. In some embodiments, the composition comprises a microorganism, wherein the microorganism is one or more of the following: a hydrogen-oxidizing chemoautotrophic microorganism; a carbon monoxide-oxidizing microorganism; a knallgas microorganism. Knallgas microbes, hydrogenotrophs, carboxydotrophs, and chemoautotrophs more broadly, are able to capture $CO_2$ or CO as their sole carbon source to support biological growth. In some embodiments, this growth includes the biosynthesis of amino acids and proteins. Knallgas microbes and other hydrogenotrophs can use $H_2$ as a source of reducing electrons for respiration and biochemical synthesis. In some embodiments of the present invention knallgas organisms and/or hydrogenotrophs and/or carboxydotrophs and/or other chemoautotrophic microorganisms are grown on a stream of gasses including but not limited to one or more of the following: $CO_2$; CO; $H_2$; along with inorganic minerals dissolved in aqueous solution. In some embodiments knallgas microbes and/or hydrogenotrophs and/or carboxydotrophs and/or other chemoautotrophic and/or methanotrophic microorganisms convert greenhouse gases (GHG's) into biomolecules including amino acids and proteins.

In certain embodiments of the present invention, well known drawbacks of photosynthetic systems for capture and conversion of $CO_2$ such as those based on algae or higher plants are circumvented, while the unique biological capability, evolved over billions of years, for complex organic synthesis from $CO_2$ to produce valuable biochemicals such as but not limited to amino acids and proteins, is still leveraged.

In some embodiments, the composition comprises a microorganism, wherein the microorganism is chosen from the genera *Rhodococcus* or *Gordonia*. In some embodiments, the composition comprises a microorganism, wherein the microorganism is *Rhodococcus opacus*. In some embodiments, the composition comprises a microorganism, wherein the microorganism is *Rhodococcus opacus* (DSM 43205) or *Rhodococcus* sp. (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some non-limiting embodiments, the strain of *Cupriavidus necator* is DSM 531 or DSM 541.

In one aspect, a natural or engineered microorganism is provided that is capable of converting a gaseous substrate such as producer gas or synthesis gas or another gas mixture that contains $H_2$ and $CO_2$, and/or CO, and/or $CH_4$ into amino acids, proteins, and other biological nutrients. The gaseous substrate is used by the microorganism as a carbon and/or energy source. In some embodiments, microorganisms that are capable of growing on a gaseous substrate are transformed with a polynucleotide that encodes a gene that is required for biosynthesis of an amino acid, protein, or other biological nutrient. In some embodiments, an amino acid, protein, other biological nutrient, or a whole cell product is recovered from the microbial cells or from a microbial growth medium. Producer gas, which may be used in the microbial growth processes described herein, may come from sources that include gasification of waste feedstock and/or biomass residue feedstock, or waste gas from industrial processes or steam reforming of natural gas or biogas.

In one aspect, a non-naturally occurring microorganism is provided that is capable of growing on a gaseous substrate as a carbon and/or energy source, and wherein the microorganism includes at least one exogenous nucleic acid. In some embodiments, the microorganism is a bacterial cell. For example, in some embodiments, the bacterial cell is a *Cupriavidus* sp. or *Ralstonia* sp., for example, but not limited to, *Cupriavidus necator*. In some non-limiting embodiments, the microorganism is *Cupriavidus necator* DSM 531 or DSM 541. In some non-limiting embodiments, the microorganism is *Ralstonia eutropha* N-1, DSM 13513.

In some embodiments, the gaseous substrate includes $CO_2$ as a carbon source. In some embodiments, the gaseous substrate includes $H_2$ and/or O2 as an energy source. In some embodiments, the gaseous substrate includes producer gas, syngas, or pyrolysis gas. In some embodiments, the gaseous substrate includes a mixture of gases, comprising $H_2$ and/or $CO_2$ and/or CO.

In some embodiments, the microorganism produces amino acids, proteins, and other biological nutrients when cultured in the presence of the gas substrate under conditions suitable for growth of the microorganism and production of bioproducts.

In some embodiments, an exogenous gene is encoded by a coding sequence in the non-naturally occurring microorganism that is carried on a broad-host-range plasmid. In some embodiments, the exogenous gene coding sequence is under the control of a non-native inducible promoter. In some embodiments, the inducible promoter is derived from the *E. coli* ara operon.

In some embodiments, the coding sequence (CDS) of the exogenous gene is codon optimized for expression in a microorganism of as described herein, for example, but not limited to a *Ralstonia* or *Cupriavidus* species, for example, *Cupriavidus necator*.

In another aspect, methods are provided for producing amino acids, proteins, and other biological nutrients using an engineered microorganism as described herein that is capable of growing on a gaseous substrate as a carbon and/or energy source, and that includes at least one exogenous nucleic acid. In some embodiments, a non-naturally occurring microorganism as described herein is cultured in a bioreactor that includes a gaseous substrate and a culture medium (e.g., a liquid growth medium) that includes other nutrients for growth and bioproduct production, under conditions that are suitable for growth of the microorganism, wherein the microorganism produces amino acids, proteins, and other biological nutrients.

In some embodiments, the gaseous substrate in the bioreactor includes $H_2$ and/or $CO_2$. In some embodiments, the gaseous substrate is producer gas, syngas, or pyrolysis gas. In some embodiments, the gaseous substrate is natural gas or biogas. In some embodiments, the gaseous substrate is derived from municipal solid waste, black liquor, agricultural waste, wood waste, stranded natural gas, biogas, sour gas, methane hydrates, tires, pet coke, sewage, manure, straw, lignocellulosic energy crops, lignin, crop residues, bagasse, saw dust, forestry residue, food waste, waste carpet, waste plastic, landfill gas, and/or lignocellulosic biomass.

In some embodiments, amino acids, proteins, and other biological nutrients are recovered from the culture medium. In some embodiments, the culture medium is a biphasic liquid medium that includes an aqueous phase and an organic phase, and amino acids, proteins, and/or other biological nutrients are recovered by extraction or reactive extraction in the organic phase.

In another aspect, microorganisms and methods for producing amino acids, proteins, and other biological nutrients are provided. In some embodiments, a natural or non-naturally occurring microorganism is provided that is capable of growing on a gaseous substrate as a carbon and/or energy source, wherein the microorganism includes zero or at least one exogenous nucleic acid, and wherein said microorganism biosynthesizes amino acids, proteins, and other biological nutrients. In some embodiments, a method is provided for producing amino acids, proteins, and other biological nutrients in a naturally or non-naturally occurring microorganism as described herein that is capable of growing on a gaseous substrate as a carbon and/or energy source, that includes zero or one or more exogenous nucleic acids, and that biosynthesizes amino acids, proteins, and other biological nutrients, including culturing the naturally or non-naturally occurring microorganism in a bioreactor that includes a gaseous substrate and a culture medium (e.g., a liquid growth medium) that includes other nutrients for growth and bioproduct production, under conditions that are suitable for growth of the microorganism and production of amino acids, proteins, and other biological nutrients, wherein the microorganism produces amino acids, proteins, and other biological nutrients.

In some embodiments, the microorganisms of the present invention are used to capture $CO_2$ from industrial flue gasses and produce a protein-rich biomass. In some embodiments, this protein-rich biomass is a commodity. In some embodiments, the protein-rich biomass is used as a single cell protein (SCP). In some embodiments, the protein-rich biomass is used as an aquaculture feed or in an aquaculture feed formulation or in a fertilizer. In some embodiments, the protein-rich biomass is used as a high-protein substitute for fishmeal used in aquaculture and/or other animal feed and/or plant fertilizer products. In some non-limiting embodiments, the present invention is used both for GHG reduction and to produce high-protein products for applications including but not limited to animal feed or replacements for fish meal, casein, whey, or soy meal.

In one aspect, a biological and chemical method is provided for the capture and conversion of an inorganic and/or organic molecules containing only one carbon atom, into organic molecules containing two or more carbon atoms produced through anabolic biosynthesis comprising: introducing inorganic and/or organic molecules containing only one carbon atom, into an environment suitable for maintaining chemoautotrophic microorganisms; introducing a gaseous substrate into an environment suitable for maintaining chemoautotrophic microorganisms; wherein the inorganic and/or organic molecules containing only one carbon atom are used as a carbon source by the microorganism for growth and/or biosynthesis; converting the inorganic and/or organic molecules containing only one carbon atom into the organic molecule products containing two or more carbon atoms within the environment via at least one chemosynthetic carbon-fixing reaction and at least one anabolic biosynthetic pathway contained within the chemoautotrophic microorganisms; wherein the chemosynthetic fixing reaction and anabolic biosynthetic pathway are at least partially driven by chemical and/or electrochemical energy provided by electron donors and electron acceptors that have been generated chemically and/or electrochemically and/or thermochemically and/or are introduced into the environment from at least one source external to the environment.

In some embodiments, said microorganism is a bacterial cell. In some embodiments, said microorganisms are knallgas microorganisms. In some embodiments, said microorganism is a *Cupriavidus* sp. or *Ralstonia* sp. In some embodiments, said microorganism is *Cupriavidus necator*. In some embodiments, the microorganisms include microorganisms selected from one or more of the following genera: *Cupriavidus* sp., *Rhodococcus* sp., *Hydrogenovibrio* sp., *Rhodopseudomonas* sp., *Hydrogenobacter* sp., *Gordonia* sp., *Arthrobacter* sp., *Streptomycetes* sp. *Rhodobacter* sp., and/or *Xanthobacter* sp.

In some embodiments, said gaseous substrate comprises $CO_2$ as a carbon source. In some embodiments, said gaseous substrate comprises $H_2$ and/or $O_2$ as an energy source. In some embodiments, said gaseous substrate comprises pyrolysis gas or producer gas or syngas. In some embodiments, said gaseous substrate comprises a mixture of gases, comprising $H_2$ and/or $CO_2$ and/or CO. In some embodiments, said gaseous substrate comprises $H_2$ and/or $CO_2$.

In some embodiments, said microorganism produces amino acids and/or protein and/or vitamins and/or biomass when cultured in the presence of the gas substrate under conditions suitable for growth of the microorganism and production of bioproducts. In some embodiments, amino acids and/or protein and/or vitamins and/or biomass is recovered from the culture medium.

In some embodiments, said microorganisms and/or nutrients produced by said microorganisms are used to feed or provide nutrition to one or more other organisms.

In some embodiments, said gaseous substrate is pyrolysis gas or producer gas or syngas. In some embodiments, said gaseous substrate is derived from municipal solid waste, black liquor, agricultural waste, wood waste, stranded natural gas, biogas, sour gas, methane hydrates, tires, pet coke, sewage, manure, straw, lignocellulosic energy crops, lignin, crop residues, bagasse, saw dust, forestry residue, food waste, waste carpet, waste plastic, landfill gas, kelp, seaweed, and/or lignocellulosic biomass.

In some embodiments, said electron donors and/or molecules containing only one carbon atom are generated through a thermochemical process acting upon organic matter comprising at least one of: gasification; pyrolysis; steam reforming; autoreforming. In some embodiments, said electron donors and/or organic molecules containing only one carbon atom are generated through methane steam reforming. In some embodiments, the ratio of hydrogen to carbon monoxide in the output gas from gasification and/or pyrolysis and/or autoreforming and/or steam reforming is adjusted using the water gas shift reaction prior to the gas being delivered to the microorganisms.

In some embodiments, said electron donors and/or electron acceptors are generated or recycled using renewable, alternative, or conventional sources of power that are low in greenhouse gas emissions, and wherein said sources of power are selected from at least one of photovoltaics, solar thermal, wind power, hydroelectric, nuclear, geothermal, enhanced geothermal, ocean thermal, ocean wave power, and tidal power.

In some embodiments, said electron donors and/or electron acceptors are generated using grid electricity during periods when electrical grid supply exceeds electrical grid demand, and wherein storage tanks buffer the generation of said electron donors and/or electron acceptor, and their consumption in the chemosynthetic reaction.

In some embodiments, molecular hydrogen acts as an electron donor and is generated via a method using at least one of the following: electrolysis of water; thermochemical splitting of water; electrolysis of brine; electrolysis and/or thermochemical splitting of hydrogen sulfide. In some embodiments, electrolysis of water for the production of hydrogen is performed using one or more of the following: Proton Exchange Membranes (PEM), liquid electrolytes such as KOH, alkaline electrolysis, Solid Polymer Electrolyte electrolysis, high-pressure electrolysis, high temperature electrolysis of steam (HTES). In some embodiments, thermochemical splitting of water for the production of hydrogen is performed using one or more of the following: the iron oxide cycle, cerium(IV) oxide-cerium(III) oxide cycle, zinc zinc-oxide cycle, sulfur-iodine cycle, copper-chlorine cycle, calcium-bromine-iron cycle, hybrid sulfur cycle.

In some embodiments, molecular hydrogen acts as an electron donor and is generated via electrochemical or thermochemical processes known to produce hydrogen with low- or no-carbon dioxide emissions including one or more of the following: carbon capture and sequestration (CCS) enabled methane steam reforming; CCS enabled coal gasification; the Kvormer-process and other processes generating a carbon-black product; CCS enabled gasification or pyrolysis of biomass; pyrolysis of biomass producing a biochar co-product.

In some embodiments, said electron donors include but are not limited to one or more of the following reducing agents: ammonia; ammonium; carbon monoxide; dithionite; elemental sulfur; hydrocarbons; hydrogen; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, phosphates, sulfates, or carbonates, in dissolved or solid phases; and conduction or valence band electrons in solid state electrode materials. In some embodiments, said electron acceptors comprise one or more of the following: carbon dioxide; oxygen; nitrites; nitrates; ferric iron or other transition metal ions; sulfates; or valence or conduction band holes in solid state electrode materials.

In some embodiments, the biological conversion step is preceded by one or more chemical preprocessing steps in which said electron donors and/or electron acceptors and/or carbon sources and/or mineral nutrients required by the microorganism, are generated and/or refined from at least one input chemical and/or are recycled from chemicals emerging from the carbon-fixing step and/or are generated from, or are contained within, waste streams from other industrial, mining, agricultural, sewage or waste generating processes.

In some embodiments, the organic chemical product includes compounds with carbon backbones that are five carbons or longer.

In some embodiments, a method is provided for producing amino acids and/or protein and/or vitamins and/or biomass, comprising culturing a microorganism as described herein in a bioreactor that comprises a gaseous substrate and a culture medium that comprises other nutrients for growth and bioproduct production, under conditions that are suitable for growth of the microorganism and production of amino acids and/or protein and/or vitamins and/or biomass, wherein said microorganism produces amino acids and/or protein and/or vitamins and/or biomass.

In some embodiments, at least one chemosynthetic reaction and at least one anabolic biosynthetic pathway results in the formation of biochemicals including at least one of: amino acids; peptides; proteins; lipids; polysaccharides; and/or vitamins.

In some embodiments, biomass and/or biochemicals are produced through the said at least one chemosynthetic reaction, and wherein the biomass and/or biochemicals have application as at least one of the following: as an organic carbon and/or nitrogen source for fermentations; as a nutrient source for the growth of other microbes or organisms; as a nutrient source or food ingredient for humans; as a feed for animals; as a raw material or chemical intermediate for manufacturing or chemical processes; as sources of pharmaceutical, medicinal or nutritional substances; as a fertilizer; as soil additives; and/or as soil stabilizers.

In some embodiments, the carbon and/or nitrogen source from the said chemosynthetic reaction is used in a fermentation to produce biochemicals including least one of: commercial enzymes, antibiotics, amino acids, protein, food, food ingredients; vitamins, lipids, bioplastics, polysaccharides, neutraceuticals, pharmaceuticals. In some embodiments, said feed for animals is used to feed one or more of: cattle, sheep, chickens, pigs, fish, shellfish, insects, invertebrates, coral. In some embodiments, said shellfish or coral is grown using nutrients biosynthesized from C1 sources, produce carbonate materials that sequester $CO_2$ into solid mineralized form having high albedo.

Various objects, features, aspects, and advantages of the present invention will become more apparent from the following detailed description of preferred embodiments of the invention, along with the accompanying drawings in which like numerals represent like components

BRIEF DESCRIPTION OF THE DRAWINGS

Non-limiting embodiments of the present invention will be described by way of example with reference to the accompanying figures, some of which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 7 shows the results of the growth of chemotrophic and oleaginous microorganisms on different carbon sources. Bacterial growth was measured using optical density (OD) detection at 650 nm after the indicated days (in parentheses). Media and growth conditions described in the Examples below. ND, not done.

FIG. 21 shows a schematic diagram of a two-liter glass fermenter system used to grow *Xanthobacter autotrophicus* strain DSM 432 on a mixture of $H_2$, $CO_2$, and $O_2$ gases as the sole source of energy and carbon for growth.

FIG. 22 shows the headplate of the bioreactor depicted in FIG. 21, schematically illustrated.

DETAILED DESCRIPTION

Figure 1:
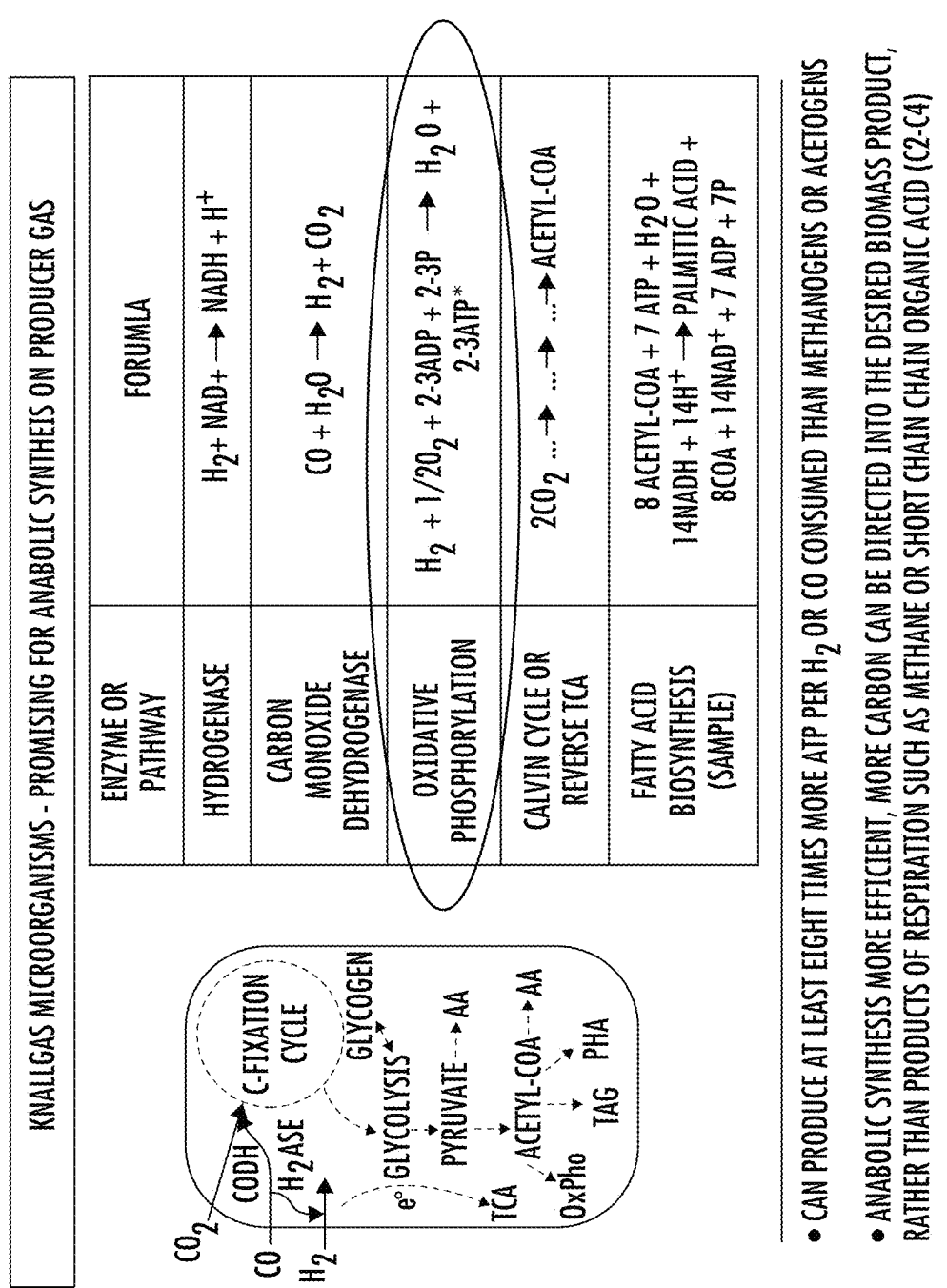
FIG. 1 shows metabolic pathways of knallgas microorganisms.

Provided herein are methods and systems for biosynthetic production of amino acids, proteins, and other biological nutrients. In certain embodiments, natural or engineered microorganisms are provided that produce amino acids, proteins, and other biological nutrients, on a gaseous substrate, including, but not limited to producer gas, syngas, tail gas, pyrolysis, knallgas, and gas mixtures containing $H_2$ and $CO_2$, and/or CO and/or $CH_4$. The gaseous substrate may serve as a carbon and/or energy source and/or a source of electron donors and/or electron acceptors for growth of the microorganisms and biosynthesis of bioproducts.

The inventive subject matter comprises, in certain embodiments, a wild-type or engineered microorganism capable of growing on syngas, or producer gas, and/or $H_2$, and/or $CO_2$, and/or CO, and/or $CH_4$, and/or other waste gases, which are capable of producing amino acids including but not limited to lysine and/or methionine.

In certain embodiments of the present invention amino acids, and/or peptides, and/or proteins and/or vitamins are synthesized from simple C1 and inorganic precursors including but not limited to one or more of the following: $H_2$, $CO_2$, CO, $H_2O$, $NH_3$, $CH_4$, $CH_3OH$, HCOH, urea.

In some embodiments, the invention relates to a method of producing one or more amino acids or proteins or vitamins, comprising exposing a bacterial cell to syngas and/or producer gas and/or gaseous $CO_2$ and/or $H_2$ and/or CO and/or CH4; wherein the bacterial cell is capable of fixing gaseous $CO_2$ and/or other C1 molecules into one or more amino acids or proteins or vitamins, and wherein the microorganism comprises zero or at least a first exogenous nucleic acid. In some embodiments, the cell utilizes the said gaseous substrates as a source of reducing equivalents and/or metabolic energy for the synthesis of one or more amino acids or proteins or vitamins. In some embodiments, the microorganism through its native machinery produces amino acids and/or proteins and/or vitamins.

In some embodiments, the invention relates to a method for producing amino acids and/or proteins and/or proteinaceous biomass and/or vitamins wherein the method comprises culturing natural strain or an engineered microorganism in a bioreactor or solution with a feedstock comprising syngas and/or producer gas and/or $CO_2$ and/or $H_2$ gas and/or CO and/or $CH_4$. [268] In some embodiments, the invention relates to a bioreactor comprising the composition or bacterial or microbial cells described herein. In some embodiments, the invention relates to a system for the production of one or more amino acids, proteins, or nutrients, comprising a bioreactor, which comprises: (a) a microorganism population comprising a cell described herein; and (b) an inlet connected to a feedstock source allowing delivery of a feedstock comprising syngas or producer gas and/or gaseous $CO_2$ and/or $H_2$ and/or CO and/or $CH_4$.

In another aspect of the invention, the invention relates to a method of producing a molecule or mixture of molecules in a microorganism population comprising the cell or the composition described herein, wherein the method comprises: culturing a population of microorganisms comprising the cell or the composition described herein in a feedstock comprising syngas or producer gas and/or gaseous $CO_2$ and/or $H_2$ and/or CO and/or $CH_4$. [270] In some embodiments the invention relates to a method of producing amino acids, or proteins, or other nutrients in a microorganism population comprising the cell of the composition described herein, wherein the method comprises: culturing a population of microorganisms comprising the cell or the composition described herein in a feedstock comprising syngas or producer gas and/or gaseous $CO_2$ and/or $H_2$ and/or CO and/or $CH_4$.

In some embodiments, the invention relates to a method of manufacturing one or more amino acids, or proteins, or other nutrients, comprising (a) culturing a cell described herein in a reaction vessel or bioreactor in the presence of syngas or producer gas and/or gaseous $CO_2$ and/or $H_2$ and/or CO and/or $CH_4$, wherein the cell produces and/or secretes one or more amino acids, or proteins, or other nutrients in a quantity equal to or greater than at least 10% of the cell's total dry cellular mass; and (b) separating the one or more amino acids, or proteins, or other nutrients, or a whole cell product from the reaction vessel. In some embodiments, the method further comprises purifying the one or more amino acids, or proteins, or other nutrients, or whole cell products after separation from the reaction vessel or bioreactor. In some embodiments, the one or more amino acids, or proteins, or other nutrients, or whole cell products are components of, or precursors to, or are included within a feed or nutrient supply or fertilizer provided to another organism. In certain non-limiting embodiments that other organism is a heterotroph, and in certain such embodiments an animal including but not limited to one or more of a: zooplankton, shellfish or other invertebrate, fish, bird, or mammal.

In some embodiments, the invention relates to a method of producing one or more amino acids comprising exposing a bacterial cell and/or archaeal cell and/or other microbial cell to syngas and/or gaseous $CO_2$ and/or $H_2$ and/or CO and/or $CH_4$; wherein the cell is capable of fixing gaseous $CO_2$ and/or other C1 carbon sources into one or more amino acids and/or proteins and/or vitamins; wherein the compounds are recovered from the bioreactor and fed to a second or more additional reactors and/or process steps wherein the compounds are post-processed to generate products including but not limited to one or more of the following: fertilizer, aquaculture feed, animal feed, human nutrition, or vitamins.

In some embodiments the present invention gives compositions and methods for the capture of carbon dioxide from carbon dioxide-containing gas streams and/or atmospheric carbon dioxide or carbon dioxide in dissolved, liquefied or chemically-bound form through a chemical and biological process that utilizes obligate or facultative chemoautotrophic microorganisms and particularly chemolithoautotrophic organisms, and/or cell extracts containing enzymes from chemoautotrophic microorganisms in one or more carbon fixing process steps. The present invention also gives compositions and methods for the recovery, processing, and use of the chemical products of chemosynthetic reactions performed by chemoautotrophs to fix inorganic carbon into organic compounds that are intermediate or finished chemicals, including but not limited to amino acids and/or protein and/or vitamins and/or biomass. The present invention also gives compositions and methods for the generation, processing and delivery of chemical nutrients needed for chemosynthesis and maintenance of chemoautotrophic cultures, including but not limited to the provision of electron donors and electron acceptors needed for chemosynthesis. The present invention also gives compositions and methods for the maintenance of an environment conducive for chemosynthesis and chemoautotrophic growth, and the recovery and recycling of unused chemical nutrients and process water.

In some embodiments, the microorganisms disclosed herein are recombinantly engineered to express one or more enzymes for biosynthetic production of amino acids, proteins, and other biological nutrients. In some embodiments, substrates or intermediates are diverted to the synthesis of amino acids, proteins, and/or other biological nutrients in the microbial cells, for example, acetyl-CoA, pyruvate, or malonyl-CoA. In some non-limiting embodiments, some fraction of carbon flux along the various biosynthesis pathways is directed into the biosynthesis of targeted amino acids, proteins, and other biological nutrients.

One feature of certain embodiments of the present invention is the inclusion of one or more process steps that utilize chemotrophic microorganisms and/or enzymes from chemotrophic microorganisms as a biocatalyst for the conversion of C1 chemicals into longer carbon chain organic molecules (i.e., C2 or longer and, in some embodiments, C5 or longer carbon chain molecules), within an overall process for the conversion of C1 carbon sources including but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks and/or methane feedstocks. In some such embodiments C1 containing syngas, or process gas, or C1 chemicals in a liquid form or dissolved in solution are pumped or otherwise added to a vessel or enclosure containing nutrient media and chemotrophic microorganisms. In some such cases chemotrophic microorganisms perform biochemical synthesis to elongate C1 chemicals into longer carbon chain organic chemicals using the carbon and electrons stored in the C1 chemical, and/or electrons and hydrogen from molecular hydrogen and/or valence or conduction electrons in solid state electrode materials and/or one or more of the following list of electron donors pumped or otherwise provided to the nutrient media, which include, but are not limited to one or more of the following: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases. The electron donors can be oxidized by electron acceptors in a chemosynthetic respiratory reaction. In certain embodiments, electron acceptors that are used for respiration by the microorganisms of the present invention include but are not limited to one or more of the following: oxygen, carbon dioxide, ferric iron or other transition metal ions, nitrates, nitrites, oxygen, or holes in solid state electrode materials. In certain non-limiting embodiments, the said chemotrophic microorganism is a knallgas or oxyhydrogen microorganism.

In certain embodiments the invention relates to chemotrophic bacterial strains that comprise zero or more exogenous nucleic acid sequences. The present invention arises in part from the discovery that chemotrophic bacteria and particular related microorganisms provide unforeseen advantages in the economic and large scale production of chemicals, proteins, feeds, fertilizers, monomers, oils, fuels, and other biological substances from gaseous and waste carbon feedstocks, and also from the discovery of genetic techniques and systems for modifying these microorganisms for improved performance in these applications. The proteins, lipids and other biochemicals synthesized by the microorganisms of the present invention can be applied to uses including but not limited to petrochemical substitutes, monomers, feedstock for the production of polymers, lubricants, as ingredients in fertilizer, animal feed, food, personal care, and cosmetic products. In some embodiments of the present invention enzymatic and chemical processes can be utilized to produce vitamins, amino acids, and/or proteins. Some embodiments enable the production of animal feeds and/or fertilizers. In addition, the present invention gives methods for culturing and/or modifying chemotrophic bacteria for improved amino acid and/or protein yield and/or lower production costs. In some embodiments, a genetically modified bacterium produces more of a certain type or types of vitamin or amino acid molecules as compared to the same bacteria that is not genetically modified.

The present invention relates to methods and mechanisms to confer production and/or secretion of carbon-based products of interest including but not limited to chemicals, monomers, polymers, amino acids, proteins, polysaccharides, vitamins, nutraceutical or pharmaceutical products or intermediates thereof in obligate or facultative chemotrophic organisms such that these organisms convert carbon dioxide and/or other forms of inorganic carbon and/or syngas and/or other C1 compounds such as methanol and/or the liquid, gaseous, and solid products of pyrolytic reactions such as pyrolysis gas and/or oil, into carbon-based products of interest, and in particular the use of such organisms for the commercial production of chemicals, monomers, polymers, amino acids, proteins, polysaccharides, vitamins, animal feeds, fertilizers, nutraceutical or pharmaceutical products or intermediates thereof.

In some embodiments the present invention also gives compositions and methods for chemical process steps that occur in series and/or in parallel with the chemosynthetic reaction steps that: convert unrefined raw input chemicals to more refined chemicals that are suited for supporting the chemosynthetic carbon fixing step; that convert energy inputs into a chemical form that can be used to drive chemosynthesis, and specifically into chemical energy in the form of electron donors and electron acceptors; that direct inorganic carbon captured from industrial or atmospheric or aquatic sources to the carbon fixation step or steps of the process under conditions that are suitable to support chemosynthetic carbon fixation; that further process the output products of the chemosynthetic carbon fixation steps into a form suitable for storage, shipping, and sale, with said products including but not limited to amino acids and/or proteins and/or vitamins and/or biomass. The fully chemical, abiotic, process steps combined with the biological chemosynthetic carbon fixation steps constitute the overall carbon capture and conversion process of the present invention. The present invention utilizes the unique ease of integrating chemoautotrophic microorganisms within a chemical process stream as a biocatalyst, as compared to other lifeforms. While not intending to be limited by theory, this unique capability and facility appears to arise from the fact that chemoautotrophs naturally act at the interface of biology and abiotic chemistry through their chemosynthetic mode of existence.

Unless defined otherwise herein, all technical and scientific terms used herein have the same meaning as commonly understood by one of ordinary skill in the art to which this invention belongs. Singleton, et al., Dictionary of Microbiology and Molecular Biology, second ed., John Wiley and Sons, New York (1994), and Hale & Markham, The Harper Collins Dictionary of Biology, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, Molecular Cloning: A Laboratory Manual, second edition (Sambrook et al., 1989); Oligonucleotide Synthesis (M. J. Gait, ed., 1984; Current Protocols in Molecular Biology (F. M. Ausubel et al., eds., 1994); PCR: The Polymerase Chain Reaction (Mullis et al., eds., 1994); and Gene Transfer and Expression: A Laboratory Manual (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates, thus the indefinite articles "a", "an,", and "the" as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The terms "amino acid" refer to a molecule containing both an amine group and a carboxyl group that are bound to a carbon, which is, designated the alpha-carbon. Suitable amino acids include, without limitation, both the D- and L-isomers of the naturally occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "Aufwuchs" (German for "surface growth" or "overgrowth") is the collection of small animals and plants that adhere to open surfaces in aquatic environments, such as parts of rooted plants. In both marine and freshwater environments, algae—particularly green algae and diatoms—make up the dominant component of aufwuchs communities. Small crustaceans, rotifers, and protozoans are also commonly found in fresh water and the sea, but insect larvae, oligochaetes and tardigrades are peculiar to freshwater aufwuchs faunas.

The term "biomass" refers to a material produced by growth and/or propagation of cells. Biomass may contain cells and/or intracellular contents as well as extracellular material, including, but not limited to, compounds secreted by a cell.

The term "bioreactor" or "fermenter" refers to a closed or partially closed vessel in which cells are grown and maintained. The cells may be, but are not necessarily held in liquid suspension. In some embodiments, rather than being held in liquid suspension, cells may alternatively be growing and/or maintained in contact with, on, or within another non-liquid substrate including but not limited to a solid growth support material.

The term "catalyst" refers to a chemical actor, such as a molecule or macromolecular structure, which accelerates the speed at which a chemical reaction occurs where a reactant or reactants is converted into a product or products, while the catalyst is not turned into a product itself, or otherwise changed or consumed at the completion of the chemical reaction. After a catalyst participates in one chemical reaction, because it is unchanged, it may participate in further chemical reactions, acting on additional reactants to create additional products. To accelerate a chemical reaction a catalyst decreases the activation energy barrier across the reaction path allowing it to occur at a colder temperature, or faster at a given temperature. In this way a more rapid approach of the system to chemical equilibrium may be achieved. Catalysts subsume enzymes, which are protein catalysts.

The term "cellulosic material" refers to any material with a high amount of cellulose, which is a polysaccharide having the formula $(C_6H_{10}O_5)_n$, that generally consists of a linear chain of hundreds to thousands of $\beta(1\rightarrow 4)$ linked D-glucose monomers. Sources of cellulosic material include but are not limited to cardboard, cotton, corn stover, paper, lumber chips, sawdust, sugar beet pulp, sugar cane bagasses, and switchgrass.

The term "CoA" or "coenzyme A" refers to an organic cofactor for condensing enzymes involved in fatty acid synthesis and oxidation, pyruvate oxidation, acetyl or other acyl group transfer, and in other acetylation.

The term "cofactor" subsumes all molecules needed by an enzyme to perform its catalytic activity. In some embodiments, the cofactor is any molecule apart from the substrate.

In the claims, as well as in the specification, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

The terms "exogenous gene" means a nucleic acid that has been recombinantly introduced into a cell, which encodes the synthesis of RNA and/or protein. In some embodiments, the exogenous gene is introduced by transformation. In some embodiments, the exogenous gene is introduced into the cell by electroporation. A transformed cell may be referred to as a recombinant cell, into which additional exogenous gene(s) may be introduced. The exogenous gene put into the host species may be taken from a different species (this is called heterologous), or it may naturally occur within the same species (this is homologous as defined below). Therefore, exogenous genes subsume homologous genes that are integrated within or introduced to regions of the genome, episome, or plasmid that differ from the locations where the gene naturally occurs. Multiple copies of the exogenous gene may be introduced into the cell. An exogenous gene may be present in more than one copy within the host cell or transformed cell. In some embodiments, the microorganism comprises between and including 1 and 10,000 copies of the nucleic acid that encodes an exogenous protein. In some embodiments, the microorganism comprises between and including 1 and 1,000 copies of the nucleic acid that encodes an exogenous protein. In some embodiments, the microorganism comprises between and including 1 and 10,000 copies of the nucleic acid that encodes an exogenous protein. In some embodiments, the microorganism comprises between and including 1 and 1,000 copies of the nucleic acid that encodes an exogenous protein. In some embodiments, the microorganism comprises between and including 1 and 500 copies of the nucleic acid that encodes an exogenous protein. In some embodiments, the exogenous gene is maintained by a cell as an insertion into the genome or as an episomal molecule. In some embodiments, the microorganism comprises no more than 1, 2, 3, 4, 5, 6, 7, 8, 9, 10, 20, 30, 40, 50, 60, 70, 80, 90, 100, or 1000 copies of the one or more nucleic acids that encode one or more exogenous proteins.

As used herein, the term "expressible form" refers to gene constructs that contain the necessary regulatory elements operably linked to a coding sequence that encodes an enzyme or fragment thereof capable of conferring enzymatic activity to a cell, such that when present in the cell, the coding sequence will be expressed. In some embodiments of the invention, the composition comprising the microorganisms or bacterial cells of the present invention comprise no more than ten expressible forms of exogenous nucleic acid sequences.

The term "lignocellulosic material" is any material composed of cellulose, hemicellulose, and lignin where the carbohydrate polymers (cellulose and hemicelluloses) are tightly bound to lignin. Lignocellulosic materials subsume agricultural residues (including corn stover and sugarcane bagasse), most biomass energy crops, wood residues (including sawmill and paper mill discards), and a substantial fraction of municipal waste.

The terms "lipids" refers to category of molecules that can be dissolved in nonpolar solvents (such as, but not limited to, chloroform and/or ether) and which also have low or no solubility in water. The hydrophobic character of lipid molecules typically results from the presence of long chain hydrocarbon sections within the molecule. Lipids subsume the following molecule types: hydrocarbons, fatty acids (saturated and unsaturated), fatty alcohols, fatty aldehydes, hydroxy acids, diacids, monoglycerides, diglycerides, triglycerides, phospholipids, sphingolipids, sterols such as cholesterol and steroid hormones, fat-soluble vitamins (such as vitamins A, D, E and K), polyketides, terpenoids, and waxes.

The term "lysate" refers to the liquid containing a mixture and/or a solution of cell contents that result from cell lysis. In some embodiments, the methods of the present invention comprise a purification of chemicals or mixture of chemicals in a cellular lysate. In some embodiments, the methods of the present invention comprise a purification of amino acids and/or protein in a cellular lysate.

The term "lysis" refers to the rupture of the plasma membrane and if present the cell wall of a cell such that a significant amount of intracellular material escapes to the extracellular space. Lysis can be performed using electrochemical, mechanical, osmotic, thermal, or viral means. In some embodiments, the methods of the present invention comprise performing a lysis of cells or microorganisms described herein in order to separate a chemical or mixture of chemicals from the contents of a bioreactor. In some embodiments, the methods of the present invention comprise performing a lysis of cells or microorganisms described herein, in order to separate an amino acid or mixture of amino acids and/or proteins from the contents of a bioreactor.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

"Periphyton" is a complex mixture of algae, cyanobacteria, heterotrophic microbes, and detritus that is attached to submerged surfaces in most aquatic ecosystems. It serves as an important food source for invertebrates, tadpoles, and some fish.

"Titer" refers to amount of a substance produced by a microorganism per unit volume in a microbial fermentation process. For example, biomass titer may be expressed as grams of biomass produced per liter of solution.

"Yield" refers to amount of a product produced from a feed material (for example, sugar) relative to the total amount of the substance that would be produced if all of the feed substance were converted to product. For example, amino acid yield may be expressed as % of amino acid produced relative to a theoretical yield if 100% of the feed substance were converted to amino acid.

"Productivity" refers to the amount of a substance produced by a microorganism per unit volume per unit time in a microbial fermentation process. For example, biomass productivity may be expressed as grams of biomass produced per liter of solution per hour.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides, which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to effect transcription, an optional operator sequence to control such transcription, a sequence encoding suitable mRNA ribosome binding sites, and sequences that control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "gene" refers to a DNA segment that is involved in producing a polypeptide and includes regions preceding and following the coding regions as well as intervening sequences (introns) between individual coding segments (exons).

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

The term "derived from" encompasses the terms "originated from," "obtained from," "obtainable from," "isolated from," and "created from," and generally indicates that one specified material finds its origin in another specified material or has features that can be described with reference to another specified material.

The term "culturing" refers to growing a population of cells, e.g., microbial cells, under suitable conditions for growth, in a liquid or solid medium.

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

As used herein, the terms "transformed," "stably transformed," and "transgenic" refer to a cell that has a non-native (e.g., heterologous or exogenous) nucleic acid sequence integrated into its genome or as an episomal plasmid that is maintained through multiple generations.

The terms "recovered," "isolated," "purified," and "separated" as used herein refer to a material (e.g., a protein, nucleic acid, or cell) that is removed from at least one component with which it is naturally associated. For example, these terms may refer to a material that is substantially or essentially free from components which normally accompany it as found in its native state, such as, for example, an intact biological system.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins. "Wild-type" in reference to a microorganism refers to a microorganism as it occurs in nature.

"Chemoautotrophic" refers to organisms that obtain energy by the oxidation of chemical electron donors by chemical electron acceptors and synthesize all the organic compounds needed by the organism to live and grow from carbon dioxide.

"Lithoautotrophic" refers to a specific type of chemoautotrophy where the organism utilizes the oxidation of inorganic chemical electron donors by inorganic chemical electron acceptors as an energy source.

The term "knallgas" refers to the mixture of molecular hydrogen and oxygen gas. A "knallgas microorganism" is a microbe that can use hydrogen as an electron donor and oxygen as an electron acceptor in respiration for the generation of intracellular energy carriers such as Adenosine-5'-triphosphate (ATP). The terms "oxyhydrogen" and "oxyhydrogen microorganism" can be used synonymously with "knallgas" and "knallgas microorganism" respectively. Knallgas microorganisms generally use molecular hydrogen by means of hydrogenases, with some of the electrons donated from $H_2$ being utilized for the reduction of $NAD^+$ (and/or other intracellular reducing equivalents) and some of the electrons from $H_2$ being used for aerobic respiration. Knallgas microorganisms generally fix $CO_2$ autotrophically, through pathways including but not limited to the Calvin Cycle or the reverse citric acid cycle ["Thermophilic bacteria", Jakob Kristjansson, Chapter 5, Section III, CRC Press, (1992)].

"Heterotrophic" refers to organisms that cannot synthesize all the organic compounds needed by the organism to live and grow from carbon dioxide, and which must utilize organic compounds for growth.

"Hydrogen-oxidizer" refers to microorganisms that utilize reduced $H_2$ as an electron donor for the production of intracellular reducing equivalents and/or in respiration.

"Acetogen" refers to microorganisms that generate acetate and/or other short chain organic acids up to C4 chain length as a product of anaerobic respiration.

"Methanogen" refers to a microorganism that generates methane as a product of anaerobic respiration.

"Methylotroph" refers to microorganisms that can use reduced one-carbon compounds, such as but not limited to methanol or methane, as a carbon source and/or as an electron donor for their growth.

"Extremophile" refers to microorganisms that thrive in physically or geochemically extreme conditions (e.g., high or low temperature, pH, or high salinity) compared to conditions on the surface of the Earth or the ocean typically tolerated by most life forms.

"Thermophile" refers to a type of extremophile that thrives at relatively high temperatures for life, between 45 and 122° C.

"Hyperthermophile" refers to a type of extremophile that thrives in extremely hot environments for life, from 60° C. (140° F.) upwards.

"Acidophile" refers to a type of extremophile that thrives under highly acidic conditions (usually at pH 2.0 or below).

"Halophile" refers to a type of extremophile that thrives in environments with very high concentrations of salt.

"Psychrophile" refers to a type of extremophile capable of growth and reproduction in cold temperatures, ranging from 10° C. and below.

"Producer gas" refers to gas mixture containing various proportions of $H_2$, CO, and $CO_2$, and having heat value typically ranging between one half and one tenth that of natural gas per unit volume under standard conditions. Producer gas can be generated various ways from a variety of feedstocks including gasification, steam reforming, or autoreforming of carbon-based feedstocks. In addition to $H_2$, CO, and $CO_2$, producer gases can contain other constituents including but not limited to methane, hydrogen sulfide, condensable gases, tars, and ash depending upon the generation process and feedstock. The proportion of $N_2$ in the mixture can be high or low depending upon if air is used as an oxidant in the reactor or not and if the heat for the reaction is provided by direct combustion or through indirect heat exchange.

"Syngas" or "Synthesis gas" refers to a type of gas mixture, which like producer gas contains $H_2$ and CO, but which has been more specifically tailored in terms of $H_2$ and CO content and ratio and levels of impurities for the synthesis of a particular type of chemical product, such as but not limited to methanol or fischer-tropsch diesel.

"Carbon source" refers to the types of molecules from which a microorganism derives the carbon needed for organic biosynthesis.

"Energy source" refers to either the electron donor that is oxidized by oxygen in aerobic respiration or the combination of electron donor that is oxidized and electron acceptor that is reduced in anaerobic respiration.

"Biphasic growth environment" refers to a growth environment containing two immiscible liquid phases.

The term "gasification" refers to a generally high temperature process that converts carbon-based materials into a mixture of gases including hydrogen, carbon monoxide, and carbon dioxide called synthesis gas, syngas or producer gas. The process generally involves partial combustion and/or the application of externally generated heat along with the controlled addition of oxygen and/or steam such that insufficient oxygen is present for complete combustion of the carbon-based material.

The term "hydrophobic" refers to matter that has low solubility in water and greater solubility in a hydrophobic phase than in an aqueous phase.

The terms "microorganism" and "microbe" mean microscopic single celled life forms, including but not limited to bacteria, fungi, and algae microorganisms.

The term "molecule" means any distinct or distinguishable structural unit of matter comprising one or more atoms, and includes for example hydrocarbons, lipids, polypeptides and polynucleotides.

The term "oleaginous" refers to something that is rich in oil or produces oil in high quantities.

The term "organic compound" refers to any gaseous, liquid, or solid chemical compounds which contain carbon atoms with the following exceptions that are considered inorganic: carbides, carbonates, simple oxides of carbon, cyanides, and allotropes of pure carbon such as diamond and graphite.

The term "precursor to" or "precursor of" is an intermediate towards the production of one or more of the components of a finished product.

The term "producing" includes both the production of compounds intracellularly and extracellularly, which is to include the secretion of compounds from the cell.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated.

Production of Amino Acids, Proteins, and Other Biological Nutrients from Gaseous Energy and Carbon Substrates In some embodiments natural or engineered microorganisms are provided that are capable of converting producer gas or a gas mixture containing $H_2$ and/or CO and/or $CO_2$ and/or $CH_4$ into amino acids, proteins, and other biological nutrients. In some embodiments, natural or engineered microorganisms are provided that are capable of converting producer gas or a gas mixture containing $H_2$ and/or CO and/or $CO_2$ and/or $CH_4$ into a vitamin. In certain embodiments that vitamin is a B vitamin including but not limited to one or more of the following: vitamin B1, B2, and/or B12.

The inventive subject matter comprises, in some embodiments, a natural microorganism capable of growing on syngas, and/or $H_2$ and $CO_2$, and/or CO, and/or $CH_4$, and/or other waste gases and which is capable of producing amino acids, proteins, and other biological nutrients using said gases as a growth substrate. The inventive subject matter comprises, in other embodiments, a natural microorganism capable of growing on syngas, and/or $H_2$ and $CO_2$, and/or CO, and/or $CH_4$, and/or other waste gases and capable of producing vitamin B1, vitamin B2, and/or vitamin B12 and/or other vitamins.

In some embodiments, the instant invention provides for a method of producing amino acids, proteins, and other biological nutrients including but not limited to vitamins, by combining, in a bioreactor or solution, a carbon-containing gas, and a natural or engineered strain microorganism that converts a carbon-containing gas such as syngas, producer gas, $CO_2$, carbon monoxide and/or mixtures of the same containing hydrogen gas; and/or C1 compounds, gaseous or liquid, including but not limited to methanol or methane, into amino acids, proteins, and/or other biological nutrients including but not limited to vitamins.

Producer gas used in some embodiments of the process may come from sources that include gasification of waste feedstock and/or biomass residue feedstock, or waste gas from industrial processes, or reforming of methane containing gases including by not limited to natural gas, biogas, landfill gas, stranded natural gas and/or flared natural gas. In some embodiments, methane may be converted to amino acids, proteins, and/or other biological nutrients including but not limited to vitamins, using engineered or natural microorganisms and methods described herein. In some embodiments of the present invention, the invention is utilized for the production of amino acids and/or proteins and/or vitamins in regions where natural gas prices are lowest, and where remote, and particularly "stranded" and flared natural gas is known to occur such as in the U.S., Middle East, western Africa, and Russia.

In some embodiments, the inventive subject matter comprises an engineered microorganism with one or more exogenous genes.

Chemoautotrophs are capable of performing chemosynthetic reactions that fix $CO_2$, and/or other forms of inorganic carbon, to organic compounds, using the potential energy stored in inorganic chemicals to drive the reaction, rather than radiant energy from light as in microorganisms performing photosynthesis [Shively et al. (1998) supra; Smith et al. (1967) supra; Scott and Cavanaugh (2007) supra]. Carbon fixing biochemical pathways that occur in chemoautotrophs include the reductive tricarboxylic acid cycle, the Calvin-Benson-Bassham cycle [Shively, et al. (1998) supra], and the Wood-Ljungdahl pathway [Ljungdahl (1986) supra; Lee, et al. (2008) supra; Fischer, et al. (2008) supra].

Certain non-limiting embodiments of the invention relate to a wild-type or genetically modified microorganism and compositions comprising such a microorganism, wherein the microorganism comprises zero or one or more exogenous genes and wherein the microorganism grows on carbon-containing gas or utilizes a gaseous feedstock selected from syngas, $CO_2$, $H_2$, CO, $CH_4$, or mixtures of gas comprising one or more gases selected from syngas, $CO_2$, $H_2$, CO, or $CH_4$.

In some embodiments, the microorganism of the inventive subject matter is selected from the *Ralstonia* microorganisms. In some embodiments, the microorganism is *Ralstonia eutropha*. In some embodiments, the microorganism is selected from *Cupriavidus* microorganisms. In some embodiments, the microorganism is *Cupriavidus necator*. In some embodiments, the microorganism is *Cupriavidus necator* DSM531 or DSM541. In some embodiments, the microorganism is selected from the genus *Hydrogenobacter*. In some embodiments, the microorganism is *Hydrogenobacter thermophilus*. In some embodiments, the microorganism contains the reverse tricarboxylic acid cycle (rTCA), also known as the reverse citric acid cycle or the reverse Krebs cycle. [See, e.g., Miura, A., Kameya, M., Arai, H., Ishii, M. & Igarashi, Y. A soluble NADH-dependent fumarate reductase in the reductive tricarboxylic acid cycle of *Hydrogenobacter thermophilus* TK-6. *J Bacteriol* 190: 7170-7177, doi:JB.00747-08 [pii] 10.1128/JB.00747-08 (2008).; Shively, et al. (1998) supra, which are incorporated herein by reference in their entireties.]

In some embodiments the microorganism is *Rhodococcus opacus* or *Rhodococcus jostii* or *Rhodococcus* sp. In some non-limiting embodiments, the microorganism is *Rhodococcus opacus* DSM 43205 and/or *Rhodococcus* sp. DSM 3346. In some embodiments, the natural or engineered strain includes but is not limited to hydrogen utilizing microbes including but not limited to the genera *Rhodococcus* or *Gordonia*, *Ralstonia* or *Cupriavidus*. In some embodiments, the composition comprises a microorganism wherein the microorganism can naturally grow on $H_2/CO_2$ and/or syngas, and wherein the microorganism can naturally accumulate lipid to 50% or more of the cell biomass by weight. In some embodiments, the microorganisms have a native ability to send a high flux of carbon down the fatty acid biosynthesis pathway. In some embodiments, the microorganism exhibiting these traits is *Rhodococcus opacus* (DSM 43205 or DSM 43206 or DSM 44193).

The invention relates to a cell and compositions comprising a cell of the class Actinobacteria comprising zero or one or more exogenous genes. The invention also relates to cells and compositions comprising cells of the family of Nocardiaceae comprising zero or one or more exogenous genes. The invention also relates to cells and compositions comprising cells of *Corynebacterium, Gordonia, Rhodococcus, Mycobacterium* and *Tsukamurella* comprising zero or one or more exogenous genes. In some embodiments, the invention relates to cells of the family of Nocardiaceae comprising zero or one or more exogenous genes, wherein the cell is not a cell of the genus *Mycobacterium*. In some embodiments, the invention provides a cell and compositions comprising a cell of the genus *Rhodococcus* comprising zero or one or more exogenous genes, and in some embodiments the cell is a strain of the species *Rhodococcus* sp., *Rhodococcus opacus, Rhodococcus aetherivorans; Rhodococcus aurantiacus; Rhodococcus baikonurensis; Rhodococcus boritolerans; Rhodococcus equi; Rhodococcus coprophilus; Rhodococcus corynebacterioides; Nocardia corynebacterioides* (synonym: *Nocardia corynebacterioides*); *Rhodococcus erythropolis; Rhodococcus fascians; Rhodococcus globerulus; Rhodococcus gordoniae; Rhodococcus jostii; Rhodococcus koreensis; Rhodococcus kroppenstedtii; Rhodococcus maanshanensis; Rhodococcus marinonascens; Rhodococcus opacus; Rhodococcus percolatus; Rhodococcus phenolicus; Rhodococcus polyvorum; Rhodococcus pyridinivorans; Rhodococcus rhodochrous; Rhodococcus rhodnii*; (synonym: *Nocardia rhodnii*); *Rhodococcus ruber* (synonym: *Streptothrix rubra*); *Rhodococcus* sp. RHA1; *Rhodococcus triatomae; Rhodococcus tukisamuensis; Rhodococcus wratislaviensis* (synonym: *Tsukamurella wratislaviensis*); *Rhodococcus yunnanensis*; or *Rhodococcus zopfii*. In some embodiments, the cell comprising zero or one or more exogenous genes is one or more of the following: strain *Rhodococcus opacus* DSM number 43205 or 43206; *Rhodococcus* sp. DSM number 3346. In some embodiments, the invention relates to a *Rhodococcus* cell or composition comprising a *Rhodococcus* cell, wherein the cell is not a species selected from *Rhodococcus equi* or *Rhodococcus fascians*.

In some embodiments the microorganism is from the suborder corynebacterineae or the family burkholderiaceae. In some embodiments, the cell or compositions comprising one of more cells is not *E. coli*. In some embodiments, the cell of the present invention is not pathogenic to animals or plants. In some embodiments, the cell of the present invention is not pathogenic to humans. In some embodiments, the cell or compositions comprising one of more cells is from the genus *Ralstonia*. In some embodiments, the cell or compositions comprising one of more cells is from the species *Ralstonia eutropha* or *Cupriavidus necator* or *Cupriavidus metallidurans*. In some embodiments, the cell comprising zero or one or more exogenous genes is strain *Cupriavidus necator* DSM number 531 or 541.

In some embodiments, the microorganism of the present invention can accumulate protein to over 60% and/or over 70% and/or over 80% of the total cell mass. In some non-limiting embodiments, the microorganism is *Cupriavidus necator* DSM number 531 or 541.

In some embodiments, the composition comprises a microorganism that can naturally grow on $H_2/CO_2$ and/or syngas, and wherein the microorganism can naturally accumulate polyhydroxybutyrate (PHB) or polyhydroxyalkanoate (PHA) to 50% or more of the cell biomass by weight. In some embodiments, the microorganisms have a native ability to direct a high flux of carbon through the acetyl-CoA metabolic intermediate, which can lead into fatty acid biosynthesis, along with a number of other synthetic pathways including PHA and PHB synthesis, as well as amino acids.

In some embodiments, the microorganism exhibiting these traits is *Cupriavidus necator* (DSM 531 or DSM 541).

In some embodiments the natural or engineered strain includes but is not limited to *Corynebacterium autotrophicum*. In some embodiments, the natural or engineered strain includes but is not limited to *Corynebacterium glutamicum*. In some embodiments, the microorganism is *Hydrogenovibrio marinus*. In some embodiments, the microorganism is *Rhodopseudomonas capsulata, Rhodopseudomonas palustris*, or *Rhodobacter sphaeroides*.

In some embodiments, the microorganism is an oxyhydrogen or knallgas strain. In some embodiments the microorganisms comprise one or more of the following knallgas microorganisms: *Aquifex pyrophilus, Aquifex aeolicus*, or other *Aquifex* sp.; *Cupriavidus necator, Cupriavidus metallidurans*, or other *Cupriavidus* sp.; *Corynebacterium autotrophicum* or other *Corynebacterium* sp.; *Gordonia desulfuricans, Gordonia polyisoprenivorans, Gordonia rubripertincta, Gordonia hydrophobica, Gordonia westfalica*, and other *Gordonia* sp.; *Nocardia autotrophica, Nocardia opaca*, or other *Nocardia* sp.; purple non-sulfur photosynthetic bacteria including but not limited to *Rhodobacter sphaeroides, Rhodopseudomonas palustris, Rhodopseudomonas capsulata, Rhodopseudomonas viridis, Rhodopseudomonas sulfoviridis, Rhodopseudomonas blastica, Rhodopseudomonas spheroides, Rhodopseudomonas acidophila* and other *Rhodopseudomonas* sp. and *Rhodobacter* sp.; *Rhodospirillum rubrum*, and other *Rhodospirillum* sp.; *Rhodococcus opacus* and other *Rhodococcus* sp.; *Rhizobium japonicum* and other *Rhizobium* sp.; *Thiocapsa roseopersicina* and other *Thiocapsa* sp.; *Pseudomonas facilis, Pseudomonas flava, Pseudomonas putida, Pseudomonas hydrogenovora, Pseudomonas hydrogenothermophila, Pseudomonas palleronii, Pseudomonas pseudoflava, Pseudomonas saccharophila, Pseudomonas thermophile*, and other *Pseudomonas* sp.; *Hydrogenomonas pantotropha, Hydrogenomonas eutropha, Hydrogenomonas facilis*, and other *Hydrogenomonas* sp.; *Hydrogenobacter thermophiles, Hydrogenobacter halophilus, Hydrogenobacter hydrogenophilus*, and other *Hydrogenobacter* sp.; *Hydrogenophilus islandicus* and other *Hydrogenophilus* sp.; *Hydrogenovibrio marinus* and other *Hydrogenovibrio* sp.; *Hydrogenothermus marinus* and other *Hydrogenothermus* sp.; *Helicobacter pylori* and other *Helicobacter* sp.; *Xanthobacter autotrophicus, Xanthobacter flavus* and other *Xanthobacter* sp.; *Hydrogenophaga flava, Hydrogenophaga palleronii, Hydrogenophaga pseudoflava* and other *Hydrogenophaga* sp.; *Bradyrhizobium japonicum* and other *Bradyrhizobium* sp.; *Ralstonia eutropha* and other *Ralstonia* sp.; *Alcaligenes eutrophus, Alcaligenes facilis, Alcaligenes hydrogenophilus, Alcaligenes latus, Alcaligenes paradoxus, Alcaligenes ruhlandii* and other *Alcaligenes* sp.; *Amycolata* sp.; *Aquaspirillum autotrophicum* and other *Aquaspirillum* sp.; *Arthrobacter* strain 11/X, *Arthrobacter methylotrophus*, and other *Arthrobacter* sp.; *Azospirillum lipoferum* and other *Azospirillum* sp.; *Variovorax paradoxus*, and other *Variovorax* sp.; *Acidovorax facilis*, and other *Acidovorax* sp.; *Bacillus schlegelii, Bacillus tusciae* and other *Bacillus* sp.; *Calderobacterium hydrogenophilum* and other *Calderobacterium* sp.; *Derxia gummosa* and other *Derxia* sp.; *Flavobacterium autothermophilum* and other *Flavobacterium* sp.; *Microcyclus aquaticus* and other *Microcyclus; Mycobacterium gordoniae* and other *Mycobacterium* sp.; *Paracoccus denitrificans* and other *Paracoccus* sp.; *Persephonella marina, Persephonella guaymasensis* and other *Persephonella* sp.; *Renobacter vacuolatum* and other *Renobacter* sp.; *Streptomycetes coelicoflavus, Streptomycetes gri-*

*seus, Streptomycetes xanthochromogenes, Streptomycetes thermocarboxydus*, and other *Streptomycetes* sp.; *Thermocrinis ruber* and other *Thermocrinis* sp.; *Wautersia* sp.; cyanobacteria including but not limited to *Anabaena oscillarioides, Anabaena spiroides, Anabaena cylindrica*, and other *Anabaena* sp., and *Arthrospira platensis, Arthrospira maxima* and other *Arthrospira* sp.; green algae including but not limited to *Scenedesmus obliquus* and other *Scenedesmus* sp., *Chlamydomonas reinhardii* and other *Chlamydomonas* sp., *Ankistrodesmus* sp., *Rhaphidium polymorphium* and other *Rhaphidium* sp; as well as a consortiums of microorganisms that include oxyhydrogen microorganisms.

In some non-limiting embodiments the invention relates to compositions comprising and methods of using chemoautotrophic metabolism to produce ATP for the support of ATP consuming biosynthetic reactions and cellular maintenance, without the co-production of methane or short chain organic acids such as acetic or butyric acid, by means of energy conserving reactions for the production of ATP, which use inorganic electron donors and electron acceptors, including but not limited to the oxyhydrogen reaction.

A number of different microorganisms have been characterized that are capable of growing on carbon monoxide as an electron donor and/or carbon source (i.e. carboxydotrophic microorganisms). In some cases, carboxydotrophic microorganisms can also use $H_2$ as an electron donor and/or grow mixotrophically. In some cases, the carboxydotrophic microorganisms are facultative chemolithoautotrophs. [Biology of the Prokaryotes, edited by J Lengeler, G. Drews, H. Schlegel, John Wiley & Sons, Jul. 10, 2009, incorporated herein by reference in its entirety.] In some embodiments the microorganisms comprise one or more of the following carboxydotrophic microorganisms: *Acinetobacter* sp.; *Alcaligenes carboxydus* and other *Alcaligenes* sp.; *Arthrobacter* sp.; *Azomonas* sp.; *Azotobacter* sp.; *Bacillus schlegelii* and other *Bacillus* sp.; *Hydrogenophaga pseudoflava* and other *Hydrogenophaga* sp.; *Pseudomonas carboxydohydrogena, Pseudomonas carboxydovorans, Pseudomonas compransoris, Pseudomonas gazotropha, Pseudomonas thermocarboxydovorans* and other *Pseudomonas* sp.; *Rhizobium japonicum* and other *Rhizobium* sp.; *Streptomyces G26 Streptomyces thermoautotrophicus* and other *Streptomyces* sp. In certain embodiments of the present invention a carboxydotrophic microorganism is used. In certain embodiments, a carboxydotrophic microorganism that is capable of chemolithoautotrophy is used. In certain embodiments, a carboxydotrophic microorganism that is able to use $H_2$ as an electron donor in respiration and/or biosynthesis is used.

In some embodiments the microorganisms comprise obligate and/or facultative chemoautotrophic microorganisms including one or more of the following: *Acetoanaerobium* sp.; *Acetobacterium* sp.; *Acetogenium* sp.; *Achromobacter* sp.; *Acidianus* sp.; *Acinetobacter* sp.; *Actinomadura* sp.; *Aeromonas* sp.; *Alcaligenes* sp.; *Alcaligenes* sp.; *Aquaspirillum* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfurosarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanococcoides* sp.; *Methanogenium* sp.; *Methanolobus* sp.; *Methanomicrobium* sp.; *Methanoplanus* sp.; *Methanosarcina* sp.; *Methanospirillum* sp.; *Methanothermus* sp.; *Methanothrix* sp.; *Micrococcus* sp.; *Nitrobacter* sp.; *Nitrobacteraceae* sp., *Nitrococcus* sp., *Nitrosococcus* sp.; *Nitrospina* sp., *Nitrospira* sp., *Nitrosolobus* sp.; *Nitrosomonas* sp.; *Nitrosospira* sp.; *Nitrosovibrio* sp.; *Nitrospina* sp.; *Oleomonas* sp.; *Paracoccus* sp.; *Peptostreptococcus* sp.; *Planctomycetes* sp.; *Pseudomonas* sp.; *Ralstonia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Siderococcus* sp.; *Streptomyces* sp.; *Sulfobacillus* sp.; *Sulfolobus* sp.; *Thermothrix* sp., *Thiobacillus* sp.; *Thiomicrospira* sp.; *Thioploca* sp.; *Thiosphaera* sp.; *Thiothrix* sp.; *Thiovulum* sp.; sulfur-oxidizers; hydrogen-oxidizers; iron-oxidizers; acetogens; and methanogens; consortiums of microorganisms that include chemoautotrophs; chemoautotrophs native to at least one of hydrothermal vents, geothermal vents, hot springs, cold seeps, underground aquifers, salt lakes, saline formations, mines, acid mine drainage, mine tailings, oil wells, refinery wastewater. coal seams, deep sub-surface; waste water and sewage treatment plants; geothermal power plants, sulfatara fields, and soils; and extremophiles selected from one or more of thermophiles, hyperthermophiles, acidophiles, halophiles, and psychrophiles.

Such organisms also include but are not limited to extremophiles that can withstand extremes in various environmental parameters such as temperature, radiation, pressure, gravity, vacuum, desiccation, salinity, pH, oxygen tension, and chemicals. They include hyperthermophiles, such as *Pyrolobus fumarii*; thermophiles, such as *Synechococcus lividis*; mesophiles, and psychrophiles, such as *Psychrobacter*. Extremely thermophilic sulfur-metabolizers such as *Thermoproteus* sp., *Pyrodictium* sp., *Sulfolobus* sp., *Acidianus* sp. Radiation tolerant organisms include *Deinococcus radiodurans*. Pressure tolerant organisms include piezophiles or barophiles. Desiccant tolerant and anhydrobiotic organisms include xerophiles; microbes and fungi. Salt tolerant organisms include halophiles, such as Halobacteriacea and *Dunaliella salina*. pH tolerant organisms include alkaliphiles such as Natronobacterium, *Bacillus firmus* OF4, *Spirulina* spp., and acidophiles such as *Cyanidium caldarium, Ferroplasma* sp. Gas tolerant organisms, which tolerate pure $CO_2$ include *Cyanidium caldarium* and metal tolerant organisms include metalotolerants such as *Ferroplasma acidarmanus, Ralstonia* sp.

In some embodiments, the invention further provides a composition wherein the microorganism is a hydrogen-oxidizing chemoautotroph and/or a carboxydotroph and/or a methylotroph and/or methanotroph. In some embodiments, the invention further provides a composition wherein the microorganism is capable of growing on syngas and/or producer gas and/or pyrolysis gas as the sole electron donor, and/or source of reduced hydrogen atoms, and/or carbon source. In some embodiments, the invention further provides a composition wherein the microorganism is capable of growing on untreated crude glycerol as the sole electron donor, and/or source of reduced hydrogen atoms, and/or carbon source.

In certain embodiments of the present invention the microbes used are naturally occurring and/or non-genetically modified (non-GMO) microorganisms and/or non-pathogenic and/or rely on specific environmental conditions provided by the bioprocesses that are absent from the surrounding environment.

Certain embodiments of the present invention utilize a microorganism or consortium of microorganisms, isolated from environmental samples and enriched with desirable microorganisms using methods known in the art of microbiology through growth in the presence of targeted electron donors including but not limited to one or more of: hydrogen and/or CO and/or syngas and/or methane, and electron acceptors including but not limited to one or more of oxygen and/or nitrate and/or ferric iron and/or $CO_2$, and environmental conditions (e.g. temperature, pH, pressure, DO, salinity, the presence of various impurities and pollutants etc.).

In some embodiments, the invention further provides a method wherein the electron donors utilized in biosynthesis and/or respiration include but are not limited to one or more of the following reducing agents: ammonia; ammonium; carbon monoxide; dithionite; elemental sulfur; hydrogen; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite.

In some embodiments the microorganism is a methanotroph. In some embodiments, the microorganism is in the genus *Methylococcus*. In some embodiments, the microorganism is *Methylococcus capsulatus*. In some embodiments, the microorganism is a methylotroph. In some embodiments, the microorganism is in the genus *Methylobacterium*. In some embodiments, the microorganism is drawn from one or more of the following species: *Methylobacterium zatmanii; Methylobacterium extorquens; Methylobacterium chloromethanicum*.

In some embodiments the microorganism of the claimed invention is not dependent upon light to grow and/or to synthesize one or more of the following: amino acids and/or proteins and/or other nutrients. In some embodiments, the microorganism of the claimed invention does not require any type of sugar or any other type of organic compound or any type of fixed carbon to grow and/or to synthesize one or more of the following: amino acids and/or proteins and/or other nutrients. In some embodiments, the microorganism of the claimed invention is a facultative microorganism.

The production of organic molecules with carbon chain lengths longer than C4 is most commonly and efficiently accomplished biologically through anabolic biosynthesis pathways such as fatty acid biosynthesis [Fischer, Klein-Marcuschamer, Stephanolpoulos, *Metabolic Engineering* (2008) 10, 295-304], and various amino acid biosynthetic pathways. The initial molecule entering into the fatty acid biosynthesis pathway is acetyl-coenzyme A (acetyl-CoA), a central metabolite from which many high value biochemicals can be derived. In some embodiments, the invention utilizes microorganisms with a naturally occurring pathway for the conversion of CO, $CO_2$ and/or $H_2$ and/or $CH_4$ to acetyl-CoA. In some embodiments, the invention utilizes microorganisms that can fix CO and/or $CO_2$ through the reductive tricarboxylic acid cycle, the Calvin-Benson-Bassham cycle, and/or the Wood-Ljungdahl pathway. In some embodiments, the invention utilizes microorganisms the fix C1 compounds through a methanotrophic pathway. In some embodiments the microorganisms naturally produce enzymes that catalyze the fixation of gaseous inorganic carbon to produce one or more of acetyl-CoA, pyruvate, malonyl-CoA, utilizing gaseous electron donors such as are present in syngas and/or producer gas as reducing agents, with such enzymatic proteins including but not limited to acetyl-CoA synthase, acetyl-CoA synthase disulfide reductase, cobalamide corrinoid/iron-sulfur protein, carbon monoxide dehydrogenase, hydrogenase, and methyltransferase.

Unlike methanogenic, acetogenic and solventogenic pathways, present in methanogens and acetogens respectively, which can produce short chain organic compounds (C1-C4) with net ATP production or zero net consumption (i.e., ATP neutral), anabolic biosynthetic pathways such as fatty acid synthesis involve net ATP consumption. For example, the following gives the net reaction for synthesis of Palmitic acid (C16) starting from Acetyl-CoA:

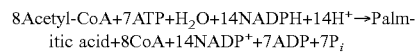

A drawback with using an obligate methanogen or acetogen in a GTC process for the production of molecules made via anabolic biosynthesis, such as amino acids, proteins, or lipids, is the obligate use of $CO_2$ as an electron acceptor in respiration for the production of ATP, which is needed for anabolic biosynthesis such as fatty acid synthesis or amino acid synthesis. If $H_2$ is the electron donor, the ATP produced per $H_2$ consumed for respiration in an acetogen or methanogen is relatively low: one ATP per $4H_2$ for the respiratory production of methane [Thauer, R. K., Kaster, A. K., Seedorf, H., Buckel, W. & Hedderich, R. Methanogenic archaea: ecologically relevant differences in energy conservation. *Nat Rev Microbiol* 6, 579-591, doi:nrmicro1931 [pii], is incorporated herein by reference in its entirety.] or acetic acid production, and one ATP per $10H_2$ for butyric acid production. [Papoutsakis, *Biotechnology & Bioengineering* (1984) 26, 174-187; Heise, Muller, Gottschalk, J. *Bacteriology* (1989) 5473-5478; Lee, Park, Jang, Nielsen, Kim, Jung, *Biotechnology & Bioengineering* (2008) 101(2) 209-228, which are incorporated herein by reference in their entireties.]

In some embodiments, the invention relates to a microorganism or compositions comprising a microorganism, wherein the microorganism is able to produce ATP from an inorganic electron donor such as but not limited to $H_2$ and/or CO without the synthesis of methane or short chain organic acids (short chain organic acids comprising carbon chain lengths from two to four carbons long). In some non-limiting embodiments, the invention relates to a microorganism or compositions comprising a microorganism, wherein the microorganism produces ATP from an inorganic electron donor such as but not limited to $H_2$ and/or CO, coupled with an electron acceptor other than $CO_2$ that is used in respiration.

Certain embodiments of the present invention apply hydrogen-oxidizing and/or CO-oxidizing and/or $CH_4$ oxidizing microorganisms that use more electronegative electron acceptors in energy conserving reactions for ATP production, such as but not limited to $O_2$. For example, hydrogenotrophic oxyhydrogen or knallgas microbes that couple the oxyhydrogen reaction, $2H_2+O_2 \rightarrow 2\ H_2O$, to ATP production, can produce more ATP per $H_2$ and/or other electron donor consumed for respiration, than acetogens or methanogens that use $CO_2$ as an electron acceptor in respiration. For example, knallgas microorganisms can produce at least two ATP per $H_2$ consumed in respiration [Bongers, *J. Bacteriology*, (October 1970) 145-151, is incorporated herein by reference in its entirety.], which is eight times more ATP produced per $H_2$ consumed in respiration than what can be produced in microorganisms undergoing methanogenesis or acetogenesis, using $H_2$ as electron donor and $CO_2$ as electron acceptor in respiration. For this reason, using microorganisms that can utilize more electronegative electron acceptors in respiration and in the production of ATP, such as but not limited to knallgas microbes, for anabolic biosynthesis such as but not limited to amino acid or protein or fatty acid biosynthesis from syngas or H2, can be more efficient than using acetogens or methanogens, such as those which are currently used in biological GTC technologies.

In certain embodiments, the oxyhydrogen reaction used in respiration is enzymatically linked to oxidative phosphorylation. In certain embodiments, the ATP and/or other intracellular energy carriers thus formed are utilized in the anabolic synthesis of amino acids and/or proteins. In some embodiments, the invention relates to a knallgas microorganism or compositions comprising a knallgas microorganism, wherein the microorganism comprises at least zero or one or more exogenous nucleic acid sequences that encodes zero or more enzymes to enable biosynthesis of useful carbon-based products of interest including but not limited to chemicals, monomers, polymers, proteins, polysaccharides, vitamins, nutraceuticals, antibiotics, or pharmaceutical products or intermediates thereof from a carbon-containing gas feedstock, including but not limited to syngas or producer gas or waste $CO_2$ combined with renewable $H_2$ or CO or methane containing gases. In some non-limiting embodiments, the invention relates to a microorganism or compositions comprising a microorganism, wherein the microorganism requires less than $4H_2$ to produce one ATP through respiration. In other non-limiting embodiments, the invention relates to a microorganism or compositions comprising a microorganism, wherein the microorganism produces more than one ATP per $H_2$ consumed through respiration. In other non-limiting embodiments, the invention relates to a microorganism or compositions comprising a microorganism, wherein the microorganism produces at least two ATP per $H_2$ consumed through respiration, or at least 2.5 ATP per $H_2$ consumed through respiration.

In some embodiments, the invention relates to a composition comprising a microorganism that converts syngas and/or producer gas and/or gaseous $CO_2$ and/or $H_2$ and/or CO and/or $CH_4$ into one or more organic compounds, wherein less than 10% by weight of the organic compounds produced by the microorganism is methane. In some embodiments, the invention relates to a composition comprising a microorganism that converts said gaseous substrates into one or more organic compounds; wherein less than 10% by weight of the organic compounds produced are free organic acids with carbon chain length of four carbons or less.

In certain embodiments of the present invention the microorganism reduces $CO_2$, producing cell material and $H_2O$. In certain embodiments, the energy needed for the metabolic pathways that perform this reduction is obtained by the oxidation of hydrogen with molecular oxygen. In certain embodiments of the present invention the biological system and/or components function directly as a $CO_2$ reducer, but not an $O_2$ producer. In certain embodiments, the $O_2$ utilized in respiration is obtained from another system and provided to the biological system and/or components. In certain embodiments that other system involves the electrolysis and/or thermolysis of water.

An advantage of using oxyhydrogen microorganisms over strictly anaerobic acetogenic or methanogenic microorganisms for carbon capture applications and/or syngas conversion applications is the higher oxygen tolerance of oxyhydrogen microorganisms. In some embodiments of the invention a microorganism is utilized which tolerates aerobic and/or microaerobic conditions. Oxyhydrogen microorganisms generally have an advantage over strict anaerobic acetogenic or methanogenic microorganisms for carbon capture applications from a flue gas due to the higher oxygen tolerance of oxyhydrogen microorganisms. Since industrial flue gas is one intended source of $CO_2$ for certain embodiments of the present invention, the relatively high oxygen tolerance of oxyhydrogen microorganisms, as compared with obligately anaerobic methanogens or acetogens, can allow the $O_2$ content of 2-6% found in typical fluegas to be better tolerated. In certain embodiments of the present invention a 2% or greater $O_2$ content in a $CO_2$ containing flue gas, or any other type of input gas mixture, is tolerated by the microbial culture and/or utilized in microbial respiration.

A further advantage of using oxyhydrogen microorganisms for carbon capture applications and/or syngas conversion applications over using acetogens is that the production of ATP through respiration powered by the oxyhydrogen reaction results in a water product, which can readily be incorporated into the process stream, rather than the generally undesirable acetic acid or butyric acid products of acidogenesis, which can harm the microorganisms by dropping the solution pH or accumulating to inhibitory or toxic levels. In some embodiments of the invention the primary product of cellular respiration is water.

In some embodiments, the microorganism is capable of growing on untreated crude glycerol and/or glucose and/or methanol and/or acetate as the sole electron donor, and carbon source. In some embodiments, the microorganism is able to grow mixotrophically on an organic carbon source and using inorganic electron donor or carbon source.

In certain embodiments, microorganisms provided by the invention comprises a cell line selected from eukaryotic plants, algae, cyanobacteria, green-sulfur bacteria, green non-sulfur bacteria, purple sulfur bacteria, purple non-sulfur bacteria, extremophiles, yeast, fungi, proteobacteria, engineered organisms thereof, and synthetic organisms. In certain embodiments *Spirulina* is utilized.

In certain embodiments purple non-sulfur bacteria are used which include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira*.

The liquid cultures used to grow cells associated with the invention can be housed in any of the culture vessels known and used in the art. In some embodiments, large scale production in a bioreactor vessel can be used to produce large quantities of a desired molecule and/or biomass.

Another advantage of certain embodiments of the present invention relates to the bioreactor vessels used to contain, isolate, and/or protect the culture environment. Exemplary culture vessels that can be used in some non-limiting embodiments of the present invention to culture and grow microorganisms for production of organic compounds including but not limited to one or more of the following: amino acids, proteins, and other nutrients; include those that are known to those of ordinary skill in the art of large scale microbial culturing. Such culture vessels, that may be used in certain embodiments of the present invention include but are not limited to one or more of the following: airlift reactors; biological scrubber columns; bubble columns; stirred tank reactors; continuous stirred tank reactors; counter-current, upflow, expanded-bed reactors; digesters and in particular digester systems such as known in the prior arts of sewage and waste water treatment or bioremediation; filters including but not limited to trickling filters, rotating biological contactor filters, rotating discs, soil filters; fluidized bed reactors; gas lift fermenters; immobilized cell reactors; loop reactors; membrane biofilm reactors; pachuca tanks; packed-bed reactors; plug-flow reactors; static mixers; trickle bed reactors; and/or vertical shaft bioreactors. The vessel base, siding, walls, lining, and/or top in certain embodiments can be constructed out of one or more materials including but not limited to bitumen, cement, ceramics, clay, concrete, epoxy, fiberglass, glass, macadam, plastics, sand, sealant, soil, steels or other metals and their alloys, stone, tar, wood, and any combination thereof. In certain embodiments of the present invention where the microorganisms either require a corrosive growth environment and/or produce corrosive chemicals through the carbon-fixation reaction, corrosion resistant materials known in the art and engineering field can be used to line the interior of the container contacting the growth medium.

Microbial culturing in the present invention in certain embodiments is performed for the sake of implementing genetic modifications, and/or for production of organic compounds, and particularly in certain embodiments, one or more of the following: amino acids, proteins, and other nutrients. Microbial culturing with the aim of genetic manipulation is generally performed at a small benchtop scale and often under conditions that select for genetically modified traits.

Microbial culturing aimed at the commercial production of organic compounds and specifically amino acids, protein, and other nutrients is typically performed in bioreactors at much greater scale (e.g., 500 L, 1,000 L 5,000 L, 10,000 L, 50,000 L, 100,000 L, 1,000,000 L bioreactor volumes and higher). In certain embodiments chemoautotrophs of the present invention are grown in a liquid media inside a bioreactor using the methods of the invention. In some embodiments, the bioreactor containing the microorganisms is constructed of opaque materials that keep the culture in near or total darkness. Bioreactors constructed out of opaque materials such as steel and/or other metallic alloys and/or reinforced concrete and/or fiberglass and/or various high strength plastic materials can be designed to have large working volumes. In some embodiments of the present invention fermenters constructed of steel or other metallic alloys that are 50,000 liters and greater in volume are utilized. In some embodiments of the present invention bioreactors able to contain positive headspace pressures above ambient pressure are utilized. In some embodiments of the present invention egg-shape or cylindrical digesters or vertical shaft bioreactors 3,000,000 liters and greater in volume are utilized. In some embodiments, the bioreactor comprising the microorganism does not allow light to penetrate part or most or all of its contained liquid volume. In some embodiments, the bacterial cell or microbial cell is cultured without significant or any exposure to light. In certain embodiments, converting electricity to light is not required.

Following the methods of the present invention, in some embodiments the microorganisms are grown and maintained for the production of amino acids, or proteins, or other nutrients, or whole cell products in a medium containing a gaseous carbon source, such as but not limited to syngas or producer gas or tail gas or pyrolysis gas or H2 and CO2 gas mixtures, in the absence of light; where such growth is known as chemoautotrophic growth. In some embodiments, the invention relates to methods of cultivating cells for the large-scale production of amino acids, or proteins, or other nutrients, or whole cell products. In some embodiments, the invention relates to methods of cultivating cells in bioreactors 50,000 liters or greater in volume, which are conventionally constructed out of low cost, sturdy, and opaque materials such as steel or other metallic alloys or reinforced concrete or earthworks. The size, depth, and construction of such bioreactors dictate that the cells will be grown in near or total darkness. In some embodiments, the microorganisms are cultured for the synthesis of amino acids, or proteins, or other nutrients, or whole cell products in accordance with the methods of the present invention in a medium containing gaseous inorganic carbon as the primary or sole carbon source, and without any exposure to light. This type of growth is known as chemoautotrophic growth. In certain non-limiting embodiments, the microorganism used in the $CO_2$-fixation step is not photosynthetic. In certain non-limiting embodiments, the bioreactor design does not confine the culture in thin layers, or have transparent walls, so as to make light available throughout the vessel, as is generally necessary with photosynthetic microorganisms.

In some embodiments of the present invention, the ability of chemoautotrophs to derive the energy needed for growth directly from redox chemistry rather than sunlight, while consuming $CO_2$ facilitates and/or enables continuous $CO_2$ capture operations, day and night, year-round, in all weather conditions, without the need for any artificial lighting. In contrast, algae and higher plants can become net $CO_2$ emitters during night or at low-light levels. Because of the lack of light requirement in certain embodiments of the present invention, conventional, proven equipment and infrastructure drawn from commercial bioprocesses that are constructed out of opaque materials, non-transparent to visible light, are applied in certain embodiments of the present invention without the need for any artificial lighting. In certain embodiments of the present invention an increase in system capacity is met by vertical scaling, rather than only scaling horizontally. This is in contrast to phototrophic approaches using algae, cyanobacteria, or higher-plants for $CO_2$ capture. Although various vertical farming schemes have been proposed for photosynthetic systems, practically and economically speaking, phototrophic systems must expand horizontally, for example in shallow ponds or photobioreactors in the case of algae. This results in large geographic footprints and many negative environmental impacts.

In cases, such as vertical farming, where artificial lighting would be otherwise be required to grow a photosynthetic organism such as algae or higher plants, in certain vertical farming-like embodiments of the present invention, converting electricity to light is not required for $CO_2$ conversion. In certain non-limiting embodiments of the present invention, electrolysis of water is substituted for the conversion of electricity to light, in supporting autotrophic $CO_2$ uptake and biosynthesis. In certain non-limiting embodiments of the present invention there is a large energy efficiency advantage in the conversion of electricity to electron donors such as, but not limited to, hydrogen through electrolysis, over the conversion of electricity to light. An algal or higher plant system grown with artificial lighting is challenged by inefficient utilization of light energy by the algae, and by inefficient conversion of electrical energy to light energy. In certain embodiments of the present invention, a comparable, in terms of $CO_2$ capture and/or biomass production, algal or high-plant culture grown under artificial lighting, will require more electrical power than the $CO_2$ capture and/or biomass production system of the present invention. In certain embodiments of the present invention, a comparable, in terms of $CO_2$ capture and/or biomass production, algal or higher-plant culture grown under artificial lighting, will require at least ten times more electrical power than the $CO_2$ capture and/or biomass production system of the present invention. For algae or higher-plants grown on artificial lighting the heat rejection requirement is almost in direct proportion to the electrical input. In certain embodiments of the present invention, the heat rejection requirements are lower than for a comparable algal, or higher plant system, in terms of $CO_2$ capture and/or biomass production grown on artificial lighting. In certain embodiments of the present invention, the heat rejection requirements are at least ten times lower than for a comparable algal, or higher plant system, in terms of $CO_2$ capture and/or biomass production, grown on artificial lighting.

In certain embodiments of the present invention, a relatively high tolerance for inclement conditions provided by the isolation of the bioprocess from the surrounding environment, enables the bioprocess of the present invention to operate in conditions unfavorable to open algal systems or traditional agriculture. In certain non-limiting embodiments of the present invention, low temperatures in winter are used to reduce process cooling costs incurred because the reaction of $H_2$ and $CO_2$ to produce protein is exothermic.

To give an illustration of the application of a bioreactor in certain embodiments of the present invention, a bioreactor containing nutrient medium is inoculated with production cells. Generally, there will follow a lag phase prior to the cells beginning to double. After the lag phase, the cell doubling time decreases and the culture goes into the logarithmic phase. The logarithmic phase is eventually followed by an increase of the doubling time that, while not intending to be limited by theory, is thought to result from either a mass transfer limitation, depletion of nutrients including nitrogen or mineral sources, or a rise in the concentration of inhibitory chemicals, or quorum sensing by the microbes. The growth slows down and then ceases when the culture goes into the stationary phase. In certain embodiments, there is an arithmetic growth phase preceding the stationary phase. In order to harvest cell mass the culture in certain embodiments is harvested in the logarithmic phase and/or the arithmetic phase and/or in the stationary phase. The accumulation of lipids can generally be triggered by the depletion of the nitrogen source or another key nutrient excepting the carbon or the electron source (e.g., hydrogen). In a number of species this signals the cells to store lipids produced from the excess carbon and energy sources.

The bioreactor or fermenter is used to culture cells through the various phases of their physiological cycle. A bioreactor is utilized for the cultivation of cells, which may be maintained at particular phases in their growth curve. The use of bioreactors is advantageous in many ways for cultivating chemoautotrophic growth. For certain embodiments, protein-rich cell mass, which is used to produce proteins or animal feeds, is grown to high densities in liquid suspension. Generally, the control of growth conditions including control of dissolved carbon dioxide, oxygen, and other gases such as hydrogen, as well as other dissolved nutrients, trace elements, temperature and pH, is facilitated in a bioreactor.

In some embodiments process conditions are used to enhance the effect on biosynthesis of native or expressed enzymes. In some embodiments, the process condition used to enhance the effect on the native or expressed enzymes is temperature.

Nutrient media as well as gases can be added to the bioreactor as either a batch addition, or periodically, or in response to a detected depletion or programmed set point, or continuously over the period the culture is grown and/or maintained. For certain embodiments, the bioreactor at inoculation is filled with a starting batch of nutrient media and/or gases at the beginning of growth, and no additional nutrient media and/or gases are added after inoculation. For certain embodiments, nutrient media and/or gases are added periodically after inoculation. For certain embodiments, nutrient media and/or gas is added after inoculation in response to a detected depletion of nutrient and/or gas. For certain embodiments, nutrient media and/or gas is added continuously after inoculation. For certain embodiments, the added nutrient media does not contain any organic compounds.

In certain embodiments inoculation of the culture into the bioreactor is performed by methods including but not limited to transfer of culture from an existing culture inhabiting another bioreactor, or incubation from a seed stock raised in an incubator. In certain embodiments, the seed stock of the strain may be transported and stored in forms including but not limited to a powder, liquid, frozen, or freeze-dried form as well as any other suitable form, which may be readily recognized by one skilled in the art. In certain non-limiting embodiments, the reserve bacterial cultures are kept in a metabolically inactive, freeze-dried state until required for restart. In certain embodiments when establishing a culture in a very large reactor, cultures are grown and established in progressively larger intermediate scale vessels prior to inoculation of the full-scale vessel.

For certain embodiments the bioreactors have mechanisms to enable mixing of the nutrient media that include but are not limited to one or more of the following: spinning stir bars, blades, impellers, or turbines; spinning, rocking, or turning vessels; gas lifts, sparging; recirculation of broth from the bottom of the container to the top via a recirculation conduit, flowing the broth through a loop and/or static mixers. The culture media may be mixed continuously or intermittently.

In certain embodiments the microorganism containing nutrient medium may be removed from the bioreactors of the present invention partially or completely, periodically or continuously, and in certain embodiments is replaced with fresh cell-free medium to maintain the cell culture in certain embodiments in an exponential growth phase and/or to replenish the depleted nutrients in the growth medium and/or remove inhibitory waste products.

The ports that are standard in bioreactors may be utilized to deliver, or withdraw, gases, liquids, solids, and/or slurries, into and/or from the bioreactor vessel enclosing the microbes of the present invention. Many bioreactors have multiple ports for different purposes (e.g. ports for media addition, gas addition, probes for pH and DO, sampling), and a given port may be used for various purposes during the course of a fermentation run. As an example, a port might be used to add nutrient media to the bioreactor at one point in time and at another time might be used for sampling. Preferably, the multiple use of a sampling port can be performed without introducing contamination or invasive species into the growth environment. A valve or other actuator enabling control of the sample flow or continuous sampling can be provided to a sampling port. For certain embodiments, the bioreactors are equipped with at least one port suitable for culture inoculation that can additionally serve other uses including the addition of media or gas. Bioreactor ports enable control of the gas composition and flow rate into the culture environment. For example, the ports can be used as gas inlets into the bioreactor through which gases are pumped.

For some embodiments gases that may be pumped into a bioreactor include but are not limited to one or more of the following: syngas, producer gas, pyrolysis gas, hydrogen gas, CO, $CO_2$, $O_2$, air, air/$CO_2$ mixtures, natural gas, biogas, methane, ammonia, nitrogen, noble gases, such as argon, as well as other gases. In some embodiments the $CO_2$ pumped into the system may come from sources including but are not limited to: $CO_2$ from the gasification of organic matter; $CO_2$ from the calcination of limestone, $CaCO_3$, to produce quicklime, $CaO$; $CO_2$ from methane steam reforming, such as the $CO_2$ byproduct from ammonia, methanol, or hydrogen production; $CO_2$ from combustion, incineration, or flaring; $CO_2$ byproduct of anaerobic or aerobic fermentation of sugar; $CO_2$ byproduct of a methanotrophic bioprocess; $CO_2$ from waste water treatment; $CO_2$ byproduct from sodium phosphate production; geologically or geothermally produced or emitted $CO_2$; $CO_2$ removed from acid gas or natural gas. In certain embodiments, the carbon source is $CO_2$ and/or bicarbonate and/or carbonate in sea water or other bodies of surface or underground water. In certain embodiments, the carbon source is $CO_2$ from the atmosphere. In certain non-limiting embodiments, the $CO_2$ has been captured from a closed cabin as part of a closed-loop life support system, using equipment such as but not limited to a $CO_2$ removal assembly (CDRA), which is utilized on the International Space Station (ISS).

In certain embodiments of the present invention, carbon dioxide containing flue gases are captured from a smoke stack at temperature, pressure, and gas composition characteristic of the untreated exhaust, and directed with minimal modification into the reaction vessels where carbon-fixation occurs. In some embodiments in which impurities harmful to organisms are not present in the flue gas, modification of the flue gas upon entering the reaction vessels can be limited to the compression needed to pump the gas through the reactor system and/or the heat exchange needed to lower the gas temperature to one suitable for exposure to the microorganisms. In certain embodiments, the $CO_2$ present in a flue gas or other mixed gas stream is purified and/or concentrated prior to introduction into the bioreactor using carbon-capture technologies and processes well known in the art.

In embodiments in which carbon dioxide bearing flue gas is transported through a system for dissolving the carbon dioxide into solution (such as is well known in the art of carbon capture and/or microbial conversion), the scrubbed flue gas with reduced $CO_2$ content, (which generally primarily includes inert gases such as nitrogen), can in certain embodiments be released into the atmosphere.

In certain embodiments of the present invention the carbon source is $CO_2$ and/or CO contained in industrial flue or off-gases and/or from natural sources including but not limited to geological and geothermal sources. In certain embodiments, the $CO_2$ and/or CO containing flue and/or off gases utilized are emitted from one or more of the following industries or sectors: oil; electricity; natural gas; cement; chemicals; steel; metallurgy; fermentation; waste water treatment. In certain non-limiting embodiments of the present invention a relatively small land-footprint, facilitates collocation of the bioprocess with industrial facilities producing $CO_2$ and/or other carbon wastes including but not limited to one or more of the following: fossil power plants; oil refineries; tar sands upgrading facilities; natural gas or petroleum drilling operations; ethanol distilleries; cement manufactures; aluminum manufactures, chloroalkali manufactures, steel foundries; geothermal power plants. In certain embodiments of the present invention waste-heat associated with industrial flue-gas sources is further utilized in the production process of the present invention for steps including but not limited to in biomass drying.

In certain embodiments gases in addition to carbon dioxide, or in place of carbon dioxide as an alternative carbon source, are either dissolved into solution and fed to the culture broth and/or dissolved directly into the culture broth including but not limited to gaseous electron donors and/or carbon sources (e.g., hydrogen and/or CO and/or methane gas). In certain embodiments of the present invention, input gases may include other electron donors and/or electron acceptors and/or carbon sources and/or mineral nutrients such as but not limited to other gas constituents and impurities of syngas (e.g., hydrocarbons); ammonia; hydrogen sulfide; and/or other sour gases; and/or $O_2$; and/or mineral containing particulates and ash.

In certain embodiments of the present invention gases are dissolved into the culture broth of the present invention including but not limited to gaseous electron donors such as but not limited to one or more of the following: hydrogen, carbon monoxide, methane, hydrogen sulfide or other sour gases; gaseous carbon sources such as but not limited to one or more of the following $CO_2$, CO, $CH_4$; and electron acceptors such as but not limited to oxygen, either within air (e.g. 20.9% oxygen) or as pure $O_2$ or as an $O_2$-enriched gas. In some embodiments, the dissolution of these and other gases into solution is achieved using a system of compressors, flowmeters, and flow valves known to one skilled in the art of fermentation engineering, that feed into one of more of the following widely used systems for dispersing gas into solution: sparging equipment; diffusers including but not limited to dome, tubular, disc, or doughnut geometries; coarse or fine bubble aerators; venturi equipment. In certain embodiments of the present invention surface aeration and/or gas mass transfer may also be performed using paddle aerators and the like. In certain embodiments of the present invention gas dissolution is enhanced by mechanical mixing with an impeller or turbine, as well as hydraulic shear devices to reduce bubble size. Following passage through the reactor system holding microorganisms which uptake the gases, in certain embodiments the residual gases may either be recirculated back to the bioreactor, or burned for process heat, or flared, or injected underground, or released into the atmosphere. In certain embodiments of the present invention utilizing $H_2$ as electron donor, $H_2$ may be fed to the culture vessel either by bubbling it through the culture medium, or by diffusing it through a hydrogen permeable-water impermeable membrane known in the art that interfaces with the liquid culture medium.

In certain embodiments the microorganisms grow and multiply on the $H_2$ and $CO_2$ and other dissolved nutrients under microaerobic conditions. In certain embodiments a C1 chemical such as but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, are biochemically converted into longer chain organic chemicals (i.e. C2 or longer and, in some embodiments, C5 or longer carbon chain molecules) under one or more of the following conditions: aerobic, microaerobic, anoxic, anaerobic, and/or facultative conditions.

A controlled amount of oxygen can also be maintained in the culture broth of some embodiments of the present invention, and in certain embodiments, oxygen will be actively dissolved into solution fed to the culture broth and/or directly dissolved into the culture broth. In certain aerobic or microaerobic embodiments of the present invention that require the pumping of air or oxygen into the culture broth in order to maintain targeted DO levels, oxygen bubbles may be injected into the broth at an optimal diameter for mixing and oxygen transfer. This has been reported to be 2 mm in the Environment Research Journal May/June 1999 pgs. 307-315. In certain aerobic embodiments of the present invention a process of shearing the oxygen bubbles may be used to achieve this bubble diameter as described in U.S. Pat. No. 7,332,077. In certain embodiments bubbles, larger than 7.5 mm average diameter and/or slugging are avoided.

In some embodiments, the inventive subject matter converts a fuel gas including but not limited to syngas, producer gas, pyrolysis gas, biogas, tailgas, fluegas, CO, $CO_2$, $H_2$, and mixtures thereof. In some embodiments, the heat content of the fuel gas is at least 100 BTU per standard cubic foot (scf). In some embodiments of the present invention, a bioreactor is used to contain and grow the microorganisms, which is equipped with fine-bubble diffusers and/or high-shear impellers for gas delivery.

In some embodiments oxygen is used as an electron acceptor in the respiration of the microorganism used for the biosynthesis of amino acids, or proteins, or other nutrients, or whole cell products. In some embodiments, strong electron acceptors including but not limited to $O_2$ are used to maximize efficiency and yield of products produced via anabolic pathways such as amino acids, fatty acids, or vitamins. A key challenge with using $O_2$ as an electron acceptor is keeping $O_2$ levels sufficiently adequate to allow aerobic microbes to grow well and efficiently generate anabolic products while also maintaining appropriate and safe levels of inflammable $H_2$ and $O_2$ mixtures, as well as other fuel gas/$O_2$ mixtures, in the bioreactor to minimize the risk of explosion. In some embodiments, custom or specialized reactor designs are used to control $O_2$ in the broth at a level that is optimal for the microbes while avoiding dangerous gas mixes. In some embodiments bioreactor designs are used that avoid dangerous mixtures of $H_2$ and $O_2$, while providing the microorganisms with necessary levels of these gases for cellular energy, carbon fixation, and for the production of amino acid, or protein, or other nutrients, or whole cells.

Introducing and/or raising the gas flow rate into a bioreactor can enhance mixing of the culture and produce turbulence if the gas inlet is positioned beneath the surface of the liquid media such that gas bubbles or sparges up through the media. In certain embodiments mixing is enhanced through turbulence provided by gas bubbles and/or sparging and/or gas plugging up through the liquid media. In some embodiments, a bioreactor comprises gas outlet ports for gas escape and pressure release. In some embodiments, gas inlets and outlets are preferably equipped with check valves to prevent gas backflow.

In certain embodiments where chemosynthetic reactions occur within the bioreactor, one or more types of electron donor and one or more types of electron acceptor are pumped or otherwise added as either a bolus addition, or periodically, or continuously to the nutrient medium containing chemoautotrophic organisms in the reaction vessel. The chemosynthetic reaction driven by the transfer of electrons from electron donor to electron acceptor in cellular respiration fixes inorganic carbon dioxide and/or other dissolved carbonates and/or other carbon oxides into organic compounds and biomass.

In certain embodiments a nutrient media for culture growth and production is used comprising an aqueous solution containing suitable minerals, salts, vitamins, cofactors, buffers, and other components needed for microbial growth, known to those skilled in the art [Bailey and Ollis, Biochemical Engineering Fundamentals, 2nd ed; pp 383-384 and 620-622; McGraw-Hill: New York (1986)].

In certain embodiments the chemicals used for maintenance and growth of microbial cultures as known in the art are included in the nutrient media of the present invention. In certain embodiments these chemicals may include but are not limited to one or more of the following: nitrogen sources such as ammonia, ammonium (e.g., ammonium chloride ($NH_4Cl$), ammonium sulfate (($NH_4)_2SO_4$)), nitrate (e.g., potassium nitrate ($KNO_3$)), urea or an organic nitrogen source; phosphate (e.g., disodium phosphate ($Na_2HPO_4$), potassium phosphate ($KH_2PO_4$), phosphoric acid ($H_3PO_4$), potassium dithiophosphate ($K_3PS_2O_2$), potassium orthophosphate ($K_3PO_4$), dipotassium phosphate ($K_2HPO_4$)); sulfate; yeast extract; chelated iron; potassium (e.g., potassium phosphate ($KH_2PO_4$), potassium nitrate ($KNO_3$), potassium iodide (KI), potassium bromide (KBr)); and other inorganic salts, minerals, and trace nutrients (e.g., sodium chloride (NaCl), magnesium sulfate ($MgSO_4\ 7H_2O$) or magnesium chloride ($MgCl_2$), calcium chloride ($CaCl_2$) or calcium carbonate ($CaCO_3$), manganese sulfate ($MnSO_4\ 7H_2O$) or manganese chloride ($MnCl_2$), ferric chloride ($FeCl_3$), ferrous sulfate ($FeSO_4\ 7H_2O$) or ferrous chloride ($FeCl_2\ 4H_2O$), sodium bicarbonate ($NaHCO_3$) or sodium carbonate ($Na_2CO_3$), zinc sulfate ($ZnSO_4$) or zinc chloride ($ZnCl_2$), ammonium molybdate ($NH_4MoO_4$) or sodium molybdate ($Na_2MoO_4\ 2H_2O$), cuprous sulfate ($CuSO_4$) or copper chloride ($CuCl_2\ 2H_2O$), cobalt chloride ($CoCl_2\ 6H_2O$), aluminum chloride ($AlCl_3\ 6H_2O$), lithium chloride (LiCl), boric acid ($H_3BO_3$), nickel chloride $NiCl_2\ 6H_2O$), tin chloride ($SnCl_2\ H_2O$), barium chloride ($BaCl_2\ 2H_2O$), copper selenate ($CuSeO_4\ 5H_2O$) or sodium selenite ($Na_2SeO_3$), sodium metavanadate ($NaVO_3$), chromium salts). In certain embodiments, the mineral salts medium (MSM) formulated by Schlegel et al may be used ["Thermophilic bacteria", Jakob Kristjansson, Chapter 5, Section III, CRC Press, (1992)].

Aspects of the invention relate to the growth and/or expression of bacterial cells. Bacterial cells associated with the invention can be cultured in some embodiments in media of any type (rich or minimal), including fermentation medium, and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, and ATCC Trace Mineral Supplement. Similarly, other aspects of the medium and growth conditions of the cells of the invention may be optimized through routine experimentation. For example, pH and temperature are non-limiting examples of factors which can be optimized. In some embodiments, factors such as choice of media, media supplements, and temperature can influence production levels of a desired molecule. In some embodiments, the concentration and amount of a supplemental component may be optimized. In some embodiments, how often the media is supplemented with one or more supplemental components, and the amount of time that the media is cultured before harvesting the desired molecule is optimized.

In certain embodiments, ash derived from the incineration or gasification of biomass contains mineral nutrients that may be used in the present invention. In certain embodiments, the incinerated or gasified biomass that results in mineral containing ash includes but is not limited to one or more of the following: dung, fecal matter and/or urine. In certain non-limiting embodiments urine is used as a source of nutrients including but not limited to as a nitrogen source. In certain non-limiting embodiments, the urine is diluted with water. In certain non-limiting embodiments urine and/or the products of incineration and/or gasification are used as nutrients for the biological organism of the present invention. In certain non-limiting embodiments, the primary products of incineration and/or gasification including but not limited to $CO_2$, water vapor, $H_2$, CO, and/or the inorganic mineral nutrients in ash, can be readily utilized by the biological organisms of the present invention.

The final products from the aerobic decomposition of organic matter generally are carbon dioxide, water, nitrates, phosphates, sulfates, and similar highly oxidized compounds. In certain embodiments of the present invention $CO_2$ and/or water and/or inorganic mineral nutrients derived from an activated sludge process is utilized as sources of feedstock and/or nutrients and/or electron acceptors in the present invention. In certain embodiments of the present invention $CH_4$ and/or $CO_2$ and/or water and/or ammonia and/or hydrogen sulfide and/or other inorganic mineral nutrients derived from anaerobic sludge digestion is utilized as a feedstock and/or nutrient source in the present invention. In certain embodiments humus is utilized as a carbon source and/or an electron acceptor or donor.

Aquacultural pollution, which can include nitrogen, in forms including but not limited to ammonia, as well as phosphorus, and dead fish is becoming a widespread hazard, particularly in Asia, where 90 percent of farmed fish are located. In certain embodiments of the present invention aquaculture pollution is utilized as a source of nutrients including but not limited to nitrogen and/or phosphorus by the microorganisms of the present invention. In certain embodiments waste that would normally go to a sewage or waste water treatment plant or landfill, instead is utilized for the production of nutrients for the microbial process of the present invention. In certain embodiments, these waste streams include but are not limited to one or more of the following: ammonia, urea, urine, feces, fish waste, and/or other animal waste. In certain embodiments, the microbial aspect of the present invention enables an increase in the water and/or nutrients that can be recirculated through an aquaculture system, and/or decrease the discharge from an aquaculture system. In certain embodiments electron donors and/or carbon sources including but not limited to one or more of the following: $H_2$, CO, $CH_4$, $CO_2$; and/or other nutrients and/or water are generated from fish waste and/or other animal waste including but not limited to feces and/or waste fish parts such as fish heads, and/or other animal residues and/or the microbial cellular material and/or organic matter refractive to waste water treatment through well-known processes including but not limited to one or more of the following: gasification, pyrolysis, incineration, and/or anaerobic digestion. In certain embodiments the $H_2O$ and/or $CO_2$ and/or other condensable and non-condensable gases and/or ash residue and/or heat that is generated through gasification and/or pyrolysis and/or incineration are utilized as feedstocks or inputs in the present invention such as but not limited to one or more of the following: $CO_2$ as a carbon source; $H_2O$ as a process water source; condensable and/or non-condensable gases as feedstocks and nutrient sources; ash as a inorganic mineral nutrient source and/or source of base for pH control; heat as a source of process heat and/or energy. Pathogenic microorganisms can survive the anaerobic waste treatment process. In certain embodiments, all pathogenic microorganisms present in raw waste feedstocks entering the process are killed through the aforementioned gasification and/or pyrolysis and/or incineration step or steps leading into one or more C1 capture and bioconversion steps.

In certain embodiments, the nutrients produced through the microbial bioprocess of the present invention are used in recirculating agriculture, aquaculture, aquaponics, or hydroponics systems. In certain non-limiting embodiments, the organisms produced in said recirculating aquaculture or aquaponics systems include but are not limited to one or more of the following: tilapia, salmon, cobia, trout, tilapia, catfish, carp, shrimp, shellfish. In certain non-limiting embodiments, the fish tanks in said recirculating aquaculture system are located on land or are floating in a body of water. In certain embodiments of the present invention, the microbial bioprocess is utilized as a source of nutrients for a floating fish farm. In certain such embodiments the floating fish farm is based on a retrofitted oil tanker or other large sea going vessel. In certain embodiments, the present invention is utilized as a source of nutrients for floating or suspended fish cages. In certain such embodiments the cages are used for salmon farming.

Certain embodiments of the present invention utilizing waste derived feedstocks and/or nutrients enable the closing of a food loop.

In certain embodiments of the present invention there is no requirement for arable land and/or fresh water and/or pesticides and/or herbicides and/or antibiotics. In certain embodiments, the need for fertilizer (e.g., inorganic minerals or organic nutrients for microbial growth) is partially or entirely met using waste sources including but not limited to one or more of the following: ashes, biomass, sewage, waste effluents. In certain embodiments of the present invention sea water is used as a source of process water and/or inorganic carbon and/or other mineral nutrients and/or fertilizer.

In certain embodiments, the concentrations of nutrient chemicals (e.g., the electron donors and acceptors and carbon sources and various mineral nutrients), are maintained within the bioreactor close to or at their respective optimal levels for optimal carbon uptake and/or fixation and/or conversion and/or production of organic compounds, which varies depending upon the microorganism utilized but is known or determinable without undue experimentation to one of ordinary skill in the art of culturing microorganisms.

In certain embodiments of the present invention one or more of the following parameters are monitored and/or controlled in the bioreactor: waste product levels; pH; temperature; salinity; dissolved oxygen; dissolved carbon dioxide gas; liquid flow rates; agitation rate; gas pressure. In certain embodiments, the operating parameters affecting chemoautotrophic growth are monitored with sensors (e.g., dissolved oxygen probe or oxidation-reduction probe to gauge electron donor/acceptor concentrations), and/or are controlled either manually or automatically based upon feedback from sensors through the use of equipment including but not limited to actuating valves, pumps, and agitators. In certain embodiments, the temperature of the incoming broth as well as of incoming gases is regulated means such as but not limited to coolers, heaters, and/or heat exchangers.

In certain embodiments of the present invention, the microbial culture and bioreaction is maintained using continuous influx and removal of nutrient medium and/or biomass, in steady state where the cell population and environmental parameters (e.g., cell density, pH, DO, chemical concentrations) are targeted at a constant level over time. In certain embodiments that constant level is an optimal level for feedstock conversion and/or production of targeted organic compounds. In certain embodiments cell densities, can be monitored by direct sampling, by a correlation of optical density to cell density, and/or with a particle size analyzer. In certain embodiments, the hydraulic and biomass retention times can be decoupled so as to allow independent control of both the broth chemistry and the cell density. In certain embodiments dilution rates can be kept high enough so that the hydraulic retention time is relatively low compared to the biomass retention time, resulting in a highly replenished broth for cell growth and/or feedstock conversion and/or production of organic compounds. In certain embodiments dilution rates are set at an optimal technoeconomic trade-off between culture broth and nutrient replenishment and/or waste product removal, and increased process costs from pumping, increased inputs, and other demands that rise with dilution rates.

In certain embodiments of the present invention, the pH of the microbial culture is controlled. In certain embodiments pH is controlled within an optimal range for microbial maintenance and/or growth and/or conversion of feedstock and/or production of organic compounds and/or survival. To address a decrease in pH, in certain embodiments a neutralization step can be performed directly in the bioreactor environment or prior to recycling the media back into the culture vessel through a recirculation loop. Neutralization of acid in the broth of certain embodiments can be accomplished by the addition of bases including but not limited to one or more of the following: limestone, lime, sodium hydroxide, ammonia, ammonium hydroxide, caustic potash, magnesium oxide, iron oxide, alkaline ash. In certain embodiments, the base utilized has been produced from a carbon dioxide emission-free source such as naturally occurring basic minerals including but not limited to one or more of the following: calcium oxide, magnesium oxide, iron oxide, iron ore, olivine containing a metal oxide, serpentine containing a metal oxide, ultramafic deposits containing metal oxides, and liquids from underground basic saline aquifers. If limestone is used for neutralization, then carbon dioxide will generally be released. In certain embodiments, this $CO_2$ can be retained or directed back into the bioreactor for uptake by chemosynthesis and/or utilized and/or sequestered in some other way, rather than released into the atmosphere.

In certain embodiments, ash derived from the combustion, incineration, or gasification of biomass is used for pH control. In certain embodiments, the incinerated or gasified biomass that results in basic ash includes but is not limited to one or more of the following: dung, fecal matter and/or urine.

In certain embodiments of the present invention an aqueous suspension of chemoautotrophic microorganisms converts one or more electron donors and $CO_2$ into protoplasm. In certain embodiments, an aqueous suspension of hydrogen-oxidizing microorganisms can be used to convert hydrogen and carbon dioxide into bacterial protoplasm. In certain embodiments, an aqueous suspension of carbon monoxide-oxidizing microorganisms can be used to convert carbon monoxide and hydrogen and/or water into protoplasm. In certain embodiments, an aqueous suspension of methane-oxidizing microorganisms can be used to convert methane into protoplasm. In certain embodiments, the microorganism in suspension is a bacterium or an archaea. In certain non-limiting embodiments, an aqueous suspension or biofilm of $H_2$-oxidizing chemoautotrophic microorganisms converts $H_2$ and $CO_2$, along with some other dissolved mineral nutrients, into biochemicals and protoplasm. In certain embodiments, the other dissolved mineral nutrients include but are not limited to a nitrogen source, a phosphorous source, and a potassium source. In certain embodiments, the protoplasm produced is of food value to humans and/or other animals and/or other heterotrophs. In certain embodiments, certain biochemicals may be extracted from the protoplasm and/or extracellular broth, which have nutrient value, and/or value in a variety of organic chemistry or fuel applications. In certain embodiments, the intracellular energy to drive this production of protoplasm is derived from the oxidation of an electron donor by an electron acceptor. In certain non-limiting embodiments, the electron donor includes but is not limited to one or more of the following: $H_2$; CO; $CH_4$. In certain non-limiting embodiments, the electron acceptor includes but is not limited to $O_2$. In certain non-limiting embodiments, the product of the energy generating reaction, or respiration, includes but is not limited to water. In certain embodiments, the intracellular energy derived from respiration used to drive this synthesis of biochemicals and protoplasm from $CO_2$ is stored and carried in biochemical molecules including but not limited to ATP. For the knallgas microbes used in certain embodiments herein the electron acceptor is $O_2$ and the product of respiration is water.

In some embodiments the protein production and distribution of amino acid molecules produced is optimized through one or more of the following: control of bioreactor conditions, control of nutrient levels, genetic modifications of the cells. In certain embodiments of the present invention pathways to amino acids, or proteins, or other nutrients, or whole cell products are controlled and optimized for the production of chemical products by maintaining specific growth conditions (e.g. levels of nitrogen, oxygen, phosphorous, sulfur, trace micronutrients such as inorganic ions, and if present any regulatory molecules that might not generally be considered a nutrient or energy source). In certain embodiments of the present invention dissolved oxygen (DO) may be optimized by maintaining the broth in aerobic, microaerobic, anoxic, anaerobic, or facultative conditions depending upon the requirements of organisms. A facultative environment is considered to be one having aerobic upper layers and anaerobic lower layers caused by stratification of the water column. The biosynthesis of amino acids, or proteins, or other nutrients, or whole cell products by the microbes disclosed in the present invention can happen during the logarithmic phase or afterwards during the stationary phase when cell doubling has stopped, provided there is sufficient supply of carbon and energy and other nutrient sources.

The specific examples of bioreactors, culture conditions, heterotrophic and chemotrophic growth, maintenance, and amino acids, or proteins, or other nutrients, or whole cell product production methods described herein can be combined in any suitable manner to improve efficiencies of microbial growth and amino acid, or protein, or other nutrient, or whole cell production.

In certain non-limiting embodiments of the present invention the biosynthetic reduction of $CO_2$ utilizes $O_2$ electron acceptor and/or $H_2$ electron donor which are generated by the electrolysis of water. In certain non-limiting embodiments of the present invention, part of the $O_2$ generated by electrolysis of water, and all of the $H_2$ is fed to an aqueous suspension of microorganisms of the present invention. In certain non-limiting embodiments, the molar ratio of $H_2$ fed to an aqueous suspension of microorganisms to the moles of $O_2$ is greater than 2:1. In certain non-limiting embodiments where $O_2$ electron acceptor and $H_2$ electron donor are generated by the electrolysis of water, there is a surplus of $O_2$ remaining after all of the metabolic requirements for $H_2$ and $O_2$ of the microorganisms of the present invention have been met. In certain such embodiments the surplus $O_2$ is supplied to humans and/or other aerobic lifeforms and/or is stored and sold as a chemical co-product.

Figure 29:
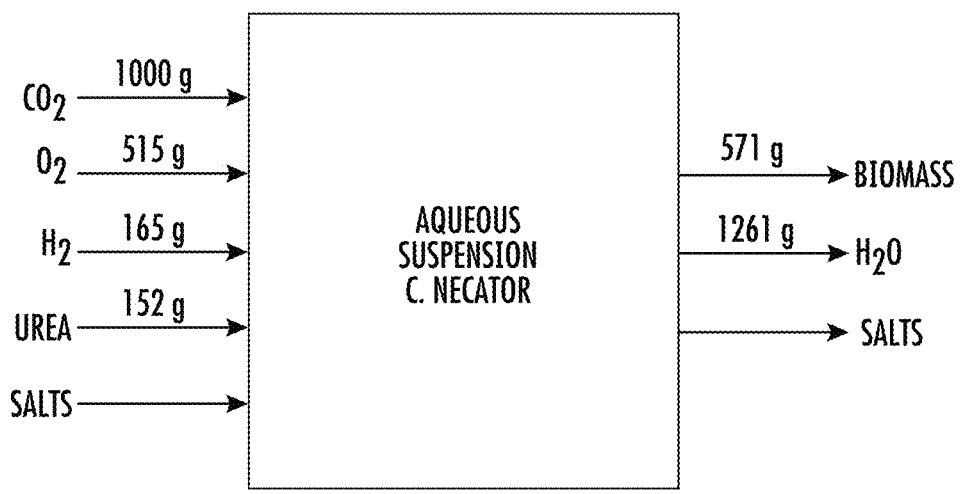
FIG. 29 shows partial material balance of a *C. necator* system.
Figure 30:
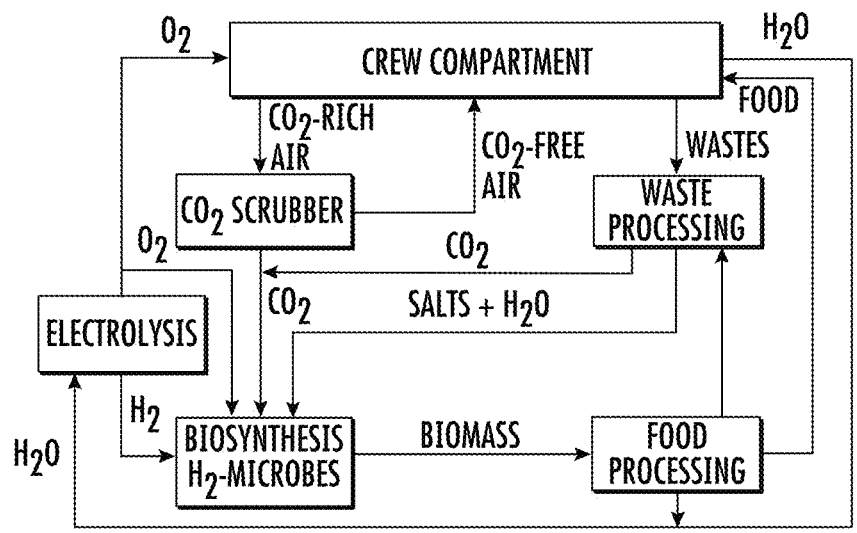
FIG. 30 shows a schematic flow diagram of a *C. necator* closed-loop life-support system.

In certain non-limiting embodiments the $CO_2$ has been removed from an industrial flue gas, or intercepted from a geological source that would otherwise naturally emit into the atmosphere, or it is removed from a closed cabin atmosphere. In certain embodiments, inorganic nutrient salts are fed at the onset of the process and/or simultaneously with the gases. In certain embodiments, the microorganisms grow and multiply on the $H_2$ and $CO_2$ and inorganic salts (nutrients) provided. In certain embodiments, the microorganisms oxidize the $H_2$ as an energy source for the synthesis of protoplasm. In certain non-limiting embodiments cells are harvested at some fixed rate: maintaining a steady-state population and gas uptake rate. Certain non-limiting embodiments of the present invention are used in closed-loop life support applications. In certain non-limiting embodiments, the present invention can be used to supplant or displace the Sabatier reaction that converts $H_2$ and $CO_2$ into methane. In certain non-limiting embodiments, instead of producing methane from $H_2$ and $CO_2$ through the Sabatier reaction, nutrients including but not limited to one or more of the following: protein, fats, and polysaccharides are produced using $H_2$ and $CO_2$. In certain non-limiting embodiments, the invention performs useful functions including but not limited to one or more of the following: $CO_2$ reduction; synthesis of biomass requiring minimum modification for food use; and utilization of urea and other nutrients in urine. In certain non-limiting embodiments $CO_2$ and/or CO and/or mineral nutrients in ash, arising from the gasification, reforming, or incineration of liquid and/or solid biological and/or other carbon-based wastes are used in the present invention. Inputs and outputs of a non-limiting example of the process provided for illustrative purposes is shown in FIG. 29. A non-limiting schematic flow diagram of a process given for illustrative purposes is shown in FIG. 30.

In certain non-limiting embodiments of the present invention one or more of the following functions is performed: $CO_2$ reduction; synthesis of cellular material that can be utilized as a food or nutrition source; the mitigation of nitrogenous wastes and the utilization of urea, ammonia, ammonium, and/or nitrate.

In certain non-limiting embodiments of the present invention a closed culture vessel is used and hydrogen, oxygen, and $CO_2$ under pressure are supplied to the vessel. In certain non-limiting embodiments, the flow of gases to the chamber is controlled by gas sensors to maintain fixed $H_2$, $O_2$, and $CO_2$ concentrations in the chamber. In certain non-limiting embodiments, the gases and culture medium are mixed by mechanical agitation in the vessel to maximize gas diffusion into the liquid. In certain non-limiting embodiments, the hydrogen and oxygen gases are supplied by a water electrolysis cell and the $CO_2$ is captured from a waste source or a source normally emitted into the atmosphere or cabin air. In certain non-limiting embodiments, the process stream flows to a biomass harvest unit. In certain non-limiting embodiments, centrifugal action is used to separate the solids from the liquid. In certain non-limiting embodiments liquid is recycled or sent to water recovery such as a water reclamation unit. In certain embodiments, the water produced through respiration of the microorganisms and/or by heterotrophs fed nutrients produced by the microorganisms, can be recycled to the electrolysis cell and/or back to the bioreactor. In certain embodiments, the water byproduct can be used to partially offset water demand for electrolytic production of $H_2$. In certain embodiments, the water byproduct is a co-product that may be purified and sold, or provided for the growth of plants or other organisms, or otherwise provided to other water consumers. In certain non-limiting embodiments, undesirable substances which might otherwise build up in the system are removed at the water reclamation unit. In certain non-limiting embodiments, the reclaimed water is re-used in the water electrolysis cell. In certain non-limiting embodiments, nutrient makeup is supplied to the culture vessel to maintain a targeted culture medium composition. In certain non-limiting embodiments urine is provided as a nutrient. In certain embodiments, the biomass generated is processed for use as food or other bio-based products.

In certain non-limiting embodiments of the present invention, the continuous culture, or batch or fed batch culture, of one or more microorganisms of the present invention is the intermediate step of a three-step closed life support cycle directed to the conversion of the human metabolic wastes: urea and carbon dioxide, into breathable oxygen and a food source and/or nutritional supplement. In these embodiments of the present invention, in addition to the chemoautotrophic $CO_2$-fixation step, the other two steps of the complete cycle are (1) the collection and recovery of the $CO_2$ removed from a cabin atmosphere and (2) the electrolysis of water to produce breathable oxygen for the cabin supply, and by-product hydrogen, which is fed to the gas phase of the closed culture vessel. In certain non-limiting embodiments, the bacteria use waste urea as a partial or sole nitrogen source during growth together with $CO_2$ waste as a carbon source. In certain non-limiting embodiments, the harvested excess of cells from a steady-state culture is a potential food for humans, animals, or other heterotrophs and/or a fertilizer for plants.

Not being limited by theory, it is believed that the relatively high FCR of fish and other aquaculture organisms is due to factors such as being cold-blooded and living in a buoyant environment and hence fighting gravity less. In certain non-limiting embodiments, the organisms which are fed proteins and/or other nutrient produced through the present invention are food producing species that are cold-blooded. In certain embodiments, the organisms fed protein and/or other nutrients produced through the present invention are heterotrophs, which are not endotherms, such as but not limited to microorganisms, fungi, animal cell cultures, and/or ectothermic animals. In certain non-limiting embodiments, the cells and/or organisms live in a buoyant environment. In certain non-limiting embodiments, the organisms are sedentary.

In certain embodiments the protein and/or other nutrients produced according the present invention are used in techniques and technologies for the raising of fish including but not limited to one or more of the following: hatcheries; pond culture; cage culture; recirculating systems; integrated multi-trophic aquaculture; integrated agriculture and aquaculture; aquaponics.

The present invention relates to bioreactors that comprise a cell, which comprises at least one endogenous or exogenous nucleic acid sequence that encodes a pathway enzyme to an amino acid, or protein, or other nutrient. In some embodiments, the system comprises two or more, three or more, or four or more bioreactors, at least one of which comprise a cell, which comprises at least one endogenous or exogenous nucleic acid sequence that encodes a pathway enzyme to an amino acid, or protein, or other nutrient. In some embodiments, the system of bioreactors comprises at least a first and second bioreactor, wherein the first bioreactor comprises a cell, which comprises at least one endogenous or exogenous nucleic acid sequence that encodes a pathway enzyme to an amino acid, or protein, or other nutrient; and wherein the second bioreactor comprises a microorganism derived from a different species, wherein the microorganism from a different species comprises at least one endogenous or exogenous nucleic acid sequence. In some embodiments, the system of bioreactors comprises a first bioreactor that comprises the cell of the present invention and a second bioreactor comprising a zooplankton, and/or a microalgal, yeast, bacterial, fungal, animal, and/or plant cell. In some embodiments, the system comprises a first bioreactor that comprises the cell of the present invention and a second tank or vessel comprising a multicellular animal and/or an aquaculture.

In certain embodiments microbes of the present invention are used to feed aquatic filter-feeders. In certain embodiments, the aquatic filter-feeders harvest the cells and/or biosynthetic products of the present invention from liquid suspension. In certain embodiments, the costs associated with solid-liquid separations and/or dewatering and/or drying of biomass are avoided by harvesting the cells and/or biosynthetic products of the present invention through the action of aquatic filter-feeders. Quahogs are a mollusk that filter water in and out of its shell with two short siphons, absorbing plankton, bacteria, and oxygen. Oysters consume nitrogen-containing compounds (nitrates and ammonia), phosphates, plankton, detritus, bacteria, and dissolved organic matter, removing them from the water. In certain embodiment of the present invention filter-feeders such as but not limited to quahogs and/or oysters are utilized. In certain non-limiting embodiments, the Eastern Oyster, *Crassostrea virginica*, is utilized. In certain embodiments of the present invention utilizing filter-feeding organisms, tilapia and/or silver and/or bighead carp are included among the filter-feeders. See, e.g., Taub, Ballard, K, Palmer, F. (1973) Production Of Shellfish By Continuous Algal Culture. *Proc. Nat. Shellfish Assoc.* 63; 10-11 (Abstr.) and Taub, F. B. et al. 1973. Algal culture as aquaculture feed. Research in fisheries, which are incorporated herein by reference in their entireties.

In certain non-limiting embodiments of the present invention the microorganisms of the present invention are maintained in a symbiotic relationship and/or a trophic relationship with other living organisms. In certain non-limiting embodiments of the present invention the microorganisms of the present invention are fed to filter feeding organisms such as but not limited to one or more of the following: clams; oysters; mussels; and/or other mollusks; brine shrimp; zooplankton; and/or filter-feeding fish. In certain embodiments the organisms fed protein and other nutrients produced according to the present invention can be grown in containers of natural or artificial origin including but not limited to bioreactors; biological scrubber columns; packed-bed reactors; plug-flow reactors; vats; tanks and in particular tank systems such as known in the prior arts of aquaculture, aquaponics, and hydroponics; digesters; towers; ponds; pools; reservoirs; wells; lagoons; cisterns; caves; caverns; mine shafts; and quarries. The container walls, boundaries, or lining of the structure containing the organisms can be composed of one or more materials including but not limited to steels, other metals and their alloys, plastics, fiberglass, ceramics, glass, concrete, cement, tar, bitumen, sealant, wood, soil, sand, clay, stone and any combination thereof. In certain non-limiting embodiments, the organisms such as but not limited to filter-feeding organisms can also be grown in more open structures such as pens.

In certain embodiments of the present invention additional carbon dioxide may be sequestered in process steps occurring in series or parallel to the chemosynthetic process steps wherein carbon dioxide and/or other dissolved carbonates are reacted with minerals including but not limited to oxides or hydroxides or dissolved metal cations to form a carbonate or bicarbonate product. In certain embodiments, further carbon dioxide and/or other dissolved carbonates may be sequestered through the catalytic action of organisms that convert carbon dioxide and/or dissolved bicarbonate and/or dissolved carbonate and/or dissolved metal cations into solid carbonates or biominerals within biological step/s.

In certain embodiments one or more organisms which naturally convert carbon dioxide and/or dissolved bicarbonate and/or dissolved carbonate and/or dissolved metal cations into solid carbonates or biominerals are fed microorganisms and/or nutrients derived from microorganisms of the present invention. In certain said embodiments, the organisms produce carbonate containing materials including but not limited to shell or reef material. In certain embodiments, the organisms producing carbonate containing materials are filter-feeders. Of the entire amount of shellfish produced, 75 to 90% often consists of shells. These shells are composed of 95% calcium carbonate, and the remainder is organic matter and other compounds.

In certain non-limiting embodiments, the nutrients produced in the microbial process of the present invention are used to grow shellfish which are composed of 75 to 90% by weight of shell material, which has a calcium carbonate content of around 95%. In certain embodiments, the organisms producing carbonate containing materials include but are not limited to one or more of the following: oysters, clams, mussels, other mollusks, and coral. In certain said embodiments, an edible product is formed such as but not limited to meat, as well as a solid inedible carbonate containing material, including but not limited to shells. In certain embodiments, the organisms producing meat and shells include but are not limited to oysters, clams, mussels, and other mollusks.

In certain embodiments, the carbon that is sequestered in the solid carbonate biomaterial exceeds the carbon that is contained in the edible parts of the organism. In certain embodiments, the carbon that is sequestered into the shell counteracts, in some amount, the carbon that is lost as $CO_2$ in the trophic conversion of microbial biomass, produced according to the present invention, into edible shellfish biomass, via providing the microbial biomass as an aquaculture feed. In certain embodiments, the carbon that is sequestered in carbonate materials including but not limited to shells or coral, exceeds the carbon that is lost in the said trophic conversion, such that there is a net increase in carbon captured when trophically converting microbial cell mass into organisms including but not limited to shellfish or coral.

In certain embodiments, the carbon that is sequestered in carbonate biomaterial through the present invention is sequestered from the atmosphere for a much longer period of time than carbon that is fixed into microbial biomass. In certain embodiments, the carbon that is sequestered in carbonate biomaterial through the present invention is sequestered from the atmosphere for a much longer period of time than carbon that is contained in soft tissues of organisms fed the microorganisms and/or nutrients thereof produced according to the present invention. In certain embodiments, the carbon that is captured in carbonate biomaterials, including but not limited to shells and/or coral, is sequestered for over one hundred years. See, e.g., M. R. Hamester, P. S. Balzer, and D. Becker, "Characterization of calcium carbonate obtained from oyster and mussel shells and incorporation in polypropylene," *Materials Research*, vol. 15, pp. 204-208, 2012, G.-L. Yoon, B.-T. Kim, B.-O.

Kim, and S.-H. Han, "Chemical-mechanical characteristics of crushed oyster-shell," Waste Management, vol. 23, no. 9, pp. 825-834, January 2003., and the Presentation by Ingrid Lupatsch, from the Centre for Sustainable Aquaculture Research, Swansea University, UK entitled "Studies On Energy And Protein Requirements Of Juvenile Pacific Oyster *Crassostrea Gigas* Fed Live *Chaetoceros Muelleri*," which are incorporated herein by reference in their entireties.

Certain embodiments of the present invention relate to a batch or continuous zooplankton culture system and/or aquaculture system for the growth of filter-feeding organisms. Certain non-limiting embodiments of the present invention may include a culture reactor; a screening system configured to keep the zooplankton and/or filter-feeding organisms within the reactor; a microbial feeding unit wherein one or more microorganisms of the present invention are fed to the zooplankton and/or filter feeding organisms; a pH adjustment and control system; and an oxygen delivery system. In certain embodiments, the eggs of filter feeding organisms are harvested. In certain embodiments, the eggs that are harvested are those of brine shrimp. In certain embodiments, the brine shrimp eggs are skimmed from the water surface of an enclosure where brine shrimp are raised. In certain embodiments, the harvested eggs are then cleaned and/or frozen and/or brined and/or tested and/or dried.

An additional feature of certain non-limiting embodiments of the present invention regards the source, production, or recycling of the electron donors used by the chemoautotrophic microorganisms to fix carbon dioxide and/or other C1 feedstocks into organic compounds. The electron donors used for carbon dioxide capture and carbon fixation can be produced or recycled in certain embodiments of the present invention electrochemically or thermochemically using power from a number of different renewable and/or low carbon emission energy technologies including but not limited to: photovoltaics, solar thermal, wind power, hydroelectric, nuclear, geothermal, enhanced geothermal, ocean thermal, ocean wave power, tidal power. Many of the reduced inorganic chemicals upon which chemoautotrophs can grow (e.g. $H_2$, CO, $H_2S$, ferrous iron, ammonium, $Mn^{2+}$) can be readily produced using electrochemical and/or thermochemical processes well known in the art and science of chemical engineering that can be powered by a variety carbon dioxide emission-free or low-carbon emission and/or renewable sources of power including but not limited to photovoltaics, solar thermal, wind power, hydroelectric, nuclear, geothermal, enhanced geothermal, ocean thermal, ocean wave power, or tidal power.

In certain embodiments of the present invention that use molecular hydrogen as electron donor the $H_2$ is generated by methods well known to art and science of chemical and process engineering including but not limited to one or more of the following: through electrolysis of water including but not limited to approaches using Proton Exchange Membranes (PEM), liquid electrolytes such as KOH, alkaline electrolysis, Solid Polymer Electrolyte electrolysis, high-pressure electrolysis, high temperature electrolysis of steam (HTES); and/or through the thermochemical splitting of water through methods including but not limited to the iron oxide cycle, cerium(IV) oxide-cerium(III) oxide cycle, zinc zinc-oxide cycle, sulfur-iodine cycle, copper-chlorine cycle, calcium-bromine-iron cycle, hybrid sulfur cycle; and/or electrolysis of hydrogen sulfide; and/or thermochemical splitting of hydrogen sulfide; and/or other electrochemical or thermochemical processes known to produce hydrogen with low- or no-carbon dioxide emissions including but not limited to: carbon capture and sequestration (CCS) enabled methane reforming; CCS enabled coal gasification; the Kvormer-process and other processes generating a carbon-black product; CCS enabled gasification or pyrolysis of biomass. In certain embodiments of the present invention the approach to generating $H_2$ includes but is not limited to electrolysis powered by renewable electrical energy and/or electricity from a low-GHG source. In certain embodiments of the present invention electrolysis is powered by one or more of the following: solar including but not limited to photovoltaics and/or solar thermal; wind power, hydroelectric; nuclear; geothermal; enhanced geothermal; ocean thermal; ocean wave power; tidal power.

In certain embodiments of the present invention, the microbial bioprocess is integrated with, and provides nutrients, to an agricultural or aquacultural process. In certain embodiments, the electricity and/or heat requirements of the said agricultural or aquacultural process are met using renewable energy and/or energy from a low-GHG source.

In certain embodiments of the present invention, renewable power produced during off-peak demand hours for the electrical grid, is used to produce $H_2$ feedstock for the process. In certain embodiments of the present invention, onsite storage of $H_2$ and $CO_2$ gases enables diversion of power from the grid only during periods when renewable generation exceeds electrical demand. In certain embodiments power is allowed to flow as usual into the grid during periods of higher demand. In certain embodiments of the present invention the process does not disrupt renewable power supply, but rather enables more complete utilization of renewable generation capacity such as but not limited to wind and solar. Certain embodiments of the present invention allow continued renewable operation and generation even during periods when electrical generation exceeds grid demand (e.g. off-peak wind or solar generation).

In certain embodiment of the present invention hydrogen electron donors are not necessarily generated with low- or no-carbon dioxide emissions, however the hydrogen is generated from waste, sustainable, or low value sources of energy and/or carbon using methods known in to art of chemical and process engineering. Such methods include but are not limited to gasification, pyrolysis, steam-reforming, or autothermal reforming of feedstock such as but not limited to one or more of the following: municipal solid waste, black liquor, agricultural waste, wood waste, stranded natural gas, biogas, sour gas, methane hydrates, liquid petroleum gas, pet coke, tires, sewage, manure, straw, sea weed and kelp, and low value, highly lignocellulosic biomass in general.

In certain embodiments of the present invention a synthesis gas or producer gas containing $H_2$ and/or CO and/or $CO_2$ is utilized as an electron donor and/or as a carbon source. In certain embodiments, the $H_2$ and/or CO and/or $CO_2$ contained in a syngas or producer gas is supplemented by $H_2$ generated using a renewable and/or low-GHG energy source and conversion process such as one or more of those described herein.

In certain embodiments, the gasification, pyrolysis, incineration, and/or anaerobic digestions used to generate electron donors and/or carbon sources that are used in the bioprocess of the present invention, also generate useful co-products including but not limited to electricity and/or process heat, which are utilized in the microbial bioprocess, and/or an associated agricultural or aquacultural system, and/or provided to a grid or utility, or otherwise provided to surrounding consumers.

In certain embodiments, process heat generated as a co-product of the production of hydrogen and/or CO via methods such as gasification, pyrolysis, or steam-reforming is recovered and utilized elsewhere in the conversion process to improve overall energy efficiency. A chemical and/or heat and/or electrical co-product can accompany the generation of molecular hydrogen and/or CO, which can be used to the extent possible elsewhere in the conversion process of certain embodiments of the present invention, for example, in order to improve efficiency.

In certain embodiments, additional chemical co-product (e.g., beyond what can be used in internally in the conversion process of certain embodiments of the present invention) can be prepared for sale in order to generate an additional stream of revenue. Excess heat or electrical energy co-product in the production of molecular hydrogen and/or CO (e.g., beyond what can be used internally in the process) can be delivered for sale, for example, for use in another chemical and/or biological process through means known in the art and science of heat exchange and transfer, and electrical generation and transmission, including but not limited to the conversion of process heat to electrical power in a form that can be sold into the electrical grid.

In certain embodiments of the present invention that utilize $H_2$ as an electron donor, there can be a chemical co-product formed in the generation of $H_2$ using a renewable and/or $CO_2$ emission-free energy input. If for example water is used as a hydrogen source, then oxygen can be a co-product of water splitting through processes including but not limited to electrolysis or thermochemical water splitting. In certain embodiments of the present invention using water as a hydrogen source and knallgas microorganisms, some of the oxygen co-product can be used for the production of ATP and/or other intracellular energy carriers through respiration by the oxyhydrogen reaction. In certain embodiments of the present invention, the oxygen produced by water-splitting in excess of what is required for respiration in order to maintain optimal conditions for carbon fixation and organic compound production by the knallgas microorganisms and/or other aerobic organisms in the system, may be processed into a form suitable for sale through process steps known in the art and science of commercial oxygen gas production.

The electron donors in certain embodiments of the present invention may also be sourced or refined from pollutants or waste products including but not limited to one or more of the following: process gas; tail gas; enhanced oil recovery vent gas; stranded natural gas; biogas; landfill gas; and sour gases. In certain embodiments of the present invention a tail gas containing $H_2$ and/or $CH_4$ and/or CO is used as a source of electron donor and/or carbon. In certain embodiments tail gases from an oil refinery are used as a source of electron donors and/or carbon.

In certain non-limiting embodiments, organic compounds containing only one carbon atom are generated through the gasification and/or pyrolysis of biomass and/or other organic matter (e.g., biomass and/or other organic matter from waste or low value sources); and/or through methane steam reforming of methane or natural gas (e.g., stranded natural gas, or natural gas that would be otherwise flared or released to the atmosphere), or biogas, or landfill gas, and provided as a syngas and/or other gas or streams of C1 compounds to the culture of microorganisms; where in certain embodiments the ratio of hydrogen to carbon monoxide in the syngas or producer gas may be adjusted through means such as the water gas shift reaction, and/or where the ratio of hydrogen to $CO_2$ may be adjusted through means such as carbon capture, prior to the gases being delivered to the microbial culture.

In some embodiments the biomass produced through the present invention is converted to animal feed or incorporated into an animal feed formulation or utilized as a source of human nutrition.

A significant fraction of higher plants is inedible to many different animals including but not limited to humans and other non-ruminants. This can lead to numerous disadvantages including the channeling of energy and carbon into undesirable byproducts or waste products. This can lower the yield of desired products and add addition burdens for waste processing and disposal.

In certain embodiments of the present invention a greater flux of carbon and/or energy is directed into targeted biomass products than for a comparable, in terms of $CO_2$ capture and/or biomass production, higher plant crop. In certain embodiments, the ratio of inedible to edible parts of the biomass produced in the present invention is lower than for a higher plant crop.

In certain embodiments, a higher-plant culture grown under artificial lighting, will require at least thirty times more electrical power per unit weight of edible biomass produced than the present invention. The growth cycle of higher plant crops is relatively long, so that food harvests are periodic, and consumption generally does not match production. This mismatch between production and consumption generally necessitates relatively widespread preservation and storage to prevent wastage.

In certain embodiments of the present invention the production of biomass by the microorganisms of the present invention and the consumption of biomass products by animals or other heterotrophs is much more closely matched than for a comparable system based on higher plant crops. In certain embodiments of the present invention, less preservation and/or storage of biomass is required than for a comparable system based on higher plant crops. In certain embodiments of the present invention, there is lower amounts of food wastage than for comparable higher plant crops.

In some embodiments, the microorganisms of the present invention produce at least 1 mg of carbon-based product of interest per liter of liquid culture suspension. In some examples, the product is secreted by the organism into culture medium. In other examples, the product is retained in the organism in the course of fermentation. In some cases, the product may be recovered by lysing the cells and separating the product. In other cases, the product may have commercial value in the intact organism without significant preparation or purification of the product from the organism.

In certain embodiments recovery of biosynthetic chemical products and/or spent nutrients from the aqueous broth solution can be accomplished using equipment and techniques known in the art of process engineering, and targeted towards the chemical products of particular embodiments of the present invention, including but not limited to: solvent extraction; water extraction; distillation; fractional distillation; cementation; chemical precipitation; alkaline solution absorption; absorption or adsorption on activated carbon, ion-exchange resin or molecular sieve; modification of the solution pH and/or oxidation-reduction potential, evaporators, fractional crystallizers, solid/liquid separators, nanofiltration, and all combinations thereof.

In certain embodiments of the present invention separation of cell mass from liquid suspension is performed. In certain embodiments, this separation is performed by methods known in the art of microbial culturing. Examples of cell mass harvesting techniques are provided, for example, in PCT Application No. WO08/00558, published Jan. 8, 1998; U.S. Pat. Nos. 5,807,722; 5,593,886 and 5,821,111, incorporated by reference herein in their entireties, including but not limited to one or more of the following: centrifugation; flocculation; flotation; filtration using a membranous, hollow fiber, spiral wound, or ceramic filter system; vacuum filtration; tangential flow filtration; clarification; settling; hydrocyclone. In certain embodiments where the cell mass may be immobilized on a matrix, it may be harvested by methods including but not limited to gravity sedimentation or filtration, and separated from the growth substrate by scraping or liquid shear forces.

In certain embodiments the liquid left over following the removal of cell mass can be pumped to a system for removal and/or recovery of dissolved chemical products of the bioprocess and/or unreacted nutrients. In certain embodiments, unreacted nutrients and/or water are recovered and recycled to the extent possible and/or in certain embodiments sold as a co-product and/or properly disposed of. In certain embodiments, the removal of waste products and/or contaminants and/or any inhibitory and/or deleterious compounds using methods and technologies known in the art is performed prior to returning water and/or unreacted nutrients to the bioreactor/s.

In certain embodiments of the present invention involving chemoautotrophic microorganisms a solution of oxidized metal cations can remain following the chemosynthetic reaction step or steps. In other non-limiting embodiments, a solution rich in dissolved metal cations can also result from particulates and impurities carried in certain gas inputs to the process such as from a coal fired plant or gasification of coal or municipal solid waste (MSW).

In some embodiments of the present invention where metal cations are present in the process stream that would be advantageous to remove, the process stream can be stripped of metal cations by methods including but not limited to: cementation on scrap iron, steel wool, copper or zinc dust; chemical precipitation as a sulfide or hydroxide precipitate; electrowinning to plate a specific metal; absorption on activated carbon or an ion-exchange resin, modification of the solution pH and/or oxidation-reduction potential, reverse osmosis, and/or solvent extraction. In certain embodiments of the present invention, the recovered metals can be recycled and/or sold for an additional stream of revenue.

In certain embodiments free and/or dissolved organic molecules can be released into the process stream solution from the microorganisms through means including but not limited to cellular excretion or secretion or cell lysis.

In certain embodiments recovery and/or recycling of chemical products and/or unreacted nutrients from the aqueous solution can be accomplished in certain embodiments of the present invention using equipment and techniques known in the art of process engineering, and targeted towards the chemical products of particular embodiments of the present invention, including but not limited to: solvent extraction; water extraction; distillation; fractional distillation; cementation; chemical precipitation; alkaline solution absorption; absorption or adsorption on activated carbon, ion-exchange resin or molecular sieve; modification of the solution pH and/or oxidation-reduction potential, evaporators, fractional crystallizers, solid/liquid separators, nanofiltration, reverse osmosis, and all combinations thereof.

In certain embodiments, chemical products and/or unreacted nutrients flow into an environment that supports the growth of other organisms. In certain embodiments, effluent water and unreacted nutrients are used to irrigate and fertilize higher plants. Tilapia and other aquatic animals, are able to absorb minerals from the culture water. In certain embodiments, unreacted mineral nutrients flow into a grow environment for Tilapia and/or other aquatic animals. In certain embodiments of the present invention inorganic nutrients flow from the chemoautotrophic bioreactor of the present invention to an aquaculture system containing animals including but not limited to tilapia and stimulate the production of live food organisms and plants in the culture system including but not limited to phytoplankton. In certain embodiments inorganic and/or organic nutrients from the bioreactor effluent function as a fertilizer which increase primary production of a pond and/or or other enclosures used in aquaculture and/or aquaponics and/or hydroponics.

In certain embodiments, the chemoautotrophically generated biomass of the present invention produced from carbon sources including but not limited to one or more of the following: $CO_2$, $CO$, $CH_4$, $CH_3OH$; flows or is otherwise applied to an agricultural and/or aquacultural and/or aquaponics and/or hydroponics system where it supplements and/or displaces organic manures in directly stimulating higher trophic levels by supplying organic matters and detritus. In certain embodiments, the said organic matter represents an immediate source of food for species including but not limited to species that can feed on detritus and plant by-products including but not limited to Tilapia.

In certain non-limiting embodiments of the present invention the dry weight of organic matter produced chemoautotrophically is applied daily at 2-4% of the fish biomass. In certain of these embodiments the DO and/or pH and/or water transparency in the aquaculture enclosures are monitored. In certain of these embodiments the input of organic matter is suspended if the DO falls below 4.0 mg/l and/or the pH goes above 9.0 and/or the water transparency falls below 25 cm.

In certain embodiments a polyculture is fed organic matter and/or inorganic nutrients flowing from a bioreactor of the present invention. In certain embodiments, the polyculture comprises tilapia and/or carp and/or shrimp. See, e.g., Nile tilapia—Fertilizers and fertilization, Food and Agriculture Organization of the United Nations (FAO), which is incorporated herein by reference in its entirety.

In certain embodiments of the present invention nutrients produced in the microbial process of the present invention are used to fertilize ponds where a polyculture is implemented. In certain embodiments nutrients produced through the microbial process of the present invention are used to fertilize plant crops including but not limited to rice. In certain embodiments nutrients produced in the microbial process of the present invention are fed into an integrated multi-trophic aquaculture system that includes but is not limited to one or more of the following: finfish, abalone, shellfish, seaweed, kelp, and/or other invertebrates including but not limited to sea cucumbers.

The high growth rate attainable by certain chemoautotrophic species can allow them to match or surpass the highest rates of carbon fixation and/or biomass production per standing unit biomass that can be achieved by photosynthetic microbes. In certain embodiments, surplus biomass can be produced. In certain embodiments, surplus growth of cell mass can be removed from the system to produce a biomass co-product. In some embodiments, surplus growth of cell mass can be removed from the system in order to maintain a desirable (e.g., an optimal) microbial population and cell density in the microbial culture for continued high carbon capture and fixation rates and/or feedstock conversion rates.

In certain embodiments, the chemicals that are used in processes for the recovery of chemical products and/or the recycling of nutrients and water and/or the removal of waste have low toxicity for humans, and if exposed to the process stream that is recycled back into the bioreactor, low or no toxicity for the particular microorganisms being used in that particular embodiment of the invention.

In certain embodiments of the present invention, if an excess of cells have been removed from the culture during the harvesting/separations/product recovery process, the excess cells removed can be returned back into the cell culture within the bioreactor, along with fresh nutrient media in certain cases, such that sufficient and/or optimal cell number and density is retained in bioreactor reaction step or steps. In certain embodiments, this can facilitate attaining targeted and/or optimal feedstock conversion and/or production of organic compounds. In certain embodiments, the cells removed by the harvesting/separations/product recovery system can be recycled back into the culture vessel, for example, using an airlift or geyser pump. In certain embodiments, the cells recycled back into the culture vessel are not exposed to flocculating agents, unless those agents are non-toxic to the microorganisms.

To assist in the processing of the biomass product into useful products, harvested microbial cells in certain embodiments of the invention can be broken open using well known methods including but not limited to one or more of the following: ball milling, cavitation pressure, sonication, homogenization, or mechanical shearing.

The harvested biomass in some embodiments may be dried in a process step or steps. Biomass drying can be performed in certain embodiments of the present invention using well known technologies including but not limited to one or more of the following: centrifugation, drum drying, evaporation, freeze drying, heating, spray drying, vacuum drying, and/or vacuum filtration. In certain embodiments of the present invention waste heat can be used in drying the biomass. In certain embodiments heat waste from the industrial source of flue gas used as a carbon source can be used in drying the biomass. In certain embodiments, the heat co-product from the generation of electron donors and/or C1 carbon source as discussed above can be used for drying the biomass.

In certain embodiments of the invention, the biomass is further processed following drying, or, without a preceding drying step, in order to aid the separation and production of useful biochemicals. In certain embodiments, this additional processing involves the separation of the protein or lipid content or vitamins or other targeted biochemicals from the microbial biomass. In certain embodiments, the separation of the lipids can be performed by using nonpolar solvents to extract the lipids such as, but not limited to one or more of: hexane, cyclohexane, ethyl ether, alcohol (isopropanol, ethanol, etc.), tributyl phosphate, supercritical carbon dioxide, trioctylphosphine oxide, secondary and tertiary amines, or propane. In certain embodiments, other useful biochemicals can be extracted using solvents including but not limited to one or more of: chloroform, acetone, ethyl acetate, and tetrachloroethylene.

In some embodiments, the instant invention provides for a method of producing amino acids and/or proteins by combining, in a bioreactor or solution, one or more biosynthetic pathways including but not limited to an amino acid biosynthetic pathway, a carbon-containing gas, and an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into amino acids and/or proteins. In some embodiments, the amino acids and/or proteins are included in an animal feed formulation using processes known in the art and science of chemistry, chemical engineering, and food science.

In certain embodiments of the present invention proteinaceous biomass produced through the invention is used as an alternative protein source. In certain embodiments, it is used as a replacement for fish meal or casein or whey or soy meal. In certain embodiments of the present invention proteins produced according to the invention are used in feed or fertilizer formulations in place of fish meal or casein or whey or soy meal or other plant proteins. In certain non-limiting embodiments of the present invention the protein products are not deficient in any essential amino acids. In certain non-limiting embodiments, the protein products are not deficient in lysine and/or methionine. In certain non-limiting embodiments, the proteinaceous biomass does not contain significant amounts of anti-nutritional factors. In certain embodiments, the proteinaceous biomass does not contain significant amounts of one or more of the following: gossypol, glucosinolates, saponins, trypsin inhibitors. In certain embodiments, the proteinaceous biomass serves as a non-conventional protein source that is suitable for species including but not limited to *Oreochromis niloticus*.

Engineering of knallgas microorganisms is described in U.S. Patent Application No. 2013/0089899, filed Sep. 19, 2012, and entitled "INDUSTRIAL FATTY ACID ENGINEERING GENERAL SYSTEM FOR MODIFYING FATTY ACIDS." This application is incorporated herein by reference in its entirety for all purposes.

Use of knallgas microorganisms for the conversion of syngas, producer gas, or other $H_2$ and $CO_2$ and/or CO containing gas mixes in high energy density molecules is described in U.S. Patent Application No. e on Oct. 26, 2012 under No. 2013/0149755, and entitled USE OF OXYHYDROGEN MICROORGANISMS FOR NON-PHOTOSYNTHETIC CARBON CAPTURE AND CONVERSION OF INORGANIC AND/OR C1 CARBON SOURCES INTO USEFUL ORGANIC COMPOUNDS. This application is incorporated herein by reference in its entirety for all purposes.

Use of chemotrophic microorganisms for the conversion of $CO_2$ into useful organic chemicals is described in PCT international application number PCT/US2010/001402, filed May 12, 2010, published in the U.S. as Application No. 2013/0078690, and entitled BIOLOGICAL AND CHEMICAL PROCESS UTILIZING CHEMOAUTOTROPHIC MICROORGANISMS FOR THE CHEMOSYNTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS. This application is incorporated herein by reference in its entirety for all purposes.

Aspects of the invention relate to engineered organisms for use in the production of molecules for industrial application. As used herein, "engineered organisms" and "engineered microorganism" and "non-naturally occurring microorganism" are used interchangeably and refer to organisms that recombinantly express nucleic acids comprising at least one exogenous gene. In some embodiments, such nucleic acids encode enzymes as discussed herein. Homologs and alleles of genes associated with the invention can be identified by conventional techniques. Also encompassed by the invention are nucleic acids, referred to as "primers" or "primer sets," that hybridize under stringent conditions to the genes described herein. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York.

An additional feature of some embodiments of the present invention regards modifying microorganisms of the present invention through artificial means including but not limited to accelerated mutagenesis (e.g., using ultraviolet light or chemical treatments), genetic engineering or modification, hybridization, synthetic biology or traditional selective breeding. Possible modifications of the microorganisms include but are not limited to those directed at producing increased quantity and/or quality of amino acids, and/or vitamins, and/or protein.

Post-Process Conversions
Production of Animal or Aquacultural Feed

In some embodiments protein and/or proteinaceous biomass produced according to the present invention is then converted to animal feed using methods and processes well known in the art and science of chemistry, chemical engineering, and food science. In certain embodiments, the feed produced through the invention is used to grow organisms including but not limited to one or more of the following: other microorganisms, yeast, fungi, zooplankton, shellfish or other invertebrates; fish; birds; mammals. In certain non-limiting embodiments, the fish include but are not limited to one or more of: tilapia; salmon; cobia. In certain non-limiting embodiments, the birds include but are not limited to chickens or turkeys. In certain non-limiting embodiments, the mammals include but are not limited to one or more of: rabbits, goats, sheep, pigs, cows. In certain non-limiting embodiments, the feed produced through the present invention is used to grow live-feed that in turn sustain finfish larvae through the first weeks of life. In certain embodiments, this live-feed comprises Zooplankton. In certain embodiments, feed produced according to the present invention is used to grow zooplankton organisms including but not limited to one or more of the following: rotifers [Phylum Rotifera]; order Cladoceran (e.g., *Daphnia* sp., *Moina* sp.); sub-class Copepoda (e.g., Cyclops); Brine shrimp (*Anemia* sp.).

In some embodiments of the present invention over 90% of the nitrogen from the protein produced by the bacterium is absorbed by an organism that consumes the amino acids or peptides or proteins or proteinaceous biomass. In some embodiments, the microbial cells of the present invention are boiled prior to feeding to another organism. In other embodiments, the cells are sonicated, or otherwise lyzed or ruptured prior to feeding to another organism.

One of the major challenges in utilizing biosystems for food production is obtaining the proper dietary balance between the quantities of protein, carbohydrate, and fat. The microbial systems generally considered for food synthesis tend to produce biomass disproportionately high in protein. In certain embodiments of the present invention an oleaginous strain is used that produces a higher proportion of fats and oils relative to protein content. In certain embodiments, the oleaginous strain utilized is in the *Rhodococcus* genus.

In certain embodiments, a carbohydrate or polysaccharide producing strain is utilized that produces a higher proportion of carbohydrates or polysaccharide relative to protein content. In certain embodiments, the carbohydrate or polysaccharide producing strain utilized is *Hydrogenovibrio marinus*.

Production of Carbonate Containing Materials

In certain embodiments the protein and/or other nutrients produced through the present invention are used to grow organisms that biosynthesize carbonate containing biomaterials including but not limited to shells and/or corals. There is a high content of calcium carbonate in mussel and oyster shells, which can be used in the formulation of medicine, in construction or as filler in polymer materials.

In certain embodiments, calcium carbonate from mussel and/or oyster shells and/or from other shellfish and/or coral grown according to the present invention, is used as construction material. In certain embodiments, it is used as an aggregate.

In certain embodiments, shells produced according to the present invention, including but not limited to oyster and/or clam and/or scallop shells, are used as pavement or hardscaping. In certain embodiments, the shells are used as an alternative to gravel and/or crushed stone toppings. In certain embodiments, the shells are used to pave driveways and/or paths and/or patios and/or courtyards and/or bocce ball courts. In certain embodiments, shells including but not limited to oyster shells are used as a landscaping material and/or as a nutrient-rich soil amendment and/or and a natural pest deterrent.

In certain embodiments, oyster shells and/or other shells or calcareous materials produced according to the present invention are utilized along with fly ash and/or blast furnace slag in construction material compositions. See, e.g., G.-L. Yoon, B.-T. Kim, B.-O. Kim, and S.-H. Han, "Chemical-mechanical characteristics of crushed oyster-shell," *Waste Management*, vol. 23, no. 9, pp. 825-834, January 2003. [Online]. Available: http://dx.doi.org/10.1016/s0956-053x (02)00159-9; E.-I. Yang, S.-T. Yi, and Y.-M. Leem, "Effect of oyster shell substituted for fine aggregate on concrete characteristics: Part i. fundamental properties," *Cement and Concrete Research*, vol. 35, no. 11, pp. 2175-2182, November 2005. [Online]. Available: http://dx.doi.org/10.1016/j.cemconres.2005.03.016; H. Yoon, S. Park, K. Lee, and J. Park, "Oyster shell as substitute for aggregate in mortar," Waste Management & Research, vol. 22, no. 3, pp. 158-170, June 2004. [Online]. Available: http://dx.doi.org/10.1177/0734242x04042456, which are incorporated herein by reference in their entireties.

In certain embodiments the shells produced in the present invention including but not limited oyster shells are pulverized and used as an ingredient in highway paving. In certain embodiments, a tabby is produced using shells made according to the present invention. In certain embodiments, the $CO_2$ emitted in the quicklime production process is recaptured and reutilized by the microbes of the present invention. In certain embodiments, a shellcrete is made from shells produced in the present invention.

In certain embodiments, carbonate material produced including but not limited to shells and/or corals are reflective. In certain embodiments, such carbonate materials have a high albedo. In certain embodiments, such carbonate materials are utilized in reflective surfaces and geoengineering to reduce or counter global warming. In certain embodiments, the carbonate materials are used in a reflective hardscape. In certain embodiments, the carbonate materials are used in lighter color or reflective roads and highways.

See, e.g., R. G. Watts, Engineering Response to Global Climate Change: Planning a Research and Development Agenda, Taylor & Francis, 1997. [Online]. Available: https://books.google.com/books?id=nArq-K7ZiacC, which is incorporated herein by reference in its entirety.

In certain embodiments, calcareous materials made according to the present invention including but not limited to oyster shells are used to make granules for asphalt shingles. In certain embodiments said shingles are whitened and/or have increased reflectivity and/or have increased albedo. In certain embodiments shells produced according to the present invention including but not limited to oyster shells are used as topping in light-colored or solar reflective asphalt. In certain non-limiting embodiments, such asphalt lasts longer than black asphalt due to lower UV degradation and/or being maintain at lower temperature lower tendency to flow. In certain embodiments, the shells or other carbonate materials of the present invention are used in a cement mortar filling voids in the upper part of the pavement to produce heat-reflective pavements. See, e.g., S. Ishiguro and M. Yamanaka, "Heat control of pavement surface temperature using recycled materials," in Third International Conference on Sustainable Construction Materials and Technologies, P. Claisse, E. Ganjian, and T. Naik, Eds., Coventry University and The University of Wisconsin Milwaukee Centre for By-products Utilization, Coventry University and The University of Wisconsin Milwaukee Centre for By-products Utilization, August 2013, and A Comparison of Six Environmental Impacts of Portland Cement Concrete and Asphalt Cement Concrete Pavements by John W. Gadja and Martha G. VanGeem, which are incorporated herein by reference in their entireties. In certain embodiments, calcareous materials including but not limited to oyster shells produced according to the present invention are used as aggregate in pervious concrete. In certain embodiments, calcareous materials produced according to the present invention can be combined with other pre-consumer recycled cementitious materials such as fly ash or blast furnace slag, in construction material compositions. See, e.g., K. N. Kelley, "Use of recycled oyster shells as aggregate for pervious concrete," Master's thesis, University of Florida, 2009, which is incorporated herein by reference in its entirety. In certain embodiments shells produced according to the present invention do not contain detectable amounts of Hg or Pb. In certain embodiments shells, corals, or other carbonate materials produced according to the present invention are used for reef reconstruction. In certain embodiments shells or other carbonate materials produced according to the present invention are sold to the poultry feed industry.

This invention is not limited in its application to the details of construction and the arrangement of components set forth in the description or illustrated in the drawings. The invention is capable of other embodiments and of being practiced or of being carried out in various ways.

The following examples are intended to illustrate, but not limit, the invention.

EXAMPLES

Example 1

*Cupriavidus necator* strain DSM 531 was grown on a mixture of $H_2$ and $CO_2$ and $O_2$ gases as the sole source of energy and carbon for growth.

The following protocol was followed for experiments performed using a mixture of gases in gas tight serum bottles.

Experimental inoculum: 5% by volume, taken from another $H_2$ grown serum bottle culture.

The initial $H_2$ grown serum bottle culture was given 5% inoculation from a Lysogeny broth (LB) grown *Cupriavidus necator* inoculum and grown ~72 hours on $H_2/CO_2/O_2$ gas mix following inoculation from original LB grown culture. Original LB grown inoculum was recovered from glycerol stock stored at −80° C.

Serum bottle growth on gas was performed in 160-ml stoppered and sealed Wheaton glass serum bottles (VWR product number 16171-385). Volume of liquid media was 20 ml. The bottles were plugged with a rubber stopper (VWR #100483-774) and aluminum seal (VWR #89047-008) using Wheaton Hand-Operated Crimper (VWR #80078-996). 20 ml working volume included 19 ml Minimal Salts Medium (MSM), as described in Thermophilic Bacteria, CRC Press, Boca Raton, FL, Jacob K. Kristjansson, ed., 1992, p. 87, Table 4+1 ml inoculum (i.e., 5% inoculum).

The MSM was dispensed in the bottles and gaseous compounds were added as follows: Sterile MSM was transferred into bottles under sterile conditions. 5% gas cultured inoculum was inoculated into the bottles under sterile conditions, and the bottles were plugged with rubber stoppers and sealed. A gas mixture was added at 15 psig to the bottles through a manifold. After the gas mix was added, the seal was crimped with aluminum to seal the serum bottles. The bottles were then placed in a shake flask incubator.

The following experimental results were obtained from 16 serum bottles (14 experimental replicates, 2 controls) incubated at 30° C., 250 RPM. All 16 serum bottles were purged simultaneously with a 67% $H_2$, 24% air (4.8% $O_2$), 9% $CO_2$ gas mix using a manifold as described above. The gas composition run through the manifold was confirmed using gas chromatography (GC) before connecting the serum bottles. Bottles were sacrificed for analysis at 7 time points. The two negative controls were sacrificed at T0 and the last time point respectively. Negative control bottles had identical preparation as experimental bottles minus the inoculum, and were used to detect any contamination and/or abiotic loss or leakage of gas from the bottle headspace. Gas headspace pressure readings samples were taken on negative controls to observe any abiotic $CO_2$ & $H_2$ sorption into the liquid medium and/or gas loss due to leakage.

Sampling and Analytical Procedures

All samples were taken under sterile conditions using syringes and needles for bottle experiments. The optical density (OD) was measured using a Beckman Coulter DU720 UV/Vis spectrophotometer at 650 nm using 100 microliter samples.

At each time point one to three experimental replicate bottles were sacrificed for analysis. Gaseous consumption within the serum bottles was measured using a pressure gauge connected to a needle. The headspace gas pressure was measured for each sacrificed bottle, and a sample of headspace gas was taken by gas tight syringe for gas chromatography (GC) analysis. Analysis of gas headspace samples by GC used a 100-uL sample of headspace gas injected into the GC via gas tight syringe. Gas headspace content of $H_2$, $CO_2$, $O_2$, and $N_2$ in the serum bottles was quantified at each time point. For sampling the broth, the septum of serum bottle was wiped with EtOH and the entire liquid contents of bottle withdrawn into a 30 mL syringe, using bottle pressure. 100 µL of sample was pipetted out for OD measurement at 650 nm. Samples were centrifuged at 12,000 G for 15 min at 4° C. Pellets were resuspended in 10 mL sterile PBS, vortexed, and vacuum filtered through pre-weighed 0.45 μm filters. The filters were dried and filter+biomass retentate weighed to determine biomass dry weight. Dry weights were determined for cells collected on membrane filters (0.45 μm) by drying at 60° C. for 24 hours and cooling to room temperature in a desiccator and weighing. This cycle of drying and re-weighing was continued until the weight remained constant. A correlation was developed between OD and biomass density (dry cell weight per volume).

Figure 2:
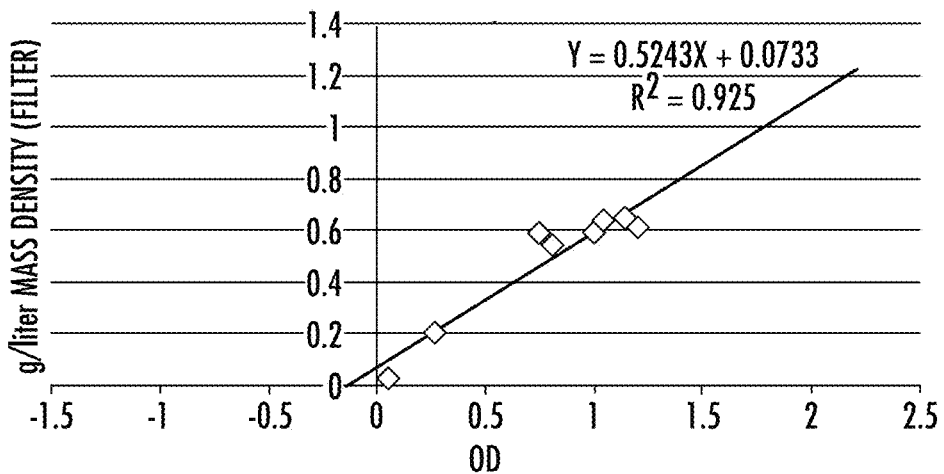
FIG. 2 shows correlation between optical density (OD) and biomass density.
Figure 3:
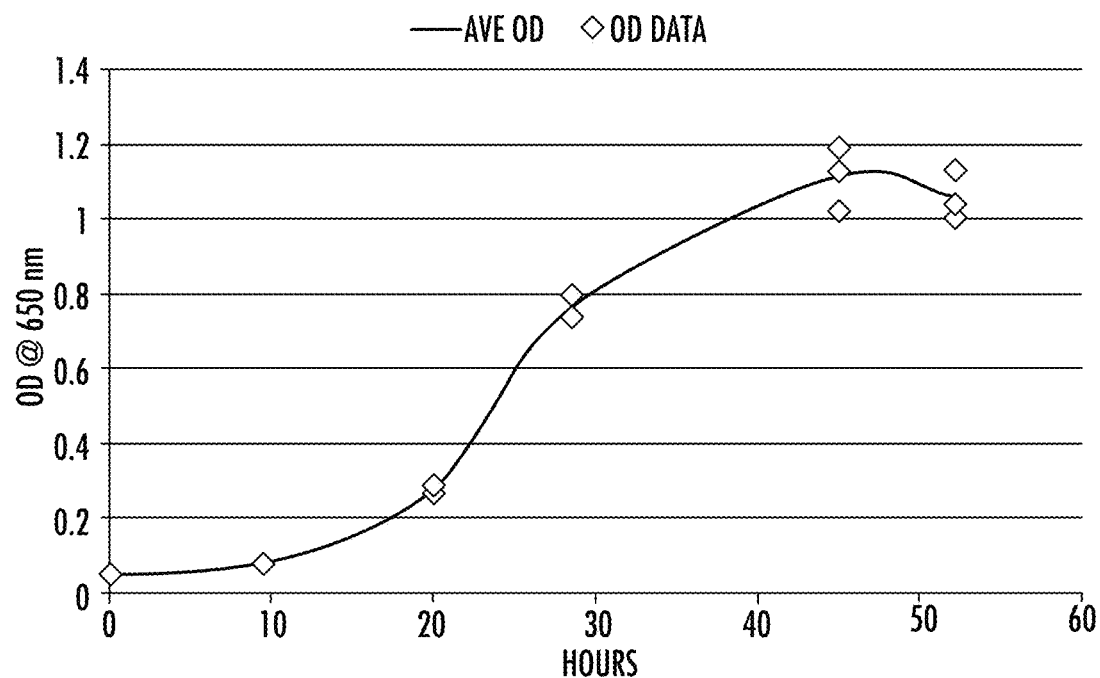
FIG. 3 shows the growth curve for *Cupriavidus necator* in serum bottle growth on gas.
Figure 4:
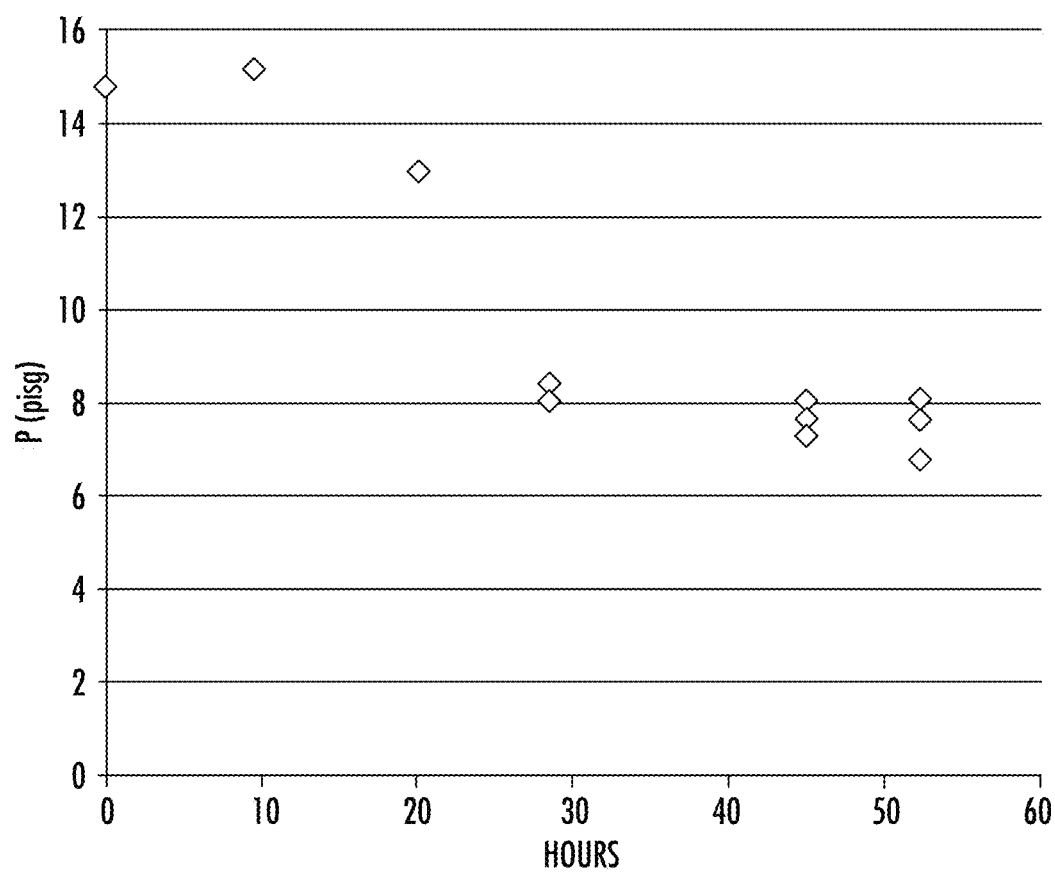
FIG. 4 shows the change in headspace pressure over time for growth of *Cupriavidus necator* in serum bottle growth on gas.

The correlation between OD and biomass density is shown in FIG. 2. The growth curve for this experiment is shown in FIG. 3. The OD measured for individual experimental replicates is represented by the diamond symbols, and the average OD is represented by the solid line. Logarithmic growth occurred between 9 and 30 hours. Change in headspace gas pressure over time due to consumption of the gases by the growing culture is shown in FIG. 4.

Figure 5:
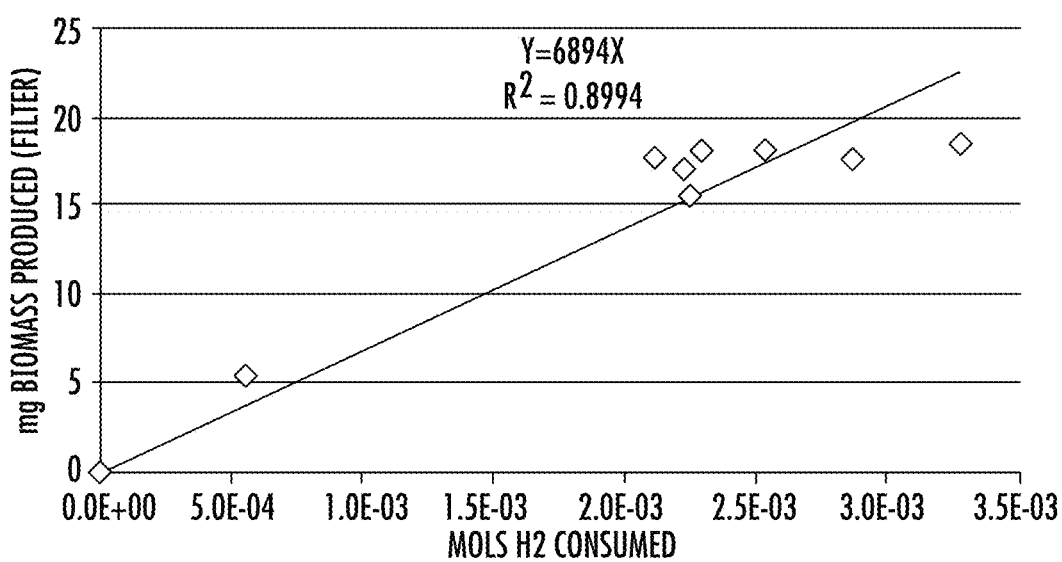
FIG. 5 shows dry biomass produced per moles of $H_2$ consumed for *Cupriavidus necator* in serum bottles.

Assuming the ideal gas law (PV=nRT) for the headspace gases, the total moles of gases were calculated, accounting for temperature variation in sample points. The proportion of each respective gas in the headspace of each bottle was determined by GC. Using the gas headspace results and the measured dry weights, the proportionality of cell weight to moles of H2 consumed was determined. FIG. 5 shows the measured dry biomass for each bottle sacrificed, plotted against the moles of $H_2$ consumed, as determined by headspace pressure measurement and GC analysis for each respective bottle. These results indicated that between 6.7 to 7.2 grams of dry cell mass were synthesized per mole of $H_2$ consumed, or 3.3-3.6 grams cell mass per gram of $H_2$.

Example 2

*Cupriavidus necator* strain DSM 531 was grown to 38 grams per liter dry cell density on a mixture of $H_2$, $CO_2$, and $O_2$ gases as the sole source of energy and carbon for growth.

The following protocol was followed for experiments performed using a mixture of gases including $H_2$, $CO_2$, and $O_2$ in a stirred-tank bioreactor.

Apparatus: Culture was grown in batch, using a custom-manufactured 500 mL glass fermenter with PEEK headplate. Temperature and pH were controlled and monitored with a commercial controller (Electrolab, Fermac 360, United Kingdom). A combination of magnetic stir bars and continuous recycle at 280 mL/min were used for mixing. Recycle could be either withdrawn from the bottom liquid section of the reactor and returned to the headspace through sprayers to control foaming or run in reverse to recycle the headspace gas and foam into the bottom of the broth. Gas supply was from compressed $H_2$, compressed $CO_2$ and house air, each regulated to 20 psi. $H_2$ and air were delivered to a flow proportioner (Matheson G2-4D151-E401/E401, 20 psi), which set the relative fraction of the gases. The $H_2$/air gas mix was then delivered to each fermenter through a variable area flow meter; the flow rate to each fermenter of the same $H_2$/air composition could be adjusted by the needle valve of the flow meter. $CO_2$ gas was split and delivered to individual variable area flow meters at each fermenter. The $CO_2$ and $H_2$/air lines tee into a single line delivered to the fermenter. A pressure gauge was used to monitor the gas delivery pressure to the fermenter. Gas was mixed into the fermenter broth via four 2-micron diffusion stones (p/n KEG592, http://morebeer.com/products/diffusion-stone-2-micron-oxygen.html), and vented from the reactor via a condenser to a foam-overflow bottle, then to an exhaust system.

Medium: The medium used for this experiment is described in Example 1. pH control was performed with 2N $NH_4OH$ or 2N NaOH. 2N $NH_4OH$ was prepared from 5 M $NH_4OH$, Fluke 318612 (kept at 4° C.) (120 mL)+autoclaved milliQ-$H_2O$ (180 mL).

Autotrophic inoculum: *Cupriavidus necator* DSM 531 inoculum was taken from $H_2/CO_2/O_2$ grown serum bottle culture. Inoculum was prepared from preserved 0.5 mL glycerol stocks stored at −80 C for the DSMZ 531 strain. Revival cultures were started on $H_2/CO_2/O_2$ gas mix per the serum bottle protocol described in Example 1, with 0.5 mL glycerol stock added to 20 mL minimal salts medium (MSM) in a gas tight serum bottle. This initial serum bottle was then subcultured, 1 mL to 20 mL fresh MSM, into 2 serum bottles under the standard $H_2/CO_2/O_2$ gas headspace. These serum bottles were incubated at 30° C., 250 RPM. The initial revival from the glycerol stock on gas took 2 days and the subculture took another day to grow. The two serum bottle cultures were provided as inoculum for the bioreactor. Optical density (OD) of inoculum was taken as well as a sample for DNA analysis. The gas grown inoculum had an OD ~1. The fermenter was inoculated to give an initial OD ~0.1. In other words, the serum bottle broth was diluted in the bioreactor at a 1:10 ratio. Inoculum was transferred from serum bottles to the bioreactor using a 60 mL syringe. After inoculation, a To OD was taken. Generally, all OD measurements were performed with a Beckman Coulter DU720 UV/Vis spectrophotometer.

Fermenter Operation:
Base addition—pH was controlled with 2N $NH_4OH$
Foam Control—If foaming filled more than ½ headspace, and was not controlled by headspace spraying or recirculation, then anti-foam was used. (A8011, Sigma Antifoam C Emulsion)
Nutrient amendment—In addition to nitrogen nutrient provided by base addition of $NH_4OH$, other mineral nutrients were added during the run so as to prolong growth and prevent any mineral nutrient limitations from occurring.

Figure 6:
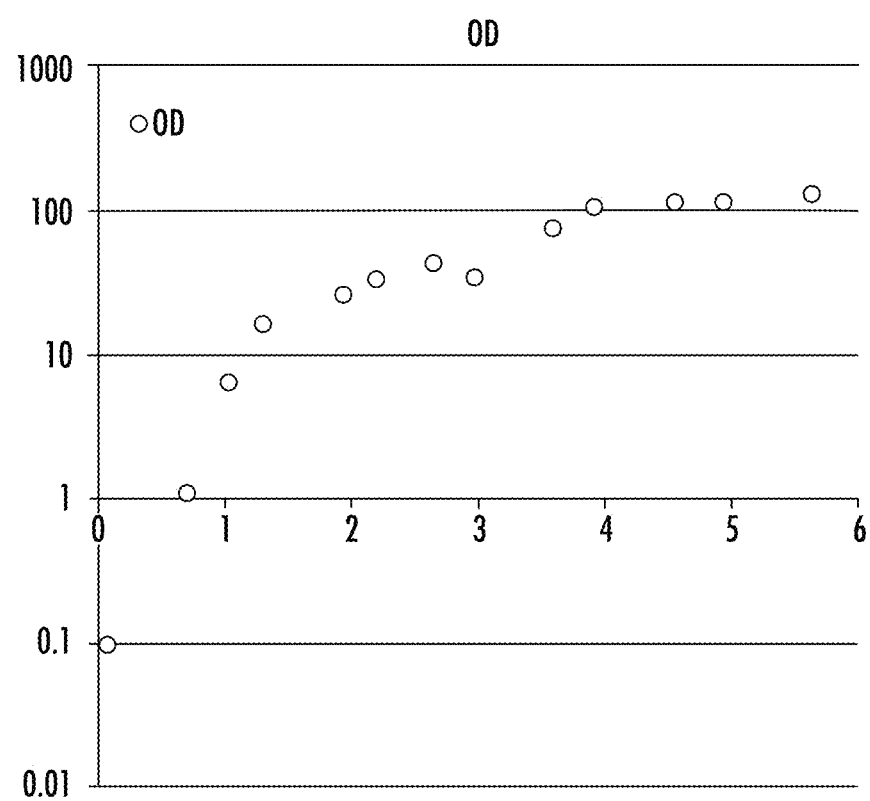
FIG. 6 shows the growth curve for the knallgas microorganism *Cupriavidus necator* grown on $H_2/CO_2/O_2$ in a bioreactor.

FIG. 6 gives an example of a growth curve for the knallgas microorganism *Cupriavidus necator* grown on $H_2/CO_2/O_2$ gas substrate according to this protocol. The final OD measured at 650 nm was 132 and the final dry biomass density was 38 grams/liter from growth on $H_2/CO_2/O_2$ gas substrate. Log growth lasted the first day and a half; however the biomass was still accumulating at a linear rate at the termination of the run during day five.

Example 3

Microorganisms from the genus *Rhodococcus* and from the genus *Cupriavidus* were tested for their ability to grow on different carbon sources (FIG. 7). Colonies from strains grown on LB agar plates at 30° C. were transferred into flasks containing 10% (v/v) of the indicated media for 3-20 days at 30° C. and 250 rpm. *R. opacus* strain DSM 44193 exhibited growth only under heterotrophic growth conditions as measured by optical density (OD) at 650 nm on MSM medium (1 L Medium A: 9 g $Na_2HPO_4·12H_2O$, 1.5 g $H_2PO_4$, 1.0 g $NH_4Cl$ and 0.2 g $MgSO_4·7H_2O$ per 1 L; 10 ml Medium B: 50 mg Ferric ammonium citrate and 100 mg $CaCl_2$) per 100 ml; 10 ml Medium C: 5 g $NaHCO_3$ per 100 ml; and 1 ml Trace Mineral Solution: 100 mg $ZnSO_4·7H_2O$, 30 mg $MnCl_2·4H_2O$, 300 mg $H_3BO_3$, 200 mg $CoCl_2·6H_2O$, 10 mg CuCl$_2$·2H$_2$O, 20 mg NiCl$_2$·6H$_2$O and 30 mg Na$_2$MoO$_4$·2H$_2$O per 1 L) supplemented with 40 g/L glucose. *R. opacus* strain DSM 43205 showed identical growth rates under heterotrophic conditions reaching O.D=9.0. Strain DSM 43205 was also able to grow on chemoautotrophic conditions (MSM medium supplemented with 66.7% H$_2$, 9.5% CO$_2$, 5% O$_2$ and 18.8% N$_2$). *Rhodococcus* sp. (DSM 3346) exhibited growth under heterotrophic conditions and chemoautotrophic conditions (DSMZ Medium 81: 1 L of Mineral Medium for chemolithotrophic growth: 2.9 g Na$_2$HPO$_4$·2H$_2$O, 2.3 g KH$_2$PO$_4$, 1.0 g NH$_4$Cl, 0.5 g MgSO$_4$·7H$_2$O, 0.5 g NaHCO$_3$, 0.01 g CaCl$_2$·H$_2$O and 0.05 g Fe(NH$_4$) citrate per 1 L; and 5 ml Trace Mineral Solution, supplemented with 80% H$_2$, 10% CO$_2$ and 10% O$_2$). *Cupriavidus necator* (DSM 531) was able to grow under heterotrophic and chemoautotrophic conditions (media described for Strain DSM 43205) (FIG. 7). *Cupriavidus necator* (DSM 531) transformed with pSeqCO2 was able to grow on LB media supplemented with 300, 400, and 500 μg/ml kanamycin exhibiting OD600 of 1.47, 1.52 and 1.51 respectively. Untransformed cells exhibited growth on control (LB only) and some growth on 300 μg/ml kanamycin while no growth was detected on 400 and 500 μg/ml kanamycin.

Example 4

In one group of experiments, colonies from *Rhodococcus* strains grown on LB agar plates at 30° C. were transferred into gas tight serum bottles containing the indicated growth media and gas mixtures. (Original LB grown inoculum was previously recovered from glycerol stock stored at −80° C.). Serum bottle growth on gas was performed in 160-ml stoppered and sealed Wheaton glass serum bottles (VWR product number 16171-385). Volume of liquid media was 10 to 20 ml. The bottles were plugged with a rubber stopper (VWR #100483-774) and aluminum seal (VWR #89047-008) using Wheaton Hand-Operated Crimper (VWR #80078-996). Sterile growth media was transferred into bottles under sterile conditions. Inoculum was introduced to bottles under sterile conditions, and the bottles were plugged with rubber stoppers and sealed. A gas mixture was added to the bottles. After the gas mix was added, the seal was crimped with aluminum to seal the serum bottles. The bottles were then placed in a shake flask incubator. The bottles were incubated at 30° C., 250 RPM. All samples were taken under sterile conditions using syringes and needles. Growth was assessed by measurement of optical density (OD) in a spectrophotometer at 650 nm.

*Rhodococcus opacus* strain DSM 43205 exhibited growth under chemoautotrophic conditions in the following media: MSM medium (1 L Medium A: 9 g Na$_2$HPO$_4$·12H$_2$O, 1.5 g H$_2$PO$_4$, 1.0 g NH$_4$Cl and 0.2 g MgSO$_4$·7H$_2$O per 1 L; 10 ml Medium B: 50 mg Ferric ammonium citrate and 100 mg CaCl$_2$ per 100 ml; 10 ml Medium C: 5 g NaHCO$_3$ per 100 ml; and 1 ml Trace Mineral Solution: 100 mg ZnSO$_4$·7H$_2$O, 30 mg MnCl$_2$·4H$_2$O, 300 mg H$_3$BO$_3$, 200 mg CoCl$_2$·6H$_2$O, 10 mg CuCl$_2$·2H$_2$O, 20 mg NiCl$_2$·6H$_2$O and 30 mg Na$_2$MoO$_4$·2H$_2$O per 1 L), supplemented with a gas mixture that contained 66.7% H$_2$, 9.5% CO$_2$, 5% O$_2$ and 18.8% N$_2$. The liquid volume was 20 mL and the gas headspace volume was 140 mL.

*Rhodococcus* sp. DSM 3346 exhibited growth under chemoautotrophic conditions in the following media: DSMZ Medium 81 (1 L of Mineral Medium for chemolithotrophic growth: 2.9 g Na$_2$HPO$_4$·2H$_2$O, 2.3 g KH$_2$PO$_4$, 1.0 g NH$_4$Cl, 0.5 g MgSO$_4$·7H$_2$O, 0.5 g NaHCO$_3$, 0.01 g CaCl$_2$·2H$_2$O and 0.05 g Fe(NH$_4$) citrate per 1 L; and 5 ml Trace Mineral Solution), supplemented with a gas mixture that contained 80% H$_2$, 10% CO$_2$ and 10% O$_2$. The liquid volume was 10 mL and the gas headspace volume was 150 mL.

Figure 8:
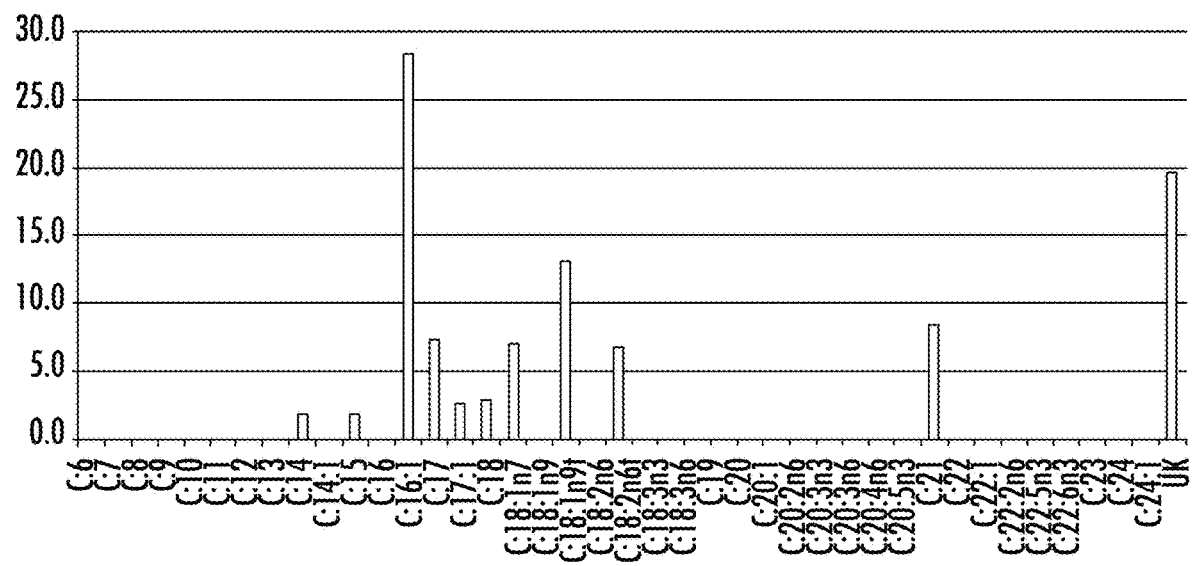
FIG. 8 shows the fatty acid profile for *Rhodococcus opacus* DSM 43205.
Figure 9:
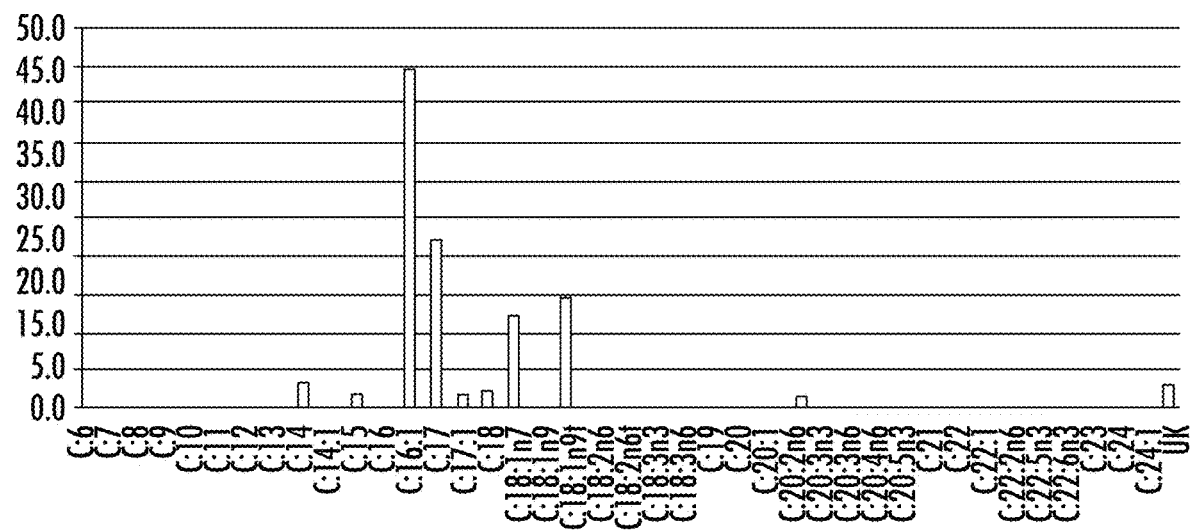
FIG. 9 shows the fatty acid profile for *Rhodococcus* sp. DSM 3346.

Cells were harvested after 72 hours, and profiles of fatty acids contained in neutral lipids, such as triacylglycerol (TAG), produced by each strain were determined by gas chromatography and mass spectrometry (GC/MS). The fatty acid profile for DSM 43205 is shown in FIG. 8, and the fatty acid profile for DSM 3346 is shown in FIG. 9. FIGS. 8 and 9 show specific fatty acid chain types on the x-axis versus the percentage that each respective fatty acid chain type contributed to the total amount of fatty acids recovered from the neutral lipid fraction, which is given on the on the y-axis. DSM43205 produced 36%, 6% and 27% of 16, 17 and 18-carbon fatty acids, respectively, as a fraction of the total fatty acids. DSM 3346 produced 66%, 4%, and 27% 16, 17, and 18-carbon fatty acids, respectively, as a fraction of the total fatty acids.

Example 5

*Rhodococcus opacus* strain DSM 43205 was cultured in a bioreactor using MSM media, as described above, and a H$_2$/CO$_2$/O$_2$ gas mixture. The composition of the gas mixture was 66.7% H$_2$, 9.5% CO$_2$, 5% O$_2$ and 18.8% N$_2$. The cell mass was separated from the supernatant of the culture by centrifugation. The supernatant was discarded and a chloroform/methanol (C/M) extraction was performed on the biomass pellet. Gravimetric analysis of the crude extract from the biomass showed 40% of the biomass comprised lipids that are soluble in chloroform/methanol, and 14% comprised lipids that are soluble in hexane. Lipids were applied to Silica-60 columns, and different lipid groups were separated and eluted from the column with organic solvents including hexane, chloroform, isopropanol, methanol and acetone. Mild alkaline methylation was performed to methylate non-fatty acid lipids and acid methylation was performed to methylate fatty acids. Fatty acid methyl esters (FAMEs) were analyzed by gas chromatography-mass spectrometry (GC-MS).

For FAME analysis, compounds were detected on an Agilent 6890N GC/MS (Agilent, Santa Clara, CA) on a HP1 60 m column×0.25 mm ID. Samples were placed in GC vial inserts with a final volume in hexane of 50• L. Samples were injected using an automatic injector, the injector temperature was 250° C. and was run in split mote (8:1) with an initial GC temperature of 100° C., ramp at 10° C./min to a final temp of 150° C., then a ramp of 3° C./min to 250° C., finally a 10° C./min ramp to 312° C. which is held for 7 min. Peak ID was accomplished through a NIST08 library and comparison to known standards (Supelco 37 Component FAME Mix). Quantification was accomplished through an external standard added to each sample prior to injection (methyl undecanoate) and extraction efficiency was quantified by an internal standard (1,2-dinonadecanoyl-sn-glycero-3-phosphocholine).

The GC-MS analysis revealed that *Rhodococcus opacus* strain DSM 43205 cultured with the gas mixture produced triacylglycerols, which contained high amounts of omega-7 fatty acids, including palmitoleic acid (C16:1, also known as 9-hexadecenoic acid) and vaccenic acid (C18:1, also known as 11-octadecenoic acid). Further analysis of the lipid content showed, as a fraction of the total fatty acid content, 13%

C16:1 omega 7 fatty acid (palmitoleic acid) and 21% C18:1 omega 7 fatty acid (vaccenic acid).

Example 6

*Rhodococcus opacus* strain DSM 43205 was grown on a mixture of $H_2$ and $CO_2$ and $O_2$ gases as sole sources of energy and carbon for growth in a one-liter bottle. Inoculum was recovered from a water+MSM stock aliquot stored at −80° C. The medium used was MSM, as described above. An aliquot from stock stored at −80° C. was inoculated into MSM (20 ml) in a small serum bottle. Serum bottle growth on gas was performed as described above in a 160-ml stoppered and sealed Wheaton glass serum bottle, with a gas mixture consisting of 67% $H_2$, 24% air (4.8% $O_2$), 9% $CO_2$. The bottle was placed in a shake flask incubator and incubated at 30° C., 250 RPM.

Following roughly 72 hours of growth, a high density subculture inoculum was prepared from the gas serum bottle culture by centrifuging and resuspending in fresh MSM. The high density inoculum was inoculated into 100 ml MSM in a 1 L glass bottle with a gas tight cap, having two valves which allowed inflow and outflow of gas. A gas mixture in the following ratio was provided to the headspace of the 1 L bottle: $H_2$: 71%; $O_2$: 4.2%; $N_2$: 15.8%; $CO_2$: 9.0%.

Following gas addition, the sealed one-liter bottle was placed in a shake flask incubator at 28° C. and 200 rpm. The gases were refreshed once per day. The culture grew on gas until a final OD at 650 nm was reached of OD=1.27.

DNA sequencing was performed on the final recovered cells following growth on gas in the 1 L bottle to confirm strain identity of the final culture. 16S rRNA sequences were determined using 27F and 800R primers. With both primers, the top BLAST hits were identified as *Rhodococcus* sp., *Rhodococcus opacus*, *Rhodococcus wrastislaviensis*, GenBank numbers EU127452.1, AB032565.1, and AY940038.1, respectively.

Example 7

Numerous oxyhydrogen species are publicly available or may be isolated using techniques that are described herein. For example, at least 238 different *Rhodococcus* strains and at least 55 different *Cupriavidus* strains are available from public DSMZ (Deutsche Sammlung von Mikroorganismen und Zellkulturen GmbH) strain depositories as well as strains from many other genera that include oxyhydrogen microorganisms including *Hydrogenovibrio*, *Rhodopseudomonas*, *Hydrogenobacter*, *Xanthobacter*, and *Hydrogenothermus*. Oxyhydrogen strains may also be obtained by routine processes, such as isolation from soil samples or geothermal fluid samples using enrichment methods.

Testing of strains for oxyhydrogen growth and the ability to produce organic compound including those with carbon number C5 or greater including but not limited to amino acids and proteins under the claimed chemosynthetic conditions are routine in the art. For example, the ability of a *Rhodococcus* strain to grow under oxyhydrogen conditions using $CO_2$ as a carbon source could be performed as described above in Examples 4-6. Other methods for growing under oxyhydrogen (knallgas) conditions using $CO_2$ as a carbon source are described in "Thermophilic bacteria," Jakob Kristjansson, Chapter 5, Section III, CRC Press, 1992, pp. 86-88, and have been found to work well with a wide variety of strains drawn from a wide range of genera. Assessment of production of organic compounds, such as those chemosynthetically produced by oxyhydrogen species, is also routine in the art. For example, gas chromatography and mass spectrometry (GC/MS) may be used, as described in Example 5. Other methods include lipid extraction, thin layer chromatography (TLC), gas chromatography (GC), high performance liquid chromatography (HPLC), and mass spectrometry (MS), as described in Waltermann et al. (2000) "*Rhodococcus opacus* strain PD630 as a new source of high-value single-cell oil? Isolation and characterization of triacylglycerols and other storage lipids" *Microbiology* 146:1143-1149.

Example 8

Approximately five kilograms of biomass (dry weight) was produced by *Cupriavidus necator* strain DSM 531 grown on a mixture of $H_2$, $CO_2$, and $O_2$ gases as the sole source of energy and carbon for growth. From this biomass a hexane soluble oil was extracted and analyzed. The following protocol was used in producing the biomass from $H_2$, $CO_2$, and $O_2$ feedstocks in stirred-tank bioreactors and then extracting the oil from the biomass.

Apparatus: *C. necator* cultures were grown in batch, using two 20-liter reactors from Applikon Biotechnology (Applikon).

Bioreactor: Each bioreactor consisted of a glass vessel mounted on a support stand with a stainless steel head plate having an elastomeric seal. The head plate had ports for numerous feed-throughs, all of which had an elastomeric seal to prevent the leakage of gas into or out of the reactor. These feed-throughs allowed for thermowells, pH probes, dissolved oxygen probes, gas inlets, liquid inlets, gas outlets, liquid sampling ports, and more to all be mounted on the head plate.

Bioreactor Sensors: A temperature probe located in a thermowell was used to monitor the temperature and to allow for control of a heater. A pH probe was used to monitor the pH and, if needed, control the addition of higher or lower pH buffered solutions to the reactor. A foam sensor was used to control the addition of anti-foam. A dissolved oxygen probe was used measure the oxygen levels in the reactor liquid and could be used to control agitation or open/close the gas flow to the reactor. All of the sensors were powered by, controlled by, and provided inputs to the bioreactor controller/console.

Stirring: A stirrer passed through the head plate with a complete seal and magnetic coupling. The stirrer had an external motor that was a separate item that fit around the external portion of the stir shaft. The motor speed was controlled by an external controller that allowed for precise control of the rotational speeds.

Heating/Cooling: The reactor was heated by an external electric heating blanket, which used a closed-loop proportional-integral-derivative controller (PID) controlled by the Pt 100 temperature probe via the bioreactor system controller. To maintain temperatures, a cooling finger was also plumbed to prevent overheating of the media by the stirrer motor.

Bioreactor Mounting: The bioreactor systems were mounted on metal tripod holders. Clamps or chains were used to attach this tripod to the strut mountings located inside of a fume hood to prevent the reactor from being knocked over. The whole tripod and reactor setup was placed in a shallow plastic container to provide secondary containment.

Figure 10:
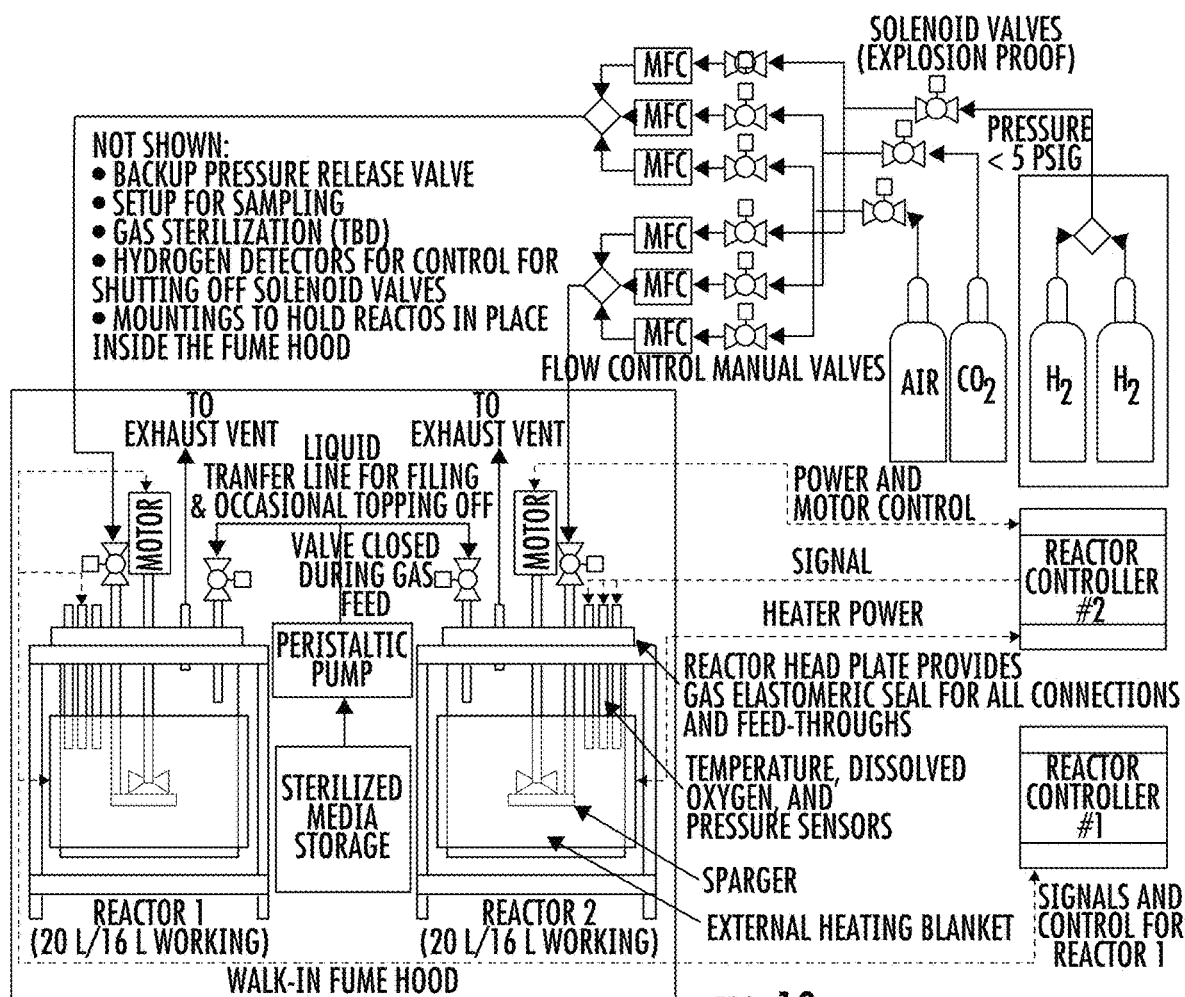
FIG. 10 shows a schematic diagram of the bioreactors and supporting systems used to grow *C. necator* on gas.
Figure 11:
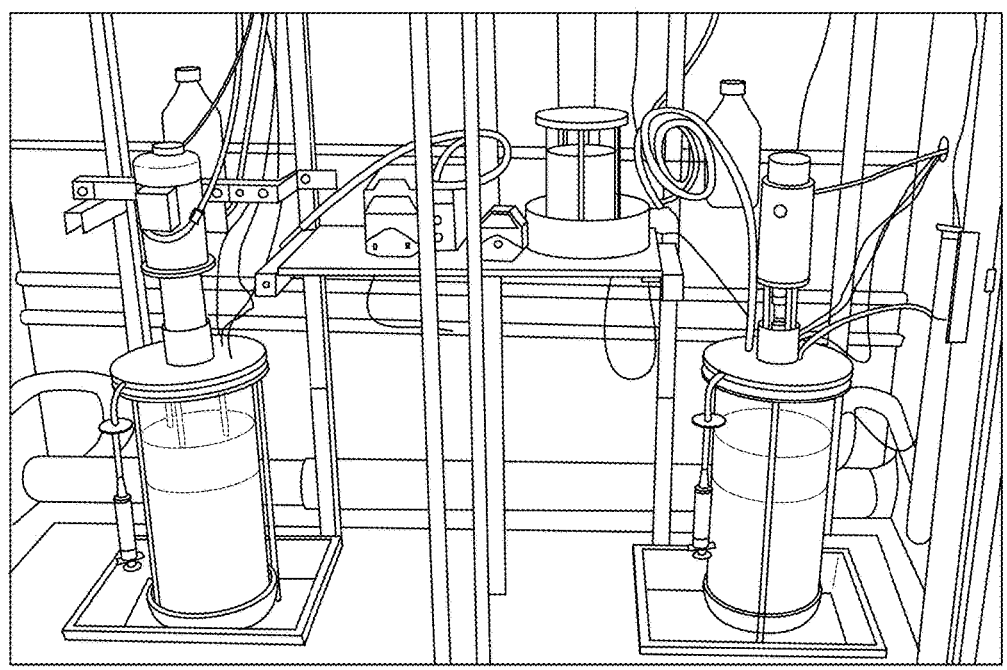
FIG. 11 shows two 20-L bioreactors growing *C. necator* on gas in a fume hood.

A schematic diagram of the bioreactors and supporting systems is shown in FIG. 10. The two 20-L bioreactors were located in a fume hood as shown in FIG. 11. The bioreactors were installed inside of a fume hood to contain releases of hydrogen gas. All of the controls and gas sources were located outside of the fume hood as well as the gas cylinders, reactor controllers, mass flow meters, hydrogen sensors, and gas control valves. Shown in FIG. 11 are the two 20-liter reactors in use during growth of C. necator on $H_2$, $CO_2$, and $O_2$ gases as the sole source of energy and carbon.

Figure 12:
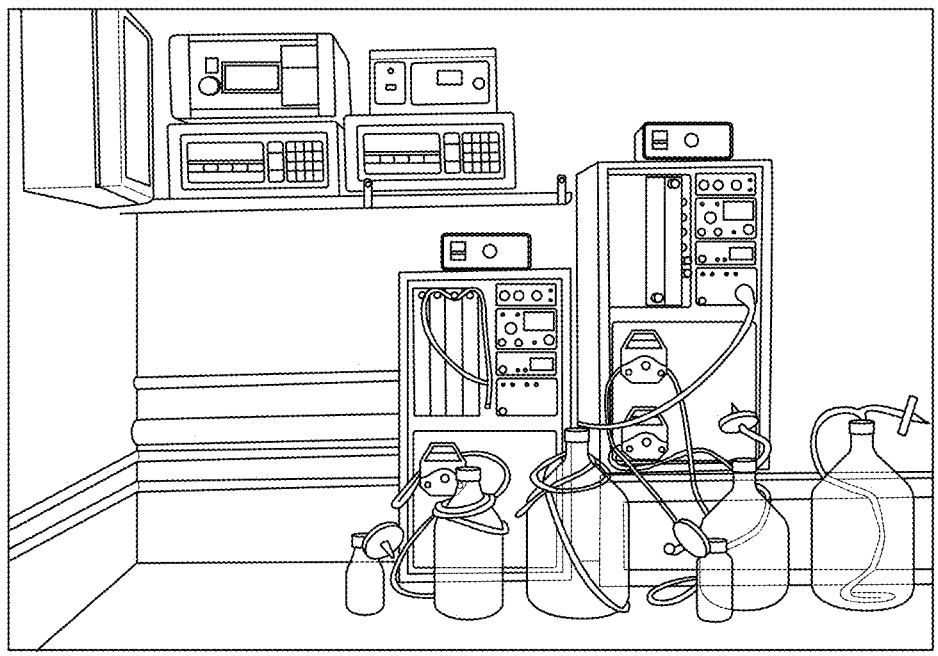
FIG. 12 shows Applikon controllers and consoles that were used to operate the reactors in FIG. 11 along with explosive gas detection system, mass flow meters, level controllers, base control reservoirs, media addition reservoir, and foam control reservoir.

Controller/Console: The bioreactor system controller/console contained the components that controlled and operated the bioreactor system. These units provided the power, temperature control, stirring control, received inputs from the sensors, turned on and off the feed pumps (acid, base, anti-foam, and additional nutrients) based on sensor inputs, and were used to turn on/off the gas flows with solenoid valves and rotameters. Due to the lack of all stainless steel components, these units were not used to control the hydrogen to minimize the risk of hydrogen leaks. The controller/console units were located outside of the hood away from the bioreactors to minimize exposure to hydrogen in case of a leak and to minimize the time operators spend working directly around the bioreactors. FIG. 12 shows the Applikon controllers and consoles that were used to operate the reactors. Included in FIG. 12 are the controllers, consoles, stirrer controls, explosive gas detection system, mass flow meters, level controllers, base control reservoirs, media addition reservoir, and foam control reservoir. All of the reactor controls were located outside of the hood.

Gas Delivery: The gas was delivered into the lower portion of the bioreactor though a sparger setup that passed through the head plate. A valve located just outside the reactor enabled the gas flow to be manually shut off at each reactor separately. The gas feed line plumbed to the reactor was a flexible stainless steel line with a 0.2-micron filter installed at the reactor head to minimize possible contamination. Mass flow meters located outside of the hood were used to control the flow rates to the reactors. Lines between the cylinders and mass flow meters had both manual and solenoid valves for both manual and automatic shutoff of gases. The solenoid valves were connected to explosive gas sensors that automatically shut off gas flows when hydrogen was detected in lab or in the hood.

Gas Storage: A gas cabinet was used to store the hydrogen cylinders. The gas cabinet was mounted in place and included ventilation and sprinklers. The cabinet included enough room to store multiple cylinders to allow for easy switching between an old to a new cylinder.

Safety Controls: Explosive gas detectors were used to determine the presence of hydrogen in the lab. Multiple sensors were located in strategic positions around the lab and in the hood. These gas detectors were configured to shut off the solenoid valves on the gas delivery lines if hydrogen was detected, which shuts off the flow of gas to the reactors.

Peristaltic Pump: An additional peristaltic pump was located in the hood. This pump was used to transfer fresh media into the reactors at the start of a batch run and used to remove the media and biomass at the end of a batch run.

Media Storage: Plastic carboys or glass bottles were used to store the fresh media and the biomass recovered after a batch run.

Medium: The MSM medium used for this experiment is described in Thermophilic Bacteria, CRC Press, Boca Raton, FL, Jacob K. Kristjansson, ed., 1992, p. 87, Table 4.

Inoculum: *Cupriavidus necator* inoculum was prepared from preserved 0.5 mL glycerol stocks stored at −80 C for the DSMZ 531 strain. Revival cultures were started on $H_2/CO_2/O_2$ gas mix per the serum bottle protocol described in Example 1, with 0.5 mL glycerol stock added to 20 mL minimal salts medium (MSM) in a gas tight serum bottle. The inoculum was provided in multiple containers, which were combined inside of a biosafety cabinet into a single sterile media bottle outfitted with a sterile transfer cap assembly. An OD and streak of the inoculum was taken. The inoculum was then transferred into the reactor using sterile transfer tubing and a peristaltic pump. After inoculating the reactor, a starting OD of the batch was taken using the sample assembly.

Media Preparation and Addition: All of the media was prepared using the recipes provided in Thermophilic Bacteria, CRC Press, Boca Raton, FL, Jacob K. Kristjansson, ed., 1992, p. 87, Table 4, except at the larger quantities required for 20-liter scale. The main media component (A) was prepared in 20-liter Nalgene carboys outfitted with sterile liquid transfer cap and filter assemblies. The media was autoclaved in the carboys and transferred into the autoclaved reactors using sterile tubing and peristaltic pumps to avoid contamination. The smaller media components (B and D) were prepared in large reservoirs and were sterilized by syringing the solutions through a single-use, sterile 0.2-micron filter directly into the reactor using the septa. Using the septa minimized the risk of contamination as it allowed the opening of the reactor to be avoided. A fourth smaller media component (C) was handled in a manner similar to A, in that a larger reservoir outfitted with a sterile transfer cap was prepared with media, autoclaved, and the media was transferred using sterile tubing and a peristaltic pump.

Bioreactor Preparation and Start-up: Prior to starting freshly inoculated batches, the bioreactor was prepared for autoclaving. The reactor head plate was mounted in place. Transfer lines were connected, clamped, and the end was covered with foil and sealed with autoclave tape. A 0.2-micron filter was connected to the gas inlet of the sparger to sterilize the incoming gases. A vent line was clamped and sealed with foil. The thermowell, condenser, foam level probe, cooling coil, sampling apparatus, adjustable liquid draw tube, and dissolved oxygen probe were installed. The port for the pH probe was covered and sealed with foil. The reactor was then autoclaved for 60 minutes at 131° C. with a dry cycle. The pH probe was sterilized with a combination of quick flaming, ethanol, and UV light. After the bioreactor was autoclaved and cooled to room temperature, the pH probe was inserted into the reactor while both the reactor and probe were inside a biosafety cabinet. The reactor was then mounted in the hood; i.e. cooling lines, transfer lines, electronic controls, heater, stirring motor, etc. were all connected. As quickly as possible, media component A was transferred into the reactor to minimize the amount of time that the pH probe was dry. The temperature control and stirring were turned on, and if necessary, the cooling water as well. Once the temperature of the media reached the desired temperature, media components B, C, and D were transferred into the reactor via the methods described above. The pH control was then started.

Inoculating Bioreactor: Fresh inoculation was performed as described above. In a number of runs the media and biomass from the previous batch was removed via peristaltic pump except for a residual volume, typically less than one liter, which was used to inoculate the next batch. When inoculating with residual volume from the previous batch, after removal of the bulk of the culture, sterile media component A at room temperature was transferred into the bioreactor and the heating was turned on. The rest of the media components B, C, and D were then transferred in via the methods described above. Then the gas flow was turned on, stirring turned up, and pH control turned on. At this point, the run was considered to have started and a starting OD was taken. After the reactor reached the operational temperature the cooling was turned on.

Gas Composition and Flow Rates: The gas composition was 66.7% $H_2$, 23.8% air, 5% $O_2$, 9.5% $CO_2$. The ratios were controlled using mass flow controllers. The gas flow rates ranged from 0.05 to 0.3 VVM of total gas flow. Typical flow rates were 0.05 VVM over the weekends and 0.2 VVM during the week when both reactors were in operation and had foam control. In the runs that did not use foam control, typical values of 0.05 to 0.075 VVM were used to reduce the foam to manageable levels.

pH Control: Ammonium hydroxide (2.0 M) was used to control the pH of the media in the bioreactor. The ammonium hydroxide solution was prepared by autoclaving 1200 mL of MilliQ water in a 2-liter media bottle outfitted with a sterile transfer cap and filter assembly and adding 800 mL of filter-sterilized 5.0 M ammonium hydroxide inside of a biosafety cabinet. The ammonium hydroxide was automatically transferred into the reactor via peristaltic pump, which was controlled by the bioreactor controller using the pH probe signal.

Nutrient Addition/Amendment: The nutrient amendment solutions used were the same as those used for the initial media, however with different quantities. Mineral nutrients were added during the run so as to prolong growth and prevent any mineral nutrient limitations from occurring. The amendment solutions were either added directly into the reactor using a syringe and sterilizing through a 0.2-micron filter or added through sterile tubing that remained connected to the reactor using a peristaltic pump. The total reactor volume was also manually adjusted on a regular basis (typically daily) by removing small portions of the reactor media and biomass to maintain a working volume of approximately 15.5 L. This was done to compensate for the water additions from the nutrient amendments and water generation by the cellular respiration in order to maintain stable mixing kinetics and prevent overflow.

Sampling: Small aliquots of the media solution were taken at regular intervals from the bioreactor via the liquid sample assembly. These were used to perform the OD600 measurements on an Eppendorf Biophotometer Plus as well as provide the microfuged samples for DNA analysis. The microfuged samples were spun at 10000 rpm for 10 min and, decanted, and stored at −20° C.

Foam Control: After reaching an OD of approximately 15, foam would start to fill the headspace and if not controlled the foam would easily fill up the 2 liter overflow reservoir overnight when gas flow rates of 0.2 VVM were used. A foam sensor was used to determine the presence of foam and turn on a pump that would deliver a solution of silicon-based antifoam emulsion. Gas flow rates and stirrer speeds were adjusted as necessary in batches 11 and 12 to prevent excessive foam build-up. At gas flow rates of 0.05 VVM to 0.075 VVM, the bioreactors were able to be operated without anti-foam. However, the foam would fill the headspace; causing a small amount to flow into the foam overflow container via the gas outlet.

Temperature, pH, and GD were monitored and recorded. Cell purity was monitored using streak plates. A total of 9 batches at the 20-liter scale using *C. necator* were

TABLE 1

The results of a series of batch runs for *C. necator* at 3-liter and 20-liter scale.

| Batch # | Scale | Reactor | Start Date | End Date | Start OD | Final OD | Duration (Hrs) | Total gas range (VVM) | Stirring rate range (rpm) | Inoculant |
|---|---|---|---|---|---|---|---|---|---|---|
| 1 | 3 L | | 9/4 | 9/6 | 0.63 | 28 | 57.7 | 0.1-0.5 | 850 | 240 ml of gas grown *C. necator* from serum bottles |
| 2 | 3 L | | 9/9 | 9/13 | 2.96 | 32.4 | 103 | 0.2-1 | 900 | ~200 ml of batch 1 |
| 3 | 3 L | | 9/16 | 9/20 | 5 | 40 | 99.9 | 0.2-1 | 1000-1200 | ~200 ml of batch 2 |
| 4 | 20 L | A | 9/23 | 10/3 | 0.94 | 42 | 248 | 0.1-0.3 | 600-800 | ~600 ml of batch 3 |
| 5 | 20 L | B | 10/1 | 10/9 | 1.1 | 6.7 | 188 | 0.05-0.2 | 200 | ~650 ml of batch 4 |
| 6 | 20 L | A | 10/4 | 10/11 | 0.085 | 42 | 165 | 0.05-0.2 | 800-900 | ~400 ml of sugar grown *C. necator* from flasks |
| 7 | 20 L | B | 10/11 | 10/18 | 1.2 | 50 | 168 | 0.05-0.2 | 200-850 | ~500 ml of batch 6 |
| 8 | 20 L | A | 10/11 | 10/18 | 2.1 | 42.5 | 167 | 0.05-0.2 | 800-980 | <1 L of batch 6 |
| 9 | 20 L | B | 10/18 | 10/25 | 3.5 | 49.4 | 165 | 0.05-0.2 | 750-850 | <1 L of batch 7 |
| 10 | 20 L | A | 10/18 | 10/24 | 1.9 | 39.2 | 143 | 0.05-0.2 | 800-950 | <1 L of batch 8 |
| 11 (S1) | 20 L | A | 11/1 | 11/7 | 2.34 | 29.2 | 143 | 0.04-0.2 | 800-850 | ~750 ml of batch 12 |
| 12 | 20 L | B | 10/25 | 11/5 | 0.56 | 37.3 | 264 | 0.05-0.1 | 500-750 | <500 ml of batch 10 | performed. The final optical densities (ODs) of the batches were typically between 30 and 50. The results of these 20-liter batches are summarized in the Table 1 below.

Eight of the batches reached a final OD of higher than 39, one that was run with lower gas flows (#11) achieved an OD of 30, and one batch that was limited to low stirring rates (#5) only reached an OD of 6.7. The highest OD achieved was 50 in batch #7. All biomass grown was centrifuged out of the culture broth.

Biomass Centrifuging and Storage: A Beckman Coulter Allegra X-12R centrifuge was used to centrifuge the broth harvested from a batch run to recover the biomass. The Allegra-12R has refrigeration down to −10° C. and is outfitted with a SX4750 swinging bucket rotor capable of 3,750 rpm and has a 3-L capacity. After a batch, the biomass and media were transferred out of a bioreactor using a peristaltic pump into 10-liter polypropylene jerry cans. The jerry cans of biomass and media were stored in a refrigerator until they were centrifuged. The biomass was centrifuged 3 liters at a time split between four 750-mL polycarbonate centrifuge bottles. The centrifuge was operated 3,750 rpm at 4° C. for 30 minutes. The supernatant was decanted off and sterilized with bleach prior to disposal. The dewatered biomass for a single batch was combined and stored in polypropylene bottles in a refrigerator.

Example 9

Cell Rupture and Extraction of Oils from Wet Biomass of *Cupriavidus necator*

Figure 13:
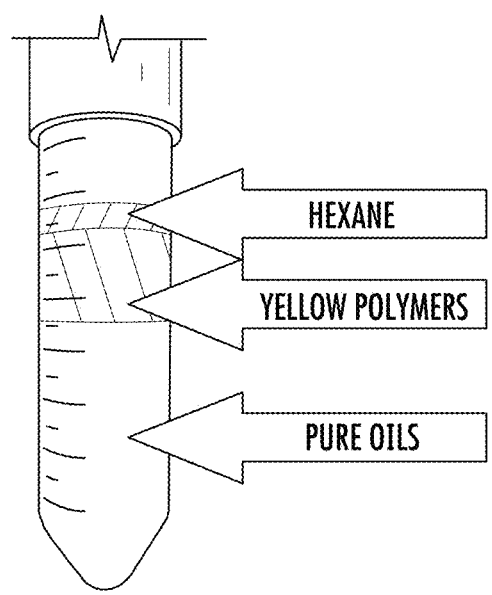
FIG. 13 shows a test tube containing a crude hexane extract from *C. necator*, which comprises an oil and polymers.
Figure 14:
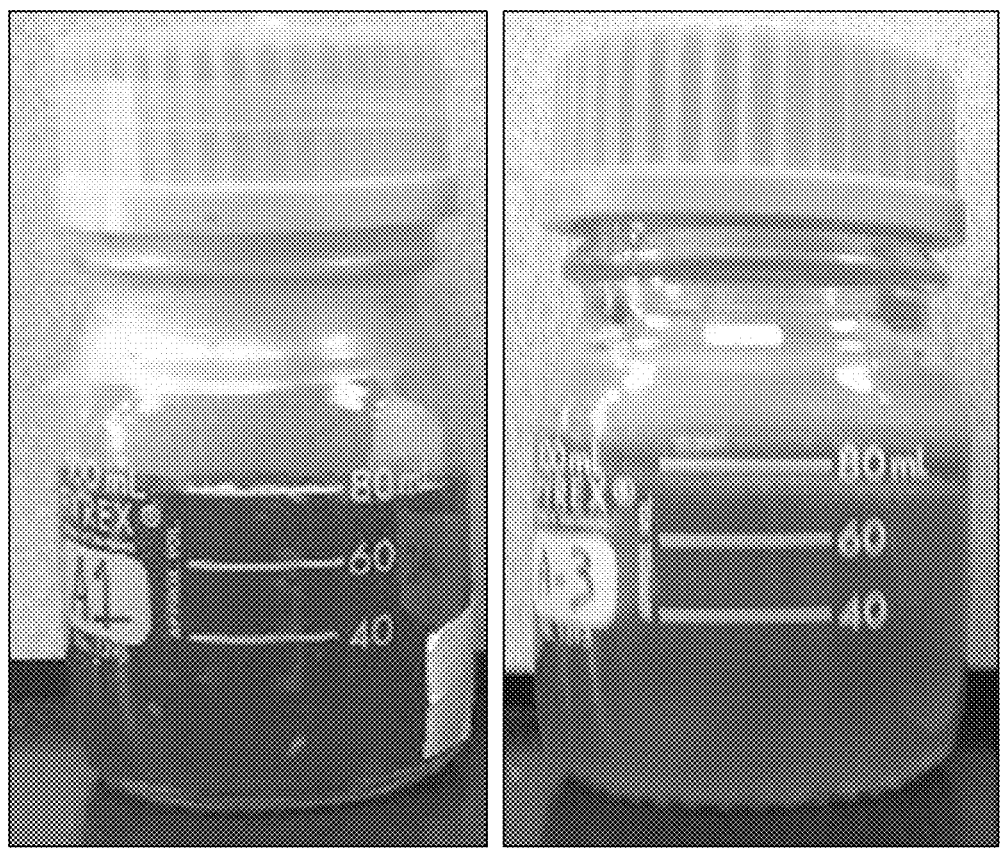
FIG. 14 shows oil samples extracted from *C. necator* grown on $CO_2$ as sole carbon source and $H_2$ as sole source of hydrogen and electrons.

Efficient oil extraction from samples of wet cell material was obtained using an isopropanol/hexane oil extraction procedure described below. Using this procedure a crude hexane extract was recovered from *C. necator* biomass grown of $CO_2$ as sole carbon source from which a microbial oil was obtained. FIG. 13 shows a test tube containing a crude hexane extract from *C. necator*, which comprises an oil and polymers. FIG. 14 shows oil samples extracted from *C. necator* grown on $CO_2$ as sole carbon source and $H_2$ as sole source of hydrogen and electrons.

To estimate the moisture content of the wet biomass, two empty vials were labeled and their weights were recorded, and 1-gram of wet biomass was allocated into each of the vials and dried for 12 hours at 60° C. using vacuum oven (Binder Safety Vacuum Oven, Model VDL 115-9030-0040). Samples were run in duplicate.

Figure 15:
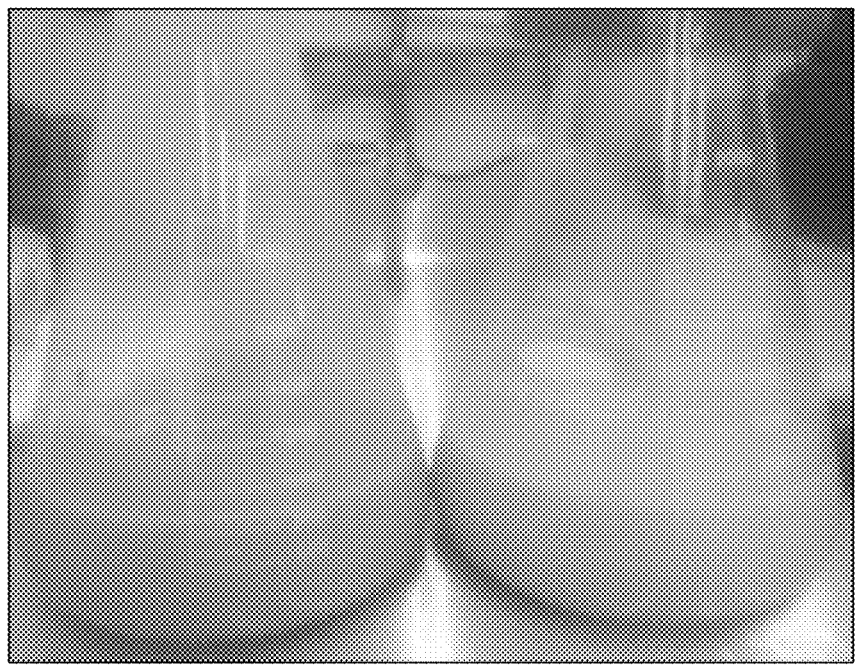
FIG. 15 shows the biomass slurry of *C. necator* before sonication (shown on the left) a brown color, and after sonication (shown on the right). Before sonication, the slurry had a brown color, and after sonication, with complete cell disruption, the color of the biomass turned from brown to cream.

To study the process parameters and operating conditions for lipids extraction using the solvents hexane and 2-propanol, 10 g (A1) and 9.4 g (A2) of wet biomass were mixed into 33.5 mL and 31.5 mL of 2-Propanol respectively. The cell suspension was then transferred into 250 mL beakers and the beakers were kept on an ice bath and were sonicated in a batch mode for 20 minutes. The wet biomass was sonicated with 2-propane for complete cell disruption, cell lysis and to recover oils from the microbial cells. A QSonica Q700 sonicator was used. A temperature probe was immersed in the beaker to record the change in temperature during sonication. Disruption of cells using sonicator or ultrasound waves is a very common method of cell lysis; ultrasound is a cyclic sound pressure wave with frequencies from 20 kHz up to several gigahertz. During the low-pressure cycle, high-intensity ultrasonic waves create small vacuum bubbles in the liquid. When the bubbles attain a volume at which they can no longer absorb energy, they collapse violently during a high-pressure cycle and the resulting shear forces to break the cell envelope. As shown in FIG. 15, after a complete cell disruption the color of the biomass turned from brown to cream. The biomass slurry before sonication is shown on the left in FIG. 15, and after sonication on the right. The initial biomass suspension was viscous but after sonication, the viscosity of the sample decreased, perhaps due to macromolecular shearing effect.

Following the cell lysis due to sonication in 2-propanol, 33.5 mL and 31.5 mL of hexane were added into A1 and A2 respectively and incubated at 60° C. for an hour. The mixture was agitated at 100 rpm. After an hour reaction time the samples were transferred into centrifuge tubes and centrifuged at 3200 g for 15 minutes using a tabletop centrifuge (Eppendorf centrifuge R). The supernatant, which is the mixture of hexane, 2-propanol, and dissolved oils, lipids and polymers was transferred into a Rotavap flask and distilled at 60° C. using rotary evaporator (Rotavap R-210/215). The hexane and 2-propanol was evaporated at 60° C. and less than 200 mbar vacuum pressures. After evaporation of hexane and 2-propanol, around 4 grams of yellow oils were recovered. The single step distillation did not separate the oils from the polymers, instead a mixture of the yellow polymers and the oils solidified inside the mix flask. Hexane was added and used to dissolve the oils from the polymers, the yellow polymers were precipitated, and a second stage distillation was performed to isolate and recover the oils.

200 g to 250 Gram Per Batch Wet Biomass Extraction

After the small-scale extraction results were confirmed, work on larger-scale extractions commenced. 4 kg of wet *C. necator* biomass was divided into 20 batches (0.2 kg per batch) for extraction, and each batch was transferred into a shake flask. To each flask was added 650 ml isopropanol. 5 mL of 2-propanol solvent was used per 1.5 gram of wet biomass. The biomass was well mixed with 2-propanol to create a uniform suspension.

After creating a uniform suspension, sonication was used to lyse the cells. A QSonica Q700 sonicator was operated in continuous mode for complete cell disruption. The flocell of the sonicator was attached to the horn and the tubes were connected to the inlet and outlet ports of the flocell. The inlet tubing on the flocell was passed through a peristaltic pump and it was immersed in the flask containing the biomass suspension, while the outlet tubing from the flocell was placed in the same flask to allow circulation. To perform a complete cell lysis, 1 to 1.2 k of energy per gram of wet biomass was dissipated. A temperature probe was immersed in the sample beaker to record the change in temperature during sonication.

Each of the 20 portions made from the 4 kg input was sonicated in batch mode at 100% amplitude for 30 minutes with 30 seconds intervals between each 1 minute sonication burst.

After sonication with 2-propanol, 5 mL of hexane per gram of wet biomass was added, then the samples were incubated using a Kuhner Shaker X at 60° C. for an hour. 650 ml of hexane was added to each batch, which was then incubated for 60 minutes at 60° C.

The samples were transferred into centrifuge tubes and were centrifuged using an Eppendorf centrifuge R at 3200 g for 15 minutes. Each batch of the biomass was distributed into 4×400 mL Eppendorf centrifuge R tubes. The centrifuge rotational speed was set at 4000 rpm, which is equivalent to 3200 g for the 18 cm rotor radius.

After separating the cell pellet, the organic extracts i.e. supernatant were transferred to a rotary evaporator (Rotavap) mixing flask. The Rotavap was used to separate the oils and polymers from hexane and 2-propanol. The hexane and 2-propanol were evaporated at 60° C. and 200-100 mbar, and the oil dried of solvent. The hexane and 2-propanol was heated by means of a heating bath at 60° C. The mixing flask of the Rotavap generates an effective heat transfer for fast evaporation and prevents local overheating while providing for a smooth mixing of the organic extract. The evaporating flask was rotated evenly and the vapor duct transported the vapor form of hexane and 2-propanol into the condenser. The receiving flask collected the condensed hexane and 2-propanol. The boiling temperature of hexane and 2-propanol are 69 and 82° C. at 1013 mbar respectively. However, hexane and 2-propanol can be distilled at 120 and 360 mbar vacuum at 40° C. respectively. It is observed that the evaporating performance depends on the distillation pressure, the heating bath temperature and rotation speed and the size of the evaporation flask.

For the larger-scale extraction, optimal distillation conditions were reached at 100-mbar vacuum pressure and 60° C. water heating bath; however after evaporating hexane and 2-propanol the yellow polymers/oils mixture was left inside the mixing flask. To separate the oils from the yellow polymers, hexane was reapplied and the polymers were then separated by centrifuge.

The polymer/oil/hexane mixture was reheated to 60° C. for 10 minutes, transferred to centrifuge tube and spun at 3200 rpm for 5 minutes. After reheating and centrifugation, oil separated and was isolated and analyzed. The oil extract was found to contain mostly saturated and mono-unsaturated C16 and C18 fatty acids including Palmitic acid—a primary constituent of palm oil. From 4 kg of wet $C.$ $necator$ biomass, which corresponded to around 1 kg of dry biomass, 80 grams of crude hexane extract (i.e. hexane soluble oils) was recovered.

In total about 230 ml of oil was extracted from various samples of $Cupriavidus$ $necator$ produced from $H_2$ and $CO_2$ as sole source of hydrogen, electrons, and carbons, according to the methods described in this section. This corresponds to around 210 grams of oil. Of this total, about 160 ml (140 grams) of the oil was extracted from samples generated by the 20-liter batch runs described in this section, and the remainder, was from other continuous and batch runs on $H_2/CO_2$ substrates.

Analysis of Crude Oil Extract

Figure 16:
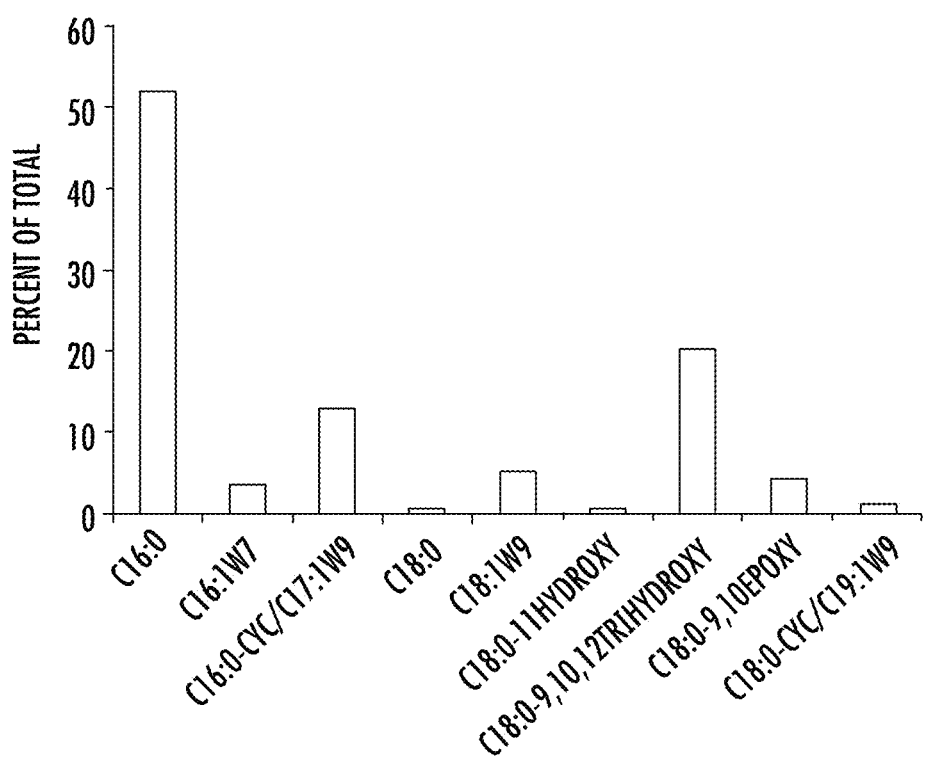
FIG. 16 shows the profile of carbon chain lengths for fatty acids that were present in the oils extracted from *Cupriavidus necator*.
Figure 17:
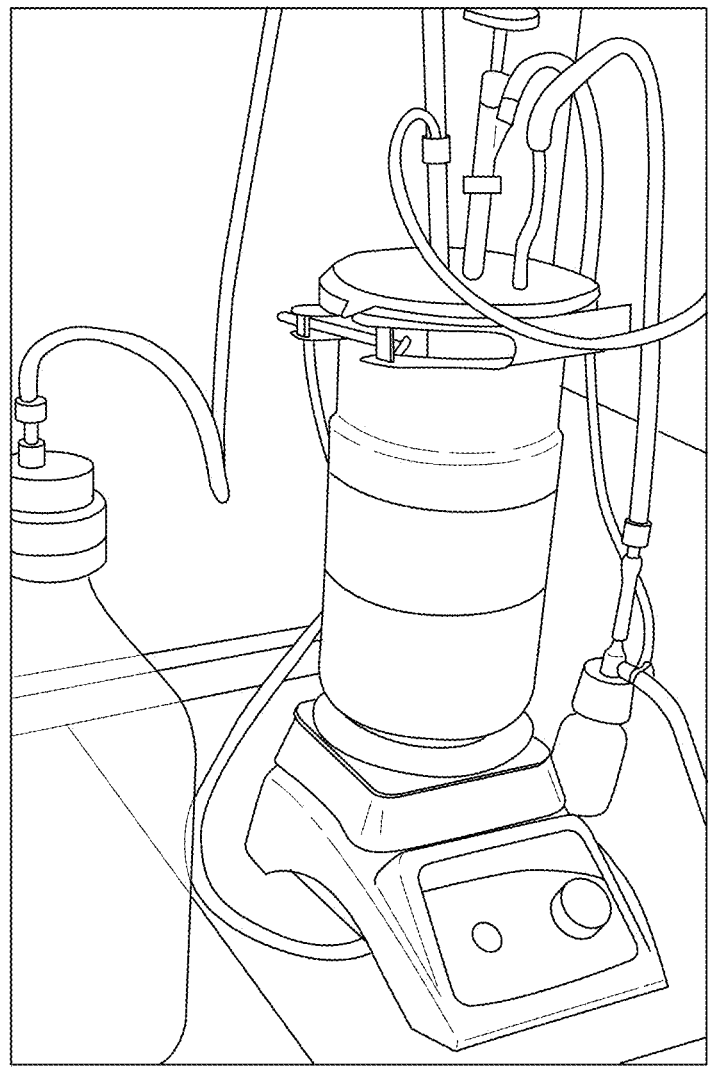
FIG. 17 shows *Hydrogenovibrio marinus* strain DSM 11271 growing in a bioreactor on a mixture of $H_2$, $CO_2$, and $O_2$ gases.

Oil produced from $CO_2$ and extracted from $C.$ $necator$ was loaded onto a silicic acid column and separated into fractions of neutral lipids (NL), polar lipids (PL) and free fatty acids (FFA). Lipids in each fractions were analyzed for acyl chain distribution by first converting to methyl ester and then analyzing by gas chromatography. The molecular weights of individual peaks were confirmed by GC/MS. The methyl ester weight percentage (wt. %) for the fatty acyl carbon-chain distribution was calculated from peak area counts, utilizing relative response factors established from analytical standards. FIG. 16 shows the profile of chain lengths for fatty acids that present in the oils extracted from $Cupriavidus$ $necator$. A major constituent of the oils is C16:0, which is Palmitic acid. Palmitic acid is also the major constituent of palm oil.

The residual biomass left after oil extraction was found to be high in PHB and protein.

Example 10

Production of Amino Acids from Syngas Feedstock, or Components Thereof $Cupriavidus$ $necator$ strains DSM 531 and DSM541 were cultured using a $H_2/CO_2/O_2$ gas mixture and mineral salt fermentation medium. The culture was grown for 96 hrs in 20 ml MSM medium (1 L Medium A: 9 g $Na_2HPO_4 \cdot 12H_2O$, 1.5 g $H_2PO_4$, 1.0 g $NH_4Cl$ and 0.2 g $MgSO_4 \cdot 7H_2O$ per 1 L; 10 ml Medium B: 50 mg Ferric ammonium citrate and 100 mg $CaCl_2$ per 100 ml; 10 ml Medium C: 5 g $NaHCO_3$ per 100 ml; and 1 ml Trace Mineral Solution: 100 mg $ZnSO_4 \cdot 7H_2O$, 30 mg $MnCl_2 \cdot 4H_2O$, 300 mg $H_3BO_3$, 200 mg $CoCl_2 \cdot 6H_2O$, 10 mg $CuCl_2 \cdot 2H_2O$, 20 mg $NiCl_2 \cdot 6H_2O$ and 30 mg $Na_2MoO_4 \cdot 2H_2O$ per 1 L) in a serum bottle supplemented with 66.7% $H_2$, 9.5% $CO_2$, 5% $O_2$ and 18.8% $N_2$ at 30° C. and 200 rpm.

For lysine detection in the growth media, 1 ml of the cells (OD=0.1) were separated by centrifugation (10,000 rpm, 5 min at room temperature) and the supernatant (200 microliters) was further filtrated (0.22 micron). Samples of the supernatants were collected and analyzed for secretion of amino-containing compounds, such as amino acids including lysine, tyrosine, and phenylalanine, as shown in Table 2. Lysine is a six carbon molecule, and tyrosine and phenylalanine are nine carbon molecules. It was observed that $C.$ $necator$ strain DSM541 secreted higher concentrations of lysine, tyrosine, and phenylalanine into the medium compared to $C.$ $necator$ strain DSM531. The analyses were performed on 200 μl of sterile filtered fermentation medium. Compounds were isolated and derivatized using a clean-up and derivatization kit (e.g., EZ-FaaST (Phenomenex) followed by liquid chromatography-mass spectrometry to separate and identify compounds that had been secreted by the bacterial strains into the medium (Table 2). The levels of lysine found in the media from DSM 541 were 125 fold higher than DSM 531.

TABLE 2

Secreted amino-containing compounds from $C.$ $necator$

| | Compound | Blank | DSMZ 531: C. necator umol/L | DSMZ 541: C. necator umol/L | fold difference |
|---|---|---|---|---|---|
| Glu | Glutamic acid | 0.1952 | 11.556 | 40.614 | 3.5 |
| Sar | Sarcosine | 1.7232 | 2.5708 | 36.4692 | 14.2 |
| Ser | Serine | 1.7688 | 7.9428 | 35.8164 | 4.5 |
| Gly | Glycine | 9.4757 | 10.3272 | 35.0351 | 3.4 |
| Ala | Alanine | 0.6504 | 5.996 | 32.3436 | 5.4 |
| Thr | Threonine | 0.216 | 5.4152 | 22.9456 | 4.2 |
| Val | Valine | 0.0984 | 4.182 | 21.5904 | 5.2 |
| Ile | Isoleucine | 0.0272 | 2.1476 | 14.0068 | 6.5 |
| Orn | Ornithine | 0.9324 | 10.4876 | 13.056 | 1.2 |
| His | Histidine | 0.99 | 2.3816 | 12.0852 | 5.1 |
| Arg | Arginine | 0.2988 | 0.4112 | 9.3428 | 22.7 |

TABLE 2-continued

Secreted amino-containing compounds from C. necator

| | Compound | Blank | DSMZ 531: C. necator umol/L | DSMZ 541: C. necator umol/L | fold difference |
|---|---|---|---|---|---|
| Phe | Phenylalanine | 0.1 | 3.4216 | 8.6652 | 2.5 |
| Lys | Lysine | 0.1012 | 0.063 | 7.9088 | 125.5 |
| Tyr | Tyrosine | 0.386 | 2.9448 | 7.3972 | 2.5 |
| Cit | Citosine | 0.3332 | 0.6572 | 6.8248 | 10.4 |
| Asp | Asparatic acid | 2.1964 | 3.2776 | 4.6132 | 1.4 |
| Gln | Glutamine | 0.1412 | 1.2548 | 4.2944 | 3.4 |
| Pro | Proline | 0.0477 | 1.2567 | 4.1107 | 3.3 |
| Leu | Leucine | 0.054 | 2.5558 | 3.7205 | 1.5 |
| Trp | Tryptophan | 0.0352 | 0.9464 | 2.7072 | 2.9 |
| Met | Methionine | 0.0156 | 1.3944 | 1.614 | 1.2 |
| Tpr | Tpr | 0.034 | 0.5208 | 0.8052 | 1.5 |
| B-Ala | B-Alanine | 0 | 2.0904 | 0.6688 | 0.3 |
| SAM | S-Adenosylmethionine | 0 | 0 | 0.5604 | |
| SAH | S-Adenosylhomocysteine | 1.194 | 2.3232 | 0.2812 | 0.1 |
| MetSo | Methionine Sulfoxide | 0.0128 | 0.3696 | 0.2528 | 0.7 |
| Hcy-PCA | Hcy-PCA | 0.024 | 0.1944 | 0.2344 | 1.2 |
| a-AAA | a-AAA | 0.0096 | 0.2008 | 0.1492 | 0.7 |
| APA | APA | 0 | 0.0248 | 0.134 | 5.4 |
| Put | Putracine | 0.1912 | 15.0568 | 0.128 | 0.0 |
| Cys-PCA | Cys-PCA | 0.0392 | 0.7148 | 0.1272 | 0.2 |
| GSH-PCA | GSH-PCA | 0.0056 | 0.0052 | 0.0468 | 9.0 |
| Spd | Spd | 0.0652 | 0.0728 | 0.0444 | 0.6 |
| 3-His | 3-His | 0.0264 | 0.0384 | 0.0276 | 0.7 |
| Cy2 | Cy2 | 0.0364 | 0.0628 | 0.0128 | 0.2 |
| Cth | Cth | 0.0072 | 0.0072 | 0.0124 | 1.7 |
| CysGly-PCA | CysGly-PCA | 0.002 | 0.01 | 0.0112 | 1.1 |
| Erg | Erg | 0.0076 | 0.0512 | 0.0084 | 0.2 |
| Hcy2 | Hcy2 | 0.0116 | 0.008 | 0.0048 | 0.6 |

Example 11

*Hydrogenovibrio marinus* strain DSM 11271 was grown to over eight grams per liter dry cell density on a mixture of $H_2$, $CO_2$, and $O_2$ gases as the sole source of energy and carbon for growth. The following protocol was followed for experiments performed using a mixture of gases including $H_2$, $CO_2$, and $O_2$ in a stirred-tank bioreactor.

Apparatus: Culture was grown in batch, using custom-manufactured 500 mL glass fermenter with PEEK headplate; a sparge tube having one porous glass frit, connected to tubing for gas delivery with a 0.2 μm filter; a septum port for amendment delivery; a dip-tube to bottom with aseptic sampling assembly, a condenser connected via tubing to an overflow vessel with a 0.2 μm filter on the gas outlet; a port for base delivery and tubing for base-delivery with a luer fitting to a sterile syringe; a grounding probe; a port for antifoam delivery; a pH/temperature probe; an oxidation/reduction probe (ORP). Temperature was controlled to 37° C., and pH to 6.5, using a commercial controller (Electrolab, Fermac 360, United Kingdom). The target temperature was maintained by a heating pad on the bottom of the reactor, and an integral glass jacket for cooling water. The pH was maintained at 6.5 using 6N $NH_4OH$. The reactor sat on a stir-plate (VWR 12365-344) and a magnetic stir bar (cross shape, VWR 'spinplus' #58947-828) was used for mixing. The stirplate was set to 300-400 RPM. The gas flow rate into the bioreactor was 1 VVM. Gas supply was from compressed $H_2$, compressed $CO_2$ and house air, each regulated to 20 psi. $H_2$ and $CO_2$ were delivered to a flow proportioner (Matheson G2-4D151-E401/E401, 20 psi), which set the relative fraction of the gases. Air was delivered to a variable area flow meter (Key Instruments 1G03_R5). The $H_2/CO_2$ gas mix from the flow proportioner was tee'd into the air, and then delivered to the fermenter through a variable area flow meter. A pressure gauge was used to monitor the gas delivery pressure to the fermenter. Inlet gas flowed through a 0.2 μm filter (Pall, p/n 4251), and then was dispersed into the fermenter broth via one porous pyrex frit (40-60 m, Sigma-Aldrich CLS3953312-C) and vented from the reactor via a condenser (jacketed and cooled) to a 2 L foam-overflow bottle, then through another 0.2 μm filter (Pall, p/n 4251) and finally to an exhaust system. $CO_2$ flow was set to the minimum c.l.=5 (c.l.=centerline of float), and the other gases were set to achieve the targeted gas composition, calculating according to the flow meter tables, measuring composition by GC and adjusting and re-measuring. c.l. $H_2$=25, c.l. air=45 was used to provide a gas mix having respective proportions of $CO_2/O_2/H_2$ of 11/6.3/59. Ongoing monitoring of $O_2$ in influent and effluent lines was done using a Foxy probe. Occasional gas samples were taken for GC analysis (in 1 L foil bags, skcinc.com p/n 262-01).

Medium: One liter of the basal medium contained 2.0 g $K_2HPO_4$, 1.0 g $KH_2PO_4$, 5.0 g $(NH_4)_2SO_4$, 29.3 g NaCl, 0.2 g $MgSO_4 \cdot 7H_2O$, 10.0 mg $CaCl_2$, 10.0 mg $FeSO_4 \cdot 7H_2O$, 0.6 mg $NiSO_4 \cdot 7H_2O$, and 2.0 ml of trace element solution. The trace element solution was taken from Thermophilic Bacteria, CRC Press, Boca Raton, FL, Jacob K. Kristjansson, ed., 1992, p. 87, Table 4.

Autotrophic inoculum: A 10% inoculation gas-grown inoculum was prepared in two 500 ml bottles with stoppers containing 50 mL of liquid media. A volume of 61.5 mL inoculum, OD600 0.75, was injected into bioreactor via a dip-tube to below the liquid level to prevent dispersion in headspace. The line was flushed with filtered air after inoculation to remove trapped inoculum in the dip-tube.

Fermenter Operation: Base addition—pH was controlled with 6N NH$_4$OH; Nutrient amendment—In addition to nitrogen nutrient provided by base addition of NH$_4$OH, 0.2 grams FeSO$_4$·7H$_2$O were added when the broth OD=3, and 2 grams MgSO$_4$·7H$_2$O when the broth OD=10. The influent O$_2$ was measured to be around 5%, and effluent O$_2$ ranged from 3-4%. Samples were withdrawn from a tube extending to the bottom of the reactor using an aseptic sampling system with 25 mL bottles. The DNA sequencing results confirmed *H. marinus* and no contamination was observed to grow on agar plates that were streaked daily throughout the run.

Table 3 shows the cell dry weight (CDW) density measured at various time points during the run. The CDW density reached over eight grams/liter during day 5. The content of chloroform/methanol soluble lipid, and hexane soluble lipid, respectively, as a percentage of the biomass sampled at various time points, is also given in Table 3. The lipids were analyzed by GC/MS using the methods described above and were found to contain fatty acids ranging from 14 to 20 carbons in length.

TABLE 3

| Sample ID | Days | Vol (mL) | CDW (g/L) | OD | n | c/m extractable (%) Average | S.D. | Hexane extractable (%) Average | S.D. |
|---|---|---|---|---|---|---|---|---|---|
| T3 | 2.78 | 25 | 4.556 | 7.068 | 2 | 19.34 | 11.12 | 6.88 | 0.72 |
| T4 | 3.79 | 25 | 6.776 | 11.824 | 3 | 18.42 | 2.83 | 8.12 | 0.43 |
| T5 | 4.79 | 25 | 7.492 | 14.18 | 3 | 20.59 | 6.31 | 8.99 | 2.39 |
| T6 | 5.79 | 25 | 8.296 | 13 | 3 | 24.13 | 6/07 | 8.26 | 1.53 |

Example 12

*Rhodopseudomonas capsulata* strain DSM 1710 was grown to an OD of 4.5 on a mixture of H$_2$, CO$_2$, and O$_2$ gases as the sole source of energy and carbon for growth. The following protocol was followed for experiments performed using a mixture of gases including H$_2$, CO$_2$, and O$_2$ in a one-liter sealed bottle fed a continuous flow of gases.

Figure 18:
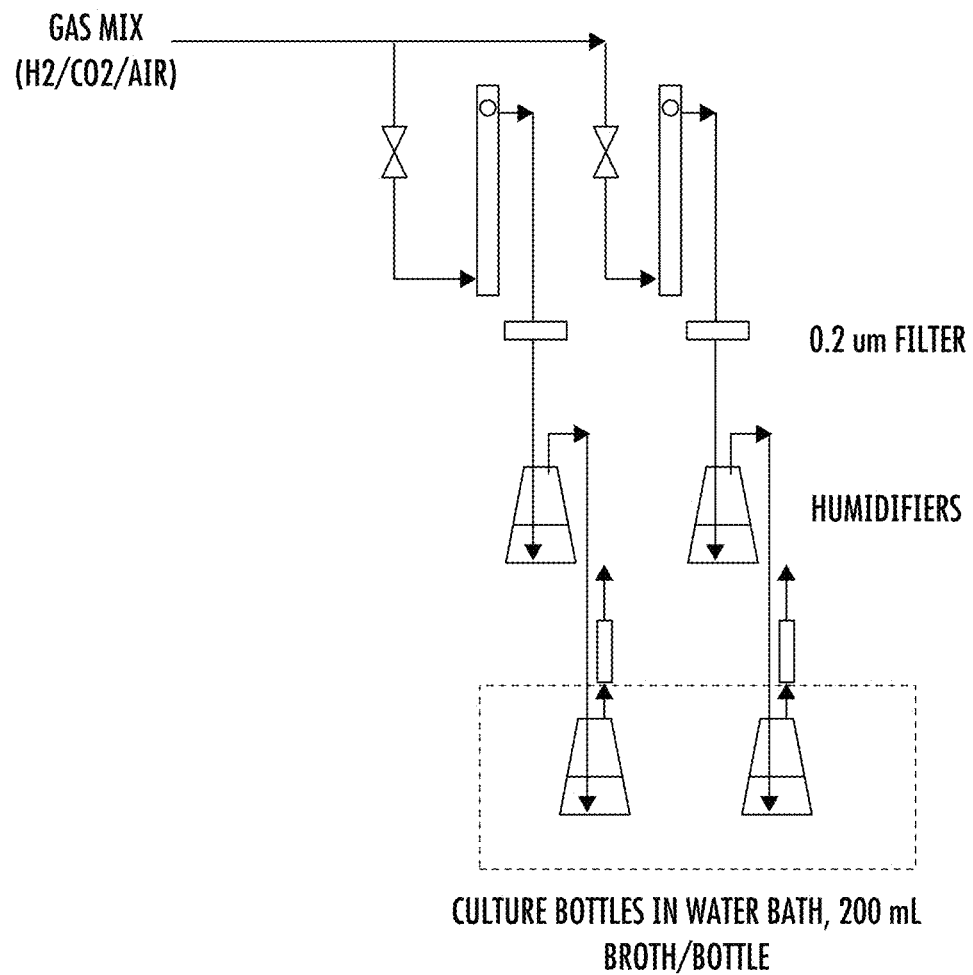
FIG. 18 shows a system of gas delivery and culture bottles used to grow *Rhodopseudomonas capsulata* strain DSM 1710, diagrammed schematically.

Apparatus: Culture was grown in batch, using custom-manufactured system comprising one-liter high pressure liquid chromatography (HPLC) solvent delivery bottles, which were repurposed for use as culture bottles. These one-liter culture bottles were continuously fed gases from a system of gas tanks; gas mixers; filters (0.2 micron); flowmeters; and humidifiers. This system of gas delivery and culture bottles is illustrated schematically in FIG. 18. The gases were distributed and mixed into solution using a porous glass frit. The culture bottles contained 200 mL of liquid media and were wrapped in aluminum foil to prevent light from penetrating media. Temperature was controlled by immersing the culture bottles in a water bath. pH was not controlled beyond the including of chemical buffers into the media. The gas was outlet from the culture bottles through a 0.2 micron filter and the entire system was installed inside of a fume hood. Gas supply was from a compressed H$_2$ and CO$_2$ gas mixture, and a separate tank of compressed O$_2$. The target gas mix for the experiment was 10% O$_2$, 5% CO$_2$, and 85% H$_2$. The flowmeter from the H$_2$/CO$_2$ gas tank mix was set to 25 and that from the O$_2$ tank was set to 34. This resulted in a gas mixture of 10.5% O$_2$, 5% CO$_2$, and 84.5% H$_2$ as measured by GC (Shimadzu GC-8A, TCD detector, and Alltech CTR I column), which was deemed close enough to the target mixture for conducting the experiment.

Medium: 970 ml DI water; 20 mg Na$_2$·EDTA; 12 mg FeSO$_4$·7H$_2$O; 200 mg MgSO$_4$·7H$_2$O; 75 mg CaCl$_2$·2H$_2$O; 1 g NaCl; 1 g (NH$_4$)$_2$SO$_4$; 1 mg thiamine HCl; 15·g biotin; 1 ml trace element solution. Trace element solution: 250 mL DI water; 700 mg H$_3$BO$_3$; 398 mg MnSO$_4$·H$_2$O; 188 mg Na$_2$MoO$_4$·2H$_2$O; 60 mg ZnSO$_4$·7H$_2$O; 10 mg Cu(NO$_3$)$_2$. pH was adjusted to 7.2 before autoclaving. After autoclaving added 30 ml sterile solution with 1.2 g KH$_2$PO$_4$ and 1.8 g K$_2$HPO$_4$. pH readjusted back to pH=7.2.

Inoculum: A 10% inoculum provided from *R. capsulata* culture grown photoheterotrophically in light with agitation of 250 rpm. The RCVB media given in Wall, J. D., Johansson, B. C., Gest, H. (1977) A pleiotropic mutant of *Rhodopseudomonas capsulata* defective in nitrogen metabolism. Arch. Microbiol. 115:259-263 was used for photoheterotrophic growth of the inoculum which had a dark green color. This photoheterotrophically grown inoculum was in turn started from a glycerol stock of the strain stored at −80° C.

Figure 19:
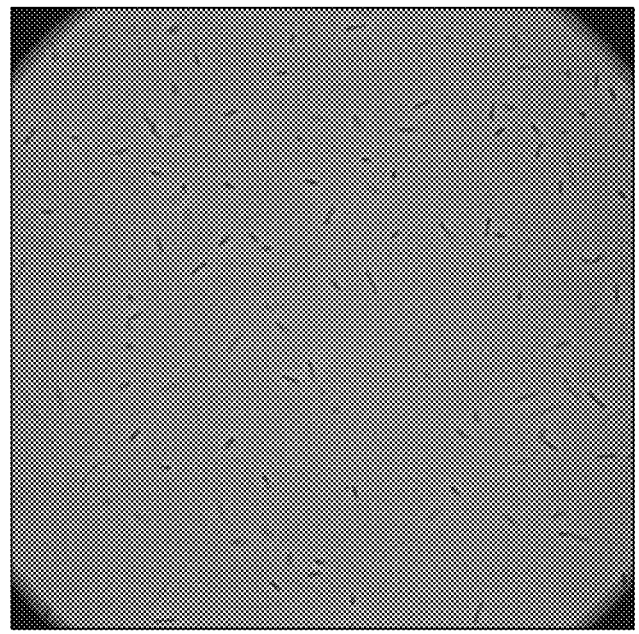
FIG. 19 shows a micrograph of *R. capsulata*.
Figure 20:
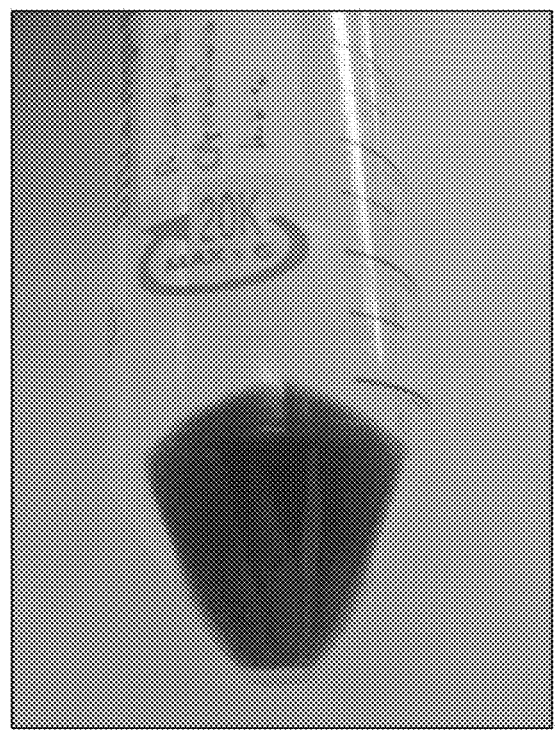
FIG. 20 shows a pellet of *R. capsulata* biomass recovered after centrifugation.

Operation: The 10% inoculum resulted in a starting OD of 0.15. After eight days of growth on gas the OD reached 4.5. OD was measured using a Beckman Coulter DU720 UV/Vis spectrophotometer at 650 nm. The color of the chemoautotrophically grown culture was dark red. Wet mounts of the culture were observed using phase contrast optics with an Axioskop research microscope (Zeiss, Germany). Micrographs were generated with a MacroFIRE device (Optronics; Galeta, CA) using the PictureFrame (Optronics; Galeta, CA) software for imaging and data storage. A micrograph of the *R. capsulata* is shown in FIG. 19. Following chemoautotrophic growth the culture was centrifuged at 10,000×g for 15 minutes and 4° C. The supernatant was then poured off and the biomass pellets were stored temporarily at −20° C. and then freeze dried. A picture of a pellet of *R. capsulata* biomass recovered after centrifugation is shown in FIG. 20. A total of 2.59 grams of wet biomass were recovered in this fashion from a single one-liter bottle of *R. capsulata* grown on H$_2$ and CO$_2$ as the sole source of hydrogen, electrons, and carbon for biosynthesis. The lipids were extracted and analyzed by GC/MS using the methods described above, and were found to contain fatty acids that were primarily 16 or 18 carbons in length.

Example 13

*Hydrogenobacter thermophilus* DSM 6534 was grown in a one-liter gas tight bottle on a mixture of H$_2$ and CO$_2$ and O$_2$ gases as sole sources of energy and carbon for growth. A live culture of *H. thermophilus* DSM 6534 in a serum bottle under a gas headspace was received from Deutsche Sammlung von Mikroorganismen und Zellkulturen (DSMZ). This live culture was used to provide a 10% inoculum to a 160 ml serum bottle containing the MSM media given in "Thermophilic bacteria," Jakob Kristjansson, Chapter 5, Section III, CRC Press, 1992, pp. 86-88 under an H$_2$:CO$_2$:O$_2$ atmosphere of 8:1:1. The initial OD at 600 nm following inoculation was 0.03. The temperature of the serum bottle was kept at 70° C. by immersing the serum bottle in a heated water bath. No agitation was applied. The media was observed to become turbid, and after 65 hours the OD was measured to be 0.354—a greater than ten-fold increase. This serum bottle was then subcultured as a 10% inoculum into a one-liter gas-tight bottle containing 120 mL of MSM media and 8:1:1 atmosphere of $H_2:CO_2:O_2$. The culture bottle was kept at 70° C. using a water bath and was not agitated. Over the course of 64 hours the gas headspace was refreshed once and the OD increased to 0.25. Over the next 24 hours the OD increased to 0.42. The headspace gases were refreshed again and two days later the OD was measured at 0.56. 1 mL of culture broth was sampled for DNA extraction and sequencing.

The 16S rRNA sequence was determined and the top BLAST hit was identified as *Hydrogenobacter thermophilus* TK-6 strain. Culture broth was then taken removed from the one-liter bottle and centrifuged at 10,000×g for 15 minutes at 4° C. The pellet of wet biomass resulting after centrifugation weighed 212 mg. A hexane extraction of the wet biomass was performed as described in the Example above. 15.2 mg of hexane soluble lipids were recovered from the wet biomass, or, 7.2% of the wet biomass weight was comprised of hexane soluble lipids. The lipids were extracted and analyzed by GC/MS using the methods described above, and were found to have a relatively high proportion of fatty acids with 20 carbon chain lengths.

Example 14

*Xanthobacter autotrophicus* strain DSM 432 was grown to 14 grams per liter dry cell density on a mixture of $H_2$, $CO_2$, and $O_2$ gases as the sole source of energy and carbon for growth. The following protocol was adhered to for an experiment performed using a mixture of gases including $H_2$, $CO_2$, and $O_2$ in a stirred-tank bioreactor.

Figure 23:
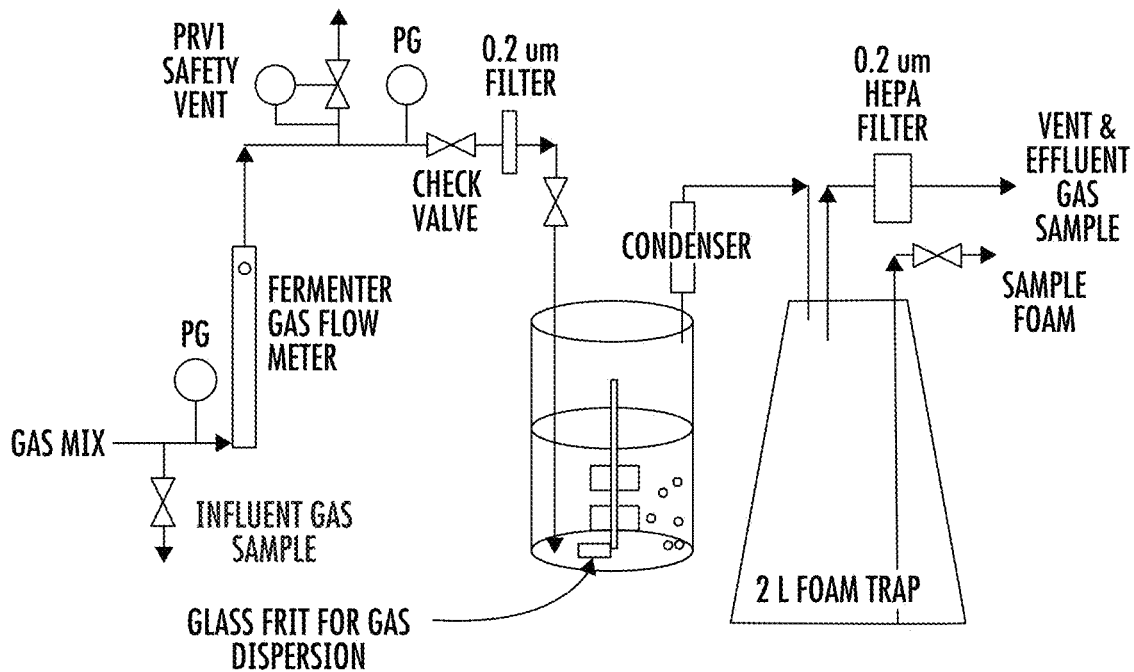
FIG. 23 shows a schematic diagram of a reactor system used to grow *Xanthobacter autotrophicus*, including pressure gauges; gas flow meters; safety and check valves; 0.2 micron filters; the bioreactor vessel, sensors, actuators, and controllers; a condenser and foam trap; and outlet vent.
Figure 24:
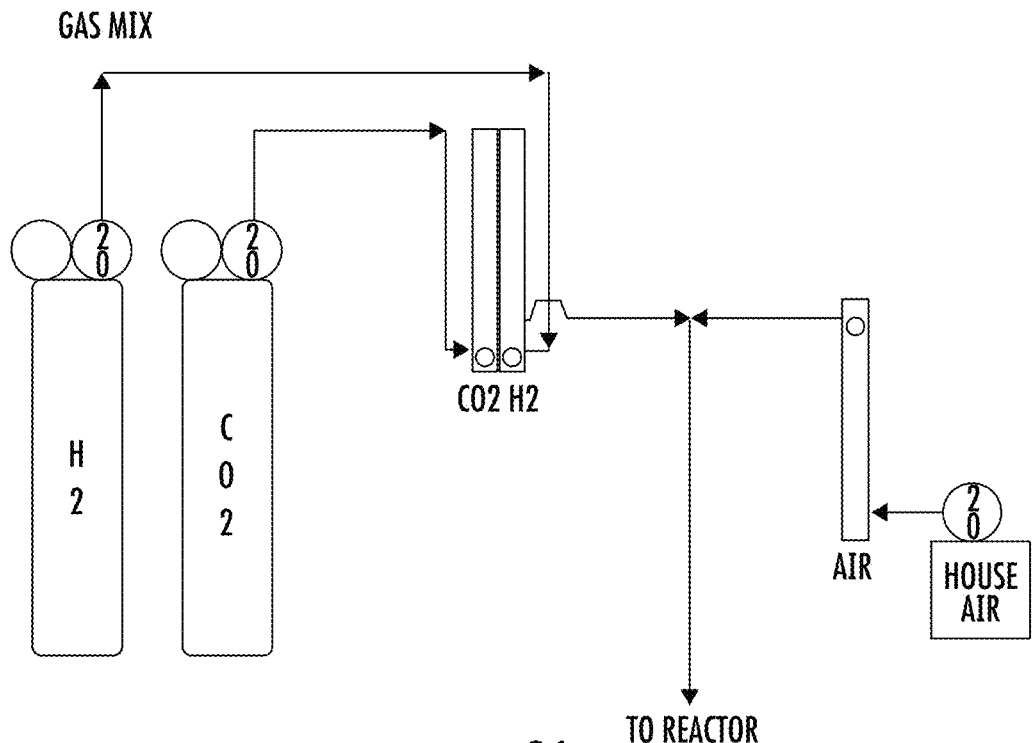
FIG. 24 shows a schematic diagram of the gas delivery system used to grow *X. autotrophicus*.

Apparatus: Culture was grown in batch, using a two-liter glass fermenter schematically illustrated in FIG. 21 with a headplate schematically illustrated in FIG. 22. Temperature and pH were controlled and monitored with pH and temperature probes and a commercial controller. pH was adjusted through automatic addition of 2N NaOH. Ports in the bioreactor were available for provision of nutrient supplements and anti-foam; inoculum delivery; base; fresh media; and aseptic sampling. Agitation was provided by a turbine and gases were sparged through a glass frit. The reactor system is illustrated schematically in FIG. 23. It comprised pressure gauges; gas flow meters; safety and check valves; 0.2 micron filters; the bioreactor vessel, sensors, actuators, and controllers; a condenser and foam trap; and outlet vent. Gas supply was from compressed $H_2$, compressed $CO_2$ and house air, each regulated to 20 psi. A schematic of the gas delivery system is shown in FIG. 24. $H_2$ and $CO_2$ were delivered to a flow proportioner (Matheson G2-4D151-E401/E401, 20 psi), which set the relative fraction of the gases. The settings used in the flow proportioner were c.l. $H_2=35$; c.l $CO_{2=10}$; and c.l air=55. This resulted in a gas mix being delivered to the bioreactor of 64% $H_2$, 11% $CO_2$, 5.4% $O_2$ as measured by GC (Shimadzu GC-8A, TCD detector, and Alltech CTR I column).

Medium: The MSM medium used for this experiment is described in Thermophilic Bacteria, CRC Press, Boca Raton, FL, Jacob K. Kristjansson, ed., 1992, p. 87, Table 4.

Inoculum: *Xanthobacter autotrophicus* strain DSM 432 inoculum was started from a single glycerol stock vial stored at −80° C. which was transferred into 200 mL of MSM in a one-liter gas-tight bottle. Gas pressure of the $H_2/CO_2/O_2$ headspace was 10 psig. The culture bottle was agitated at 150 rpm at 30° C.

Fermenter Operation: Prior to inoculation, 1.3 liters of MSM was transferred into the bioreactor vessel. The pH was adjusted to 6.8 using NaOH. The temperature was set at 30° C. and the agitation was set at 500 RPM. Samples were taken twice per day for OD and lipid analysis through an aseptic sampling assembly. All OD measurements were performed with a Beckman Coulter DU720 UV/Vis spectrophotometer. One time per day samples were examined under the microscope to check cell morphology. All culture broth samples were centrifuged at 12,000×g. 1 mL of supernatant was stored for $NH^{4+}$ analysis at −20° C. Wet biomass pellets were stored temporarily at −80° C. and then freeze dried.

Figure 25:
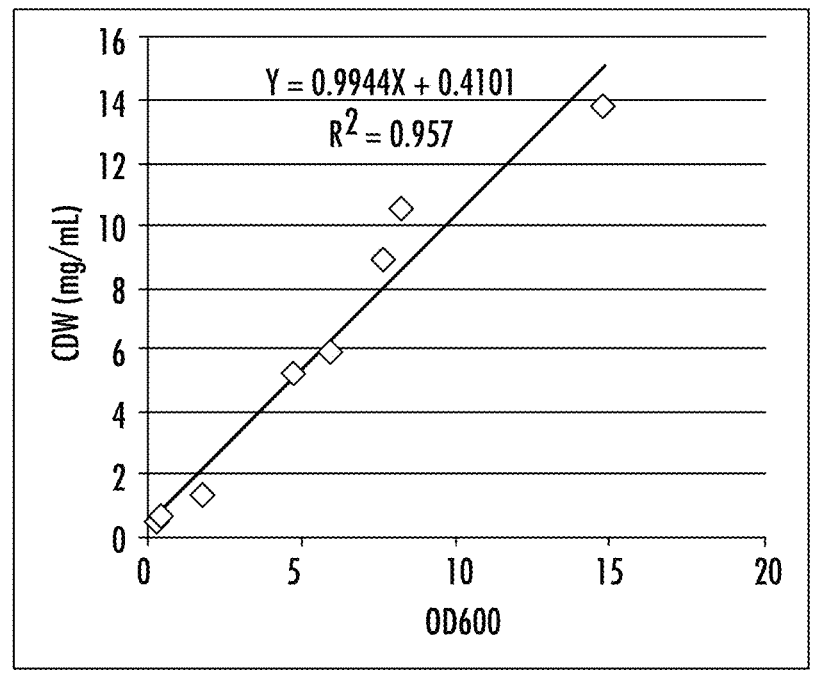
FIG. 25 shows correlation between OD600 and cell dry weight (CDW) for *X. autotrophicus*.
Figure 26:
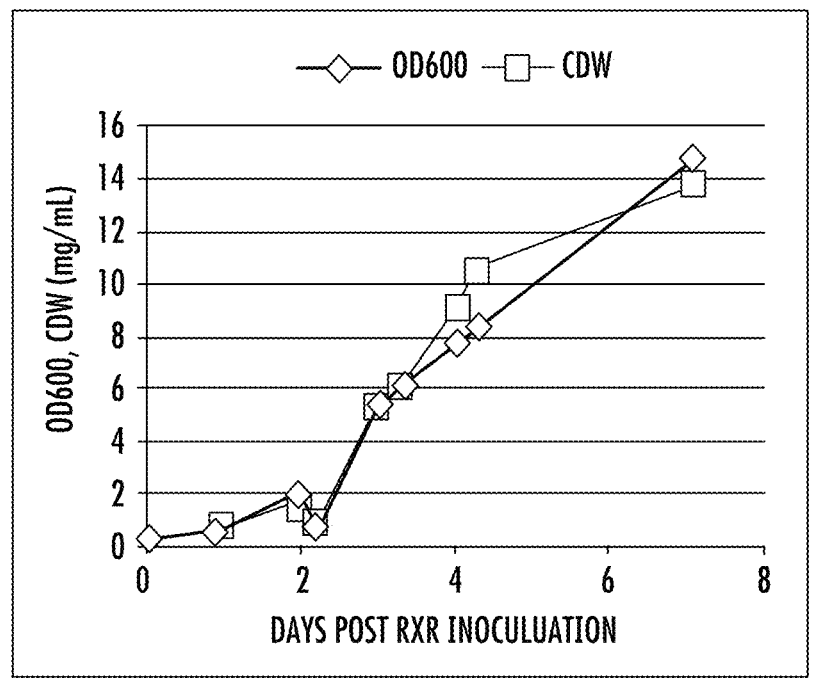
FIG. 26 shows the growth curve for the knallgas microorganism *X. autotrophicus* grown on $H_2/CO_2/O_2$.
Figure 27:
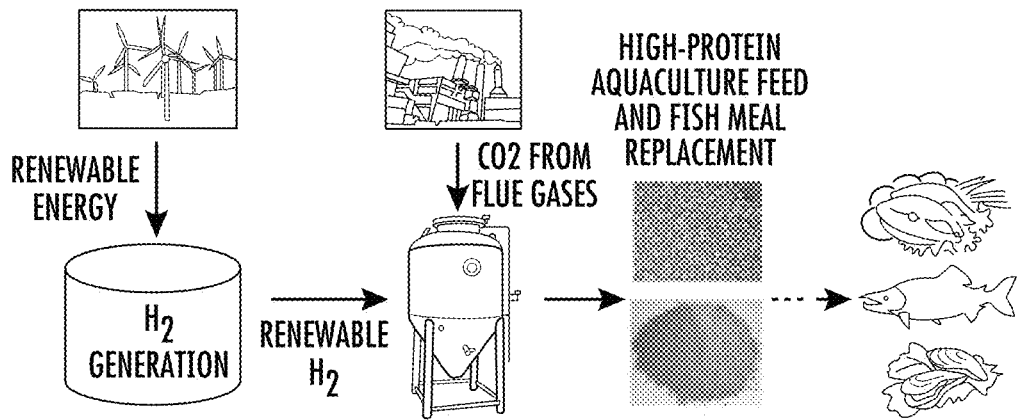
FIG. 27 shows $CO_2$+renewable $H_2$ for production of aquaculture feed.
Figure 28:
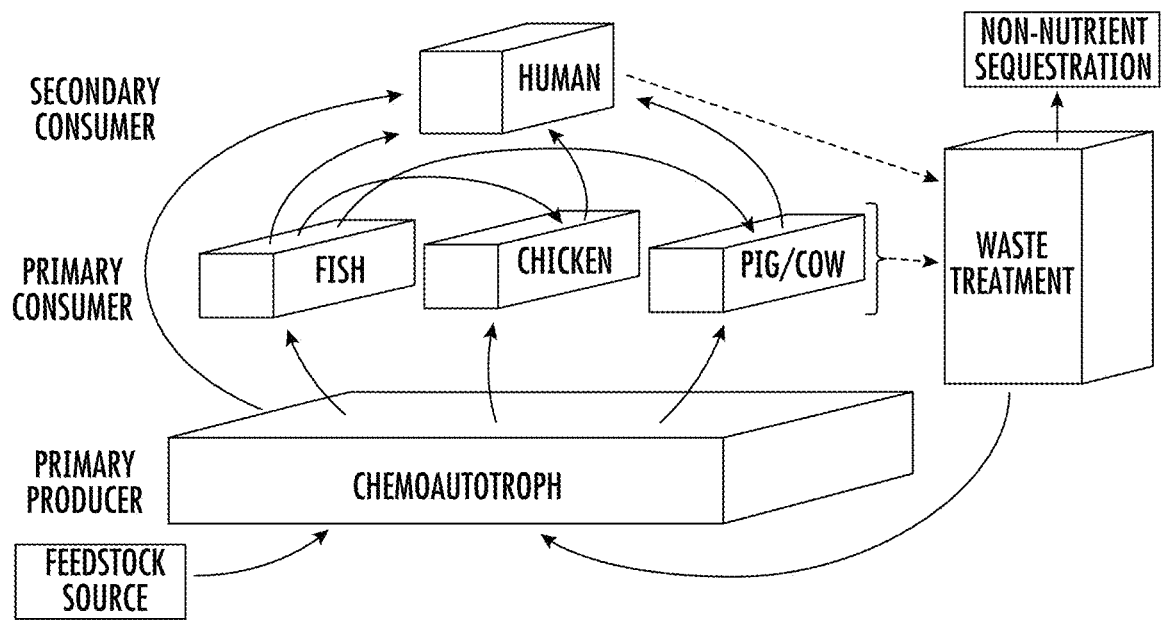
FIG. 28 shows a composite multi-stage life-support system or ecological system with a chemoautotrophic primary producer.

The correlation between $OD_{600}$ and CDW (mg/ml) is shown in FIG. 25. The linear fit to this correlation is $CDW=0.9944*(OD_{600})+0.4101$ with an $R2=0.957$. FIG. 26 shows the growth curve for the knallgas microorganism *Xanthobacter autotrophicus* grown on $H_2/CO_2/O_2$ gas substrate according to this protocol. The final OD measured at 600 nm was 14.8 and the final CDW was 13.8 grams/liter from growth on $H_2/CO_2/O_2$ gas substrate. After a brief period of logarithmic growth at the onset of the run, the biomass accumulated at a roughly linear rate until the termination of the run on day six. The lipids were extracted and analyzed by GC/MS using the methods described above, and were found to have a relatively high proportion of fatty acids that are 18 carbons in length.

Example 15

The following calculations, which consider only geometric factors and the intrinsically higher productivity of knallgas strains grown on $CO_2$, clearly illustrate the advantages of applying knallgas microbes as described herein over those bioprocesses based on photosynthetic organisms. First, for comparison, the average biomass productivity per unit area, or areal productivity, in the U.S. for algae grown in ponds on $CO_2$ is reported to be 13.2 g/m²/day [ANL, NREL, PNNL 2012. Renewable diesel from algal lipids: an integrated Baseline for cost, emissions and resource potential from a harmonized model. ANL/ESD/12-4; NREL/TP-5100-55431; PNNL-21437. Argonne Il: Argonne National Laboratory; Golden CO: National Renewable Energy Laboratory; Richland WA: Pacific Northwest National Laboratory].

The knallgas strain *Cupriavidus necator* was grown on $H_2$ and $CO_2$ in standard off-the-shelf lab-scale bioreactors to dry biomass densities above 40 g/liter over the course of 6 days. This corresponds to an average volumetric productivity of roughly 7 g/liter/day. To translate this demonstrated volumetric productivity to a predicted areal productivity at commercial scale, it should be noted that knallgas cultivation is compatible with commercially proven industrial bioreactors and equipment used throughout the fermentation industry. These bioreactors often contain working volumes having water columns from ten to forty meters in depth [Mads O. Albæk, Krist Gernaey, Morten S. Hansen, Stuart M. Stocks. Evaluation of the efficiency of alternative enzyme production technologies (2012); Richard Westlake. Large-scale Continuous Production of Single Cell Protein. *Chemie Ingenieur Technik*, 58:934-937 (January 1986]. In contrast, because of light requirements, and the issue of light blockage, where surface organisms block light from interior organisms, algal ponds are typically limited to only about ten centimeters in depth. An average chemoautotrophic volumetric productivity of 7 g/liter/day scaled up to 10 to 40 meter water columns, would yield areal productivities of 70,000 to 280,000 g/m²/day, for the 10 m and 40 m deep cases respectively. This represents a 5,000 to 20,000-fold advantage over microalgae productivity on $CO_2$ per unit area. It should be noted that microalgae itself can have a two to 20-fold areal productivity advantage against higher-plant agricultural crops such as soy or corn. Therefore, knallgas microbes applied in the present invention could have at least a 10,000-fold advantage in areal biomass productivity and $CO_2$ capture over traditional agricultural crops and systems.

It has been found that straightforward bioreactor design changes can increase volumetric productivities for *C. necator* to 1 g/liter/hr (i.e., 24 g/liter/day) on $H_2$ and $CO_2$ substrates. These simple mechanical enhancements increase the mass transfer coefficient for gas delivery into solution ($K_La$) in stirred-tank bioreactors, resulting in this significant gain in productivity. Moreover, scaling up reactor volumes, specifically vertical dimensions, will enhance mass transfer of low solubility gases such as $H_2$ and $O_2$, through increased hydrostatic pressures at increased water column depth. Using a combination of reactor design improvements to increase $K_La$, and increased hydrostatic pressure with scale up, a biomass productivity of at least 2 g/liter/hr (i.e., 48 g/liter/day) is conservatively achievable.

These calculations from empirical data sets illustrate the disruptive potential of knallgas systems to intensify biological $CO_2$ capture into practical, small area units, for profitable biomass and protein production.

Example 16

An integrated system could have the stoichiometries provided in FIG. 30.

The biosynthesis reaction formula represents a reaction derived from empirical data for the knallgas microbe *Cupriavidus necator* with the utilization of 16.4 hydrogen molecules and 3.2 oxygen molecules to reduce 4.5 molecules of $CO_2$ to cell material. The nitrogen source is assumed to be urea. Human oxidation of food with oxygen to produce $CO_2$ is shown in the formula for Human Digestion, Respiration, and Excretion, with the nitrogenous waste assumed to be urea. An input of energy to split water and produce the oxygen and hydrogen required in the biosynthesis and respiration equations is assumed in the formula for electrolysis. This balanced system is an idealized situation for a closed system involving a human crew and *Cupriavidus necator*.

In certain non-limiting embodiments, the energy efficiency of the reduction of $CO_2$ performed by *C. necator* is over 40 percent. In certain non-limiting embodiments, the energy efficiency of the electrolysis water in space is over 70 percent. In certain non-limiting embodiments, the energy efficiency of electrolysis is over 75 percent. In certain non-limiting embodiments, the net energy efficiency of the overall end-to-end $CO_2$-to-food system (i.e., from electricity to proteinaceous biomass) is over 28 percent. In certain non-limiting embodiments, this net efficiency of the overall system is over ten times higher than the efficiency of an equivalent photosynthetic system. In certain embodiments, the fixed weight of the system comprising electrolyzer and chemoautotrophic bioreactor is lower than the weight of the photobioreactors and lights for an equivalent algal system. In certain embodiments, the fixed weight of the system comprising electrolyzer and chemoautotrophic bioreactor is lower than the weight of the photobioreactors and lights for an equivalent algal system, and/or of the weight of the lights and hydroponic system and/or planters for an equivalent system for higher plant crops.

Example 17

Figure 31:
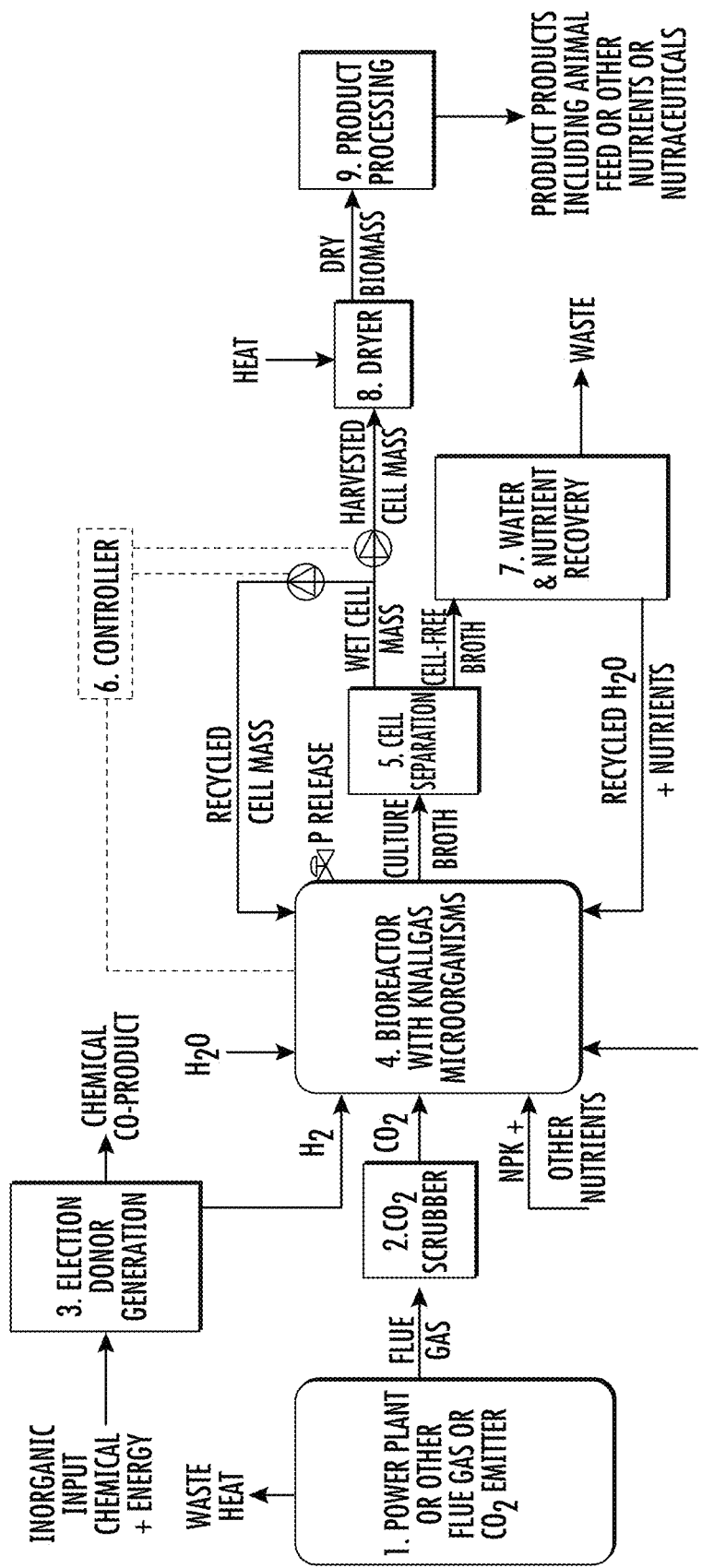
FIG. 31 shows a process flow diagram for an embodiment with capture of $CO_2$ performed by a microorganism capable of performing an oxyhydrogen reaction to produce a protein-rich biomass for animal feed or other nutrients or nutraceuticals.

FIG. 31 illustrates the general process flow diagram for certain embodiments of the present invention that have (A) a process step for the generation of electron donors (e.g., molecular hydrogen electron donors) suitable for supporting chemosynthesis from an energy input and raw inorganic chemical input (e.g., water); (B) followed by delivery of generated $H_2$ electron donors and $O_2$ electron acceptors, water, mineral nutrients, along with $CO_2$ captured from a point industrial flue gas, or other $CO_2$ source, into (C) chemosynthetic reaction step or steps housed with one of more bioreactors (4), which make use of oxyhydrogen microorganisms to capture and fix carbon dioxide, and create proteinaceous biomass through chemosynthetic reactions; (D) in parallel, there is recovery of surplus chemical co-products from the electron donor generation step (e.g. $O_2$); followed by (E) process steps for the recovery of biomass products from the process stream; and (F) recycling of unused nutrients and process water, as well as cell mass needed to maintain the microbial culture, back into the carbon-fixation reaction steps (i.e., back into the bioreactors).

In the particular embodiment diagrammed in FIG. 31, the $CO_2$ containing flue gas is captured from a point source or emitter. Such sources or emitters include but are not limited to power plants, refineries, or cement producers. Electron donors (e.g., $H_2$) needed for chemosynthesis can be generated from input inorganic chemicals and energy. In certain embodiments, the hydrogen is generated through a carbon dioxide emission-free process. Exemplary carbon dioxide emission-free processes for hydrogen generation include, for example, electrolytic or thermochemical processes known in the art, which are powered by energy sources including but not limited to photovoltaics, solar thermal, wind power, hydroelectric, nuclear, geothermal, enhanced geothermal, ocean thermal, ocean wave power, tidal power. The flue gas can be pumped through bioreactors (4) containing oxyhydrogen microorganisms along with electron donors and acceptors needed to drive chemosynthesis and a medium suitable to support the microbial culture and carbon fixation through chemosynthesis. In the non-limiting set of embodiments diagrammed in FIG. 31, hydrogen electron donor and oxygen and carbon dioxide electron acceptors are compressed and added continuously to the growth broth along with other nutrients required for chemosynthesis and culture maintenance and growth, which are pumped into one or more bioreactors containing one or more knallgas microorganisms such as but not limited to one or more of the following: *Cupriavidus necator, Rhodococcus opacus* and/or other *Rhodococcus* sp., *Hydrogenovibrio marinus, Rhodopseudomonas capsulata, Hydrogenobacter thermophilus*, and/or *Xanthobacter autotrophicus*. In the set of non-limiting embodiments illustrated in FIG. 31, oxygen serves as an electron acceptor in the chemosynthetic reaction for the intracellular production of ATP through the oxyhydrogen reaction linked to oxidative phosphorylation. The oxygen can originate from the flue gas and/or it can be generated from the water-splitting reaction used to produce the hydrogen, and/or it can be taken from air. In FIG. 31, carbon dioxide from the flue gas serves as an electron acceptor (non-respiratory; anabolic) for the synthesis of organic compounds including through biochemical pathways utilizing the ATP produced through the respiratory oxyhydrogen reaction, and NADH and/or NADPH produced from the intracellular enzymatically catalyzed reduction of $NAD^+$ or $NADP^+$ by $H_2$. The cell culture may be continuously flowed into and out of the bioreactors. After the cell culture leaves the bioreactors, the cell mass can be separated from the liquid medium (5). Solid-liquid separation can be accomplished using processes and equipment well known in the art such as but not limited to continuous centrifuges or flowing broth through membrane filters to separate the cell mass from the liquid. Cell mass needed to replenish the cell culture population at a desirable (e.g., optimal) level can be recycled back into the bioreactor. Surplus cell mass can be dried (8) to form a dry biomass product which can be further post-processed (9) into various feed, protein, nutritional, fertilizer, chemical, or fuel products. Post-processing of proteinaceous biomass into animal feed and/or plant fertilizer formulations can be performed according to methods known to those skilled in the art. Following the cell separation step, extracellular chemical products of the chemosynthetic reaction can be removed from the process flow and recovered. Then, any undesirable waste products that might be present are removed (7). If necessary, replacement water and/or nutrients can be provided to the bioreactor to make-up for any losses to the biomass product and/or other effluent streams.

Example 18

Chemoautotrophic Strain Screening

Strains were first screened for chemoautotrophy on plates using Almore's Vacu-Quick jar system. Promising strains were then tested in liquid culture.

A minimal salts medium (MSM) was prepared as described above and combined and added in agarose (1.5%) plates aseptically. 162 candidate strains drawn from the following genera were tested: *Cupriavidus; Xanthobacter; Dietzia; Gordonia; Mycobacterium; Nocardia; Pseudonocardia; Arthrobacter; Alcanivorax; Rhodococcus; Streptomyces; Rhodopseudomonas; Rhodobacter*; and *Acinetobacter*.

Each strain was streaked onto a minimal salts medium (MSM)+agarose (1.5%) plate. All the respective plates were then placed in an Almore's Vacu-Quick jar system. At the bottom of each chamber was laid a sterile paper towel soaked with sterile water, in order to maintain humidity in the chamber and prevent the plates from drying during incubation. The gas tight chambers filled with plates were then evacuated; followed by supply of a $H_2$:$CO_2$:Air (70/10/20) gas mixture. The gases provided the sole source of energy and carbon for growth. The gas chambers were incubated at 30° C. for 7-10 days, purging fresh gas mix every day.

For plates that exhibited chemoautotrophic growth/colonies, the colonies were picked and then streaked onto fresh minimal salts medium (MSM)+agarose (1.5%) plates followed by a second incubation in the Almore's Vacu-Quick jar system supplied with $H_2$ and $CO_2$ and air (70/10/20). Strains the exhibiting strong colony growth in this second incubation were then subjected to chemoautotrophic testing in liquid mineral salts medium (MSM).

Experiments were performed in (Chemglass CLS-4209-10, anaerobic, 18×150 mm) Hungate tubes with working volume of 5 mL, capped with solid neoprene rubber stoppers (Wheaton Science Products, No.: 224100331), crimped with an aluminum cap. Tubes were purged with a gas mix of $H_2$:$CO_2$:Air (70/10/20) using a gas manifold designed for high throughput screening. Tubes were purged with fresh gas mix every day.

Tubes were incubated in a Multitron Pro Infors HT shaker at a 450 angle, at 600 rpm and 30° C. for 96 hrs. Optical density at 600 nm was measured by spectrophotometer (Genesys 10S, UV-Vis spectrophotometer, Thermo Scientific) every 24 hours.

The following bacterial strains were identified as being chemoautotrophic on the knallgas mix: *Arthrobacter methylotrophus* DSM 14008; *Rhodococcus opacus* DSM 44304; *Rhodococcus opacus* DSM 44311; *Xanthobacter autotrophicus* DSM 431; *Rhodococcus opacus* DSM 44236; *Rhodococcus ruber* DSM 43338; *Rhodococcus opacus* DSM 44315; *Cupriavidus metallidurans* DSM 2839; *Rhodococcus aetherivorans* DSM 44752; *Gordonia desulfuricans* DSM 44462; *Gordonia polyisoprenivorans* DSM 44266; *Gordonia polyisoprenivorans* DSM 44439; *Gordonia rubripertincta* DSM 46039; *Rhodococcus percolatus* DSM 44240; *Rhodococcus opacus* DSM 43206; *Gordonia hydrophobica* DSM 44015; *Rhodococcus zopfii* DSM 44189; *Gordonia westfalica* DSM 44215, *Xanthobacter autotrophicus* DSM 1618; *Xanthobacter autotrophicus* DSM 2267; *Xanthobacter autotrophicus* DSM 3874; *Streptomyces coelicoflavus* DSM 41471; *Streptomyces griseus* DSM 40236; *Streptomyces* sp. DSM 40434; *Streptomyces xanthochromogenes* DSM 40111; *Streptomyces thermocarboxydus* DSM 44293; *Rhodobacter sphaeroides* DSM 158.

Full proximate analysis was performed on knallgas strains grown in liquid MSM media with a knallgas mixture as the sole carbon and energy source. It was observed that *C. necator* DSM 531 and DSM 541 accumulated over 70% and over 80% total protein by weight, respectively, for samples taken during the arithmetic growth phase. Both *C. necator* DSM 531 and DSM 541 were also observed to synthesize vitamins, including vitamin B1, vitamin B2, and vitamin B12.

Example 19

Figure 32:
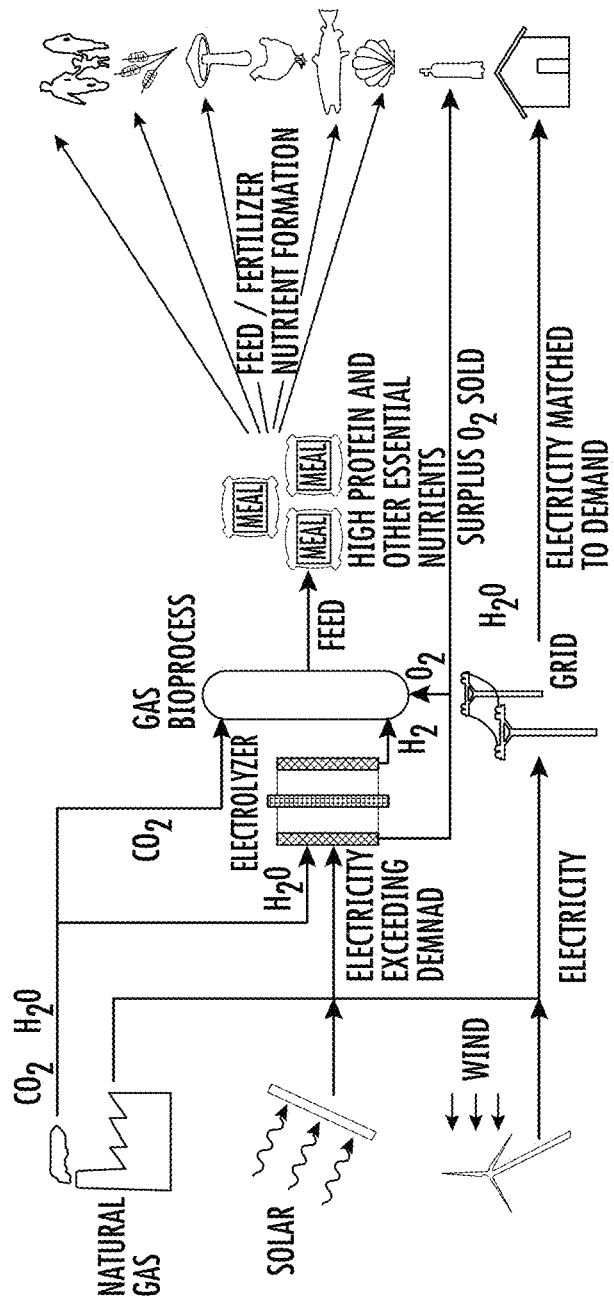
FIG. 32 shows a diagram of an integrated system converting waste $CO_2$ and off-peak, intermittent renewable energy into high protein feed, fertilizer, and nutrients. In addition to the capture of $CO_2$ and production of valuable nutrients, the system relieves strain on the grid from excess renewable generation during periods of low demand. It also enables more complete utilization of renewable capacity by allowing the renewables to keep generating even during periods of low demand.

Certain embodiments of the present invention leverage intermittent renewable sources of power, such as solar and wind, to produce the $H_2$ required for carbon fixation. The $CO_2$ source is an industrial source, such as a power plant. Electrolyzers generally draw power during periods of low electrical demand and high renewable power supply. During such periods of low demand and high renewable generation, the renewable, $CO_2$-emission free content of the electrical supply reaches up to 95% in regions such as Texas, Scotland and Germany. Thus, in effect the electrolyzer is drawing upon $CO_2$ emissions-free power for the production of $H_2$ from water, and utilizes little if any $CO_2$-intensive power. In such regions, the periods of high renewable power supply and low grid demand occur roughly 50% of the time and thus the electrolyzer is expected to operate roughly 50% of the time. Onsite $H_2$ and $CO_2$ tank storage buffer the difference in timing between $CO_2$ production from the industrial source and $H_2$ production from the electrolyzer, enabling a continuous flow of both of these gases into the $CO_2$-fixing bioprocess. The chemoautotrophic knallgas microbes convert $CO_2$, $H_2$, and mineral nutrients (i.e. NPK) into high protein biomass (see FIG. 32). $O_2$ from the electrolyzer exceeds the requirements of the micro-aerobic knallgas bioprocess. This surplus $O_2$ can be sold as a pure gas co-product, or is fed back to a fossil combustion or power unit in order to increase thermal efficiency of the unit and increase the concentration of $CO_2$ in the flue gas stream emerging from the unit. Increased concentration of $CO_2$ facilitates the carbon capture step.

In some embodiments, the overall inventive process integrates three main parts, two of which may apply commercially available units, and the chemoautotrophic $CO_2$-fixing bioprocess and associated post-process steps described herein. The two commercially available units at the front end for the provision of $CO_2$ and $H_2$ to the bioprocess are: $CO_2$ flue gas scrubbing; and the electrolysis of water using primarily renewable power. To achieve carbon neutrality, the system may be located in regions with high intermittent renewable power generation. The electrolyzer unit only draws power during periods of low electrical demand and renewable power oversupply. This relieves strain on the electrical grid caused by intermittent renewable energy. A major current application for electrolyzer technology is to convert the $H_2$ produced during periods of oversupply of renewable power back into grid electricity during periods of high demand and low renewable power supply—in effect going back down the value chain from $H_2$ to electricity. The process described herein converts $H_2$ and $CO_2$ into protein—in effect continuing further up the value chain, from $H_2$ to protein.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated in the appended claims.

All publications, patents, and patent applications cited herein are hereby incorporated by reference in their entireties for all purposes and to the same extent as if each individual publication, patent, or patent application were specifically and individually indicated to be so incorporated by reference.

REFERENCES

1. J. E. Bailey and D. F. Ollis. *Biochemical Engineering Fundamentals*. Chemical engineering. McGraw-Hill, 1986.
2. L. Bongers. Energy generation and utilization in hydrogen bacteria. *Journal of bacteriology*, 104(1):145-151, October 1970.
3. G. L. Drake, C. D. King, W. A. Johnson, and E. A. Zuraw. Study of life support systems for space missions exceeding one year in duration. Technical Report SP-134, NASA, April 1966.
4. Curt R. Fischer, Daniel Klein-Marcuschamer, and Gregory Stephanopoulos. Selection and optimization of microbial hosts for biofuels production. *Metabolic Engineering*, 10(6):295-304, November 2008.
5. Michele R. Hamester, Palova S. Balzer, and Daniela Becker. Characterization of calcium carbonate obtained from oyster and mussel shells and incorporation in polypropylene. *Materials Research*, 15:204-208, 2012.
6. R. Heise, V. Müller, and G. Gottschalk. Sodium dependence of acetate formation by the acetogenic bacterium *Acetobacterium woodii*. *Journal of Bacteriology*, 171(10): 5473-5478, October 1989.
7. Michael Hugler, Carl O. Wirsen, Georg Fuchs, Craig D. Taylor, and Stefan M. Sievert. Evidence for autotrophic CO2 fixation via the reductive tricarboxylic acid cycle by members of the ε subdivision of proteobacteria. *Journal of Bacteriology*, 187(9):3020-3027, May 2005.
8. J. K. Kristjansson. *Thermophilic Bacteria*. Taylor & Francis, 1992.
9. Sang Y. Lee, Jin H. Park, Seh H. Jang, Lars K. Nielsen, Jaehyun Kim, and Kwang S. Jung. Fermentative butanol production by clostridia. *Biotechnol. Bioeng.*, 101(2):209-228, October 2008.
10. J. Lengeler, G. Drews, and H. Schlegel. *Biology of the Prokaryotes*. Wiley, 2009.
11. L. G. Ljungdahl. The autotrophic pathway of acetate synthesis in acetogenic bacteria. *Annual Review of Microbiology*, 40(1):415-450, 1986.
12. Akane Miura, Masafumi Kameya, Hiroyuki Arai, Masaharu Ishii, and Yasuo Igarashi. A soluble NADH-dependent fumarate reductase in the reductive tricarboxylic acid cycle of *Hydrogenobacter thermophilus* TK-6. *Journal of bacteriology*, 190(21):7170-7177, November 2008.
13. Eleftherios T. Papoutsakis. Equations and calculations for fermentations of butyric acid bacteria. *Biotechnol. Bioeng.*, 26(2):174-187, February 1984.
14. Kathleen M. Scott and Colleen M. Cavanaugh. CO2 uptake and fixation by endosymbiotic chemoautotrophs from the bivalve solemya velum. *Applied and Environmental Microbiology*, 73(4):1174-1179, February 2007.
15. J. M. Shively, G. van Keulen, and W. G. Meijer. Something from almost nothing: carbon dioxide fixation in chemoautotrophs. *Annual review of microbiology*, 52:191-230, 1998.
16. Arnold J. Smith, Jack London, and Roger Y. Stanier. Biochemical basis of obligate autotrophy in Blue-Green algae and thiobacilli. *Journal of Bacteriology*, 94(4):972-983, October 1967.
17. F. B. Taub, F. E. Palmer, R. E. Condrey, R. B. Kern, K. A. Ballard, and D. F. Kalamasz. Algal culture as aquaculture feed. *Research in fisheries*, 1973.
18. Frieda B. Taub. Closed ecological systems. *Annual Review of Ecology and Systematics*, 5:139-160, 1974.
19. Rudolf K. Thauer, Anne-Kristin Kaster, Henning Seedorf, Wolfgang Buckel, and Reiner Hedderich. Methanogenic archaea: ecologically relevant differences in energy conservation. *Nature Reviews Microbiology*, 6(8):579-591, June 2008.
20. Gil-Lim Yoon, Byung-Tak Kim, Baeck-Oon Kim, and Sang-Hun Han. Chemical-mechanical characteristics of crushed oyster-shell. *Waste Management*, 23(9):825-834, January 2003.
21. Hyunsuk Yoon, Sangkyu Park, Kiho Lee, and Junboum Park. Oyster shell as substitute for aggregate in mortar. *Waste Management & Research*, 22(3):158-170, June 2004.
22. Closed Ecological Systems Annual Review of Ecology and Systematics, Vol. 5 (1974), pp. 139-160 by Frieda B. Taub, and G. L. Drake, C. D. King, W. A. Johnson, and E. A. Zuraw, "Study of life support systems for space missions exceeding one year in duration," NASA, Tech. Rep. SP-134, April 1966

We claim:

1. A feed, nutritional, or fertilizer product comprising protein produced by *Xanthobacter* microorganisms,
    wherein said protein is produced in a method that comprises chemoautotrophic capture and conversion of a carbon source by said *Xanthobacter* microorganisms into biomass comprising protein, and wherein said method comprises:
    (a) introducing a gaseous substrate into an environment comprising *Xanthobacter* microorganisms, wherein said environment is suitable for culturing said *Xanthobacter* microorganisms, and wherein said gaseous substrate comprises said carbon source selected from the group consisting of an inorganic molecule comprising only one carbon atom, an organic molecule comprising only one carbon atom, and a combination thereof, wherein said *Xanthobacter* microorganisms chemoautotrophically convert the carbon source via at least one chemosynthetic carbon-fixing reaction and at least one anabolic biosynthetic pathway into said chemoautotrophically produced biomass of *Xanthobacter* microorganisms, and wherein said chemoautotrophically produced biomass of *Xanthobacter* microorganisms comprises protein in a quantity that is greater than 10% of the total cell mass, wherein the at least one chemosynthetic carbon-fixing reaction and the at least one anabolic biosynthetic pathway are at least partially driven by chemical and/or electrochemical energy provided by electron donors and electron acceptors that have been generated chemically, electrochemically, and/or thermochemically, and/or which are introduced into the environment from at least one source external to the environment, wherein said electron acceptors comprise $O_2$, and wherein protein produced by said *Xanthobacter* microorganisms comprises biological nutrients capable of feeding, providing nutrition to, or fertilizing one or more other organisms; and (b) recovering said biomass from said environment, and processing the biomass into the feed, nutritional, or fertilizer product comprising protein produced by *Xanthobacter* microorganisms.

2. The feed, nutritional, or fertilizer product according to claim 1, wherein said *Xanthobacter* microorganisms comprise *Xanthobacter autotrophicus* or *Xanthobacter flavus*.

3. The feed, nutritional, or fertilizer product according to claim 2, wherein said *Xanthobacter* microorganisms are *Xanthobacter autotrophicus* strain DSM 431, DSM 432, DSM 1618, DSM 2267, or DSM 3874.

4. The feed, nutritional, or fertilizer product according to claim 1, wherein said protein and/or said chemoautotrophically produced biomass of *Xanthobacter* microorganisms are not deficient in any essential amino acids.

5. The feed, nutritional, or fertilizer product according to claim 1, wherein said protein and/or said chemoautotrophically produced biomass of *Xanthobacter* microorganisms are not deficient in lysine or methionine.

6. The feed, nutritional, or fertilizer product according to claim 1, wherein said product further comprises a B vitamin selected from the group consisting of vitamin B1, B2, and B12.

7. The feed, nutritional, or fertilizer product according to claim 1, wherein said product further comprises carbohydrates produced by said *Xanthobacter* microorganisms.

8. The feed, nutritional, or fertilizer product according to claim 1, wherein said product further comprises protoplasm or an extract of protoplasm produced by said *Xanthobacter* microorganisms, wherein said protoplasm is of nutritional value to humans, animals, and/or other heterotrophs.

9. The feed, nutritional, or fertilizer product according to claim 1, wherein said product does not comprise cell mass or biomass or organic molecules derived from a photosynthetic organism.

10. The feed, nutritional, or fertilizer product according to claim 1, wherein said chemoautotrophically produced biomass of *Xanthobacter* microorganisms further comprises hydrogen that is derived entirely from water ($H_2O$) and carbon that is derived entirely from carbon dioxide ($CO_2$) captured from the atmosphere and/or from greenhouse gas emissions.

11. The feed, nutritional, or fertilizer product according to claim 1, wherein said biomass of *Xanthobacter* microorganisms further comprises nitrogen that is derived from ammonia, ammonium, urea, and/or nitrate that is recovered from urine, agricultural waste, fish waste, aquaculture waste, and/or other animal waste.

12. The feed, nutritional, or fertilizer product according to claim 1, wherein said biomass of *Xanthobacter* microorganisms further comprises phosphorous that is derived from phosphate recovered from urine, agricultural waste, fish waste, aquaculture waste, and/or other animal waste.

13. The feed, nutritional, or fertilizer product according to claim 1, wherein said *Xanthobacter* microorganisms are grown within a consortium of microorganisms in said environment that is suitable for culturing said *Xanthobacter* microorganisms.

14. The feed, nutritional, or fertilizer product according to claim 1, wherein said product does not comprise gossypol, glucosinolates, saponins, or trypsin inhibitors.

15. The feed, nutritional, or fertilizer product according to claim 1, wherein step (a) comprises introducing at least one nitrogen source into environment, wherein said at least one nitrogen source is selected from the group consisting of ammonia, ammonium, urea, nitrate, and a combination thereof.

16. The feed, nutritional, or fertilizer product according to claim 1, wherein step (a) comprises pumping at least one gas to said environment, wherein said at least one gas is selected from the group consisting of syngas, producer gas, pyrolysis gas, hydrogen gas, CO, $CO_2$, $O_2$, air, an air/$CO_2$ mixture, natural gas, biogas, methane, ammonia, nitrogen gas, and a combination thereof.

* * * * *